(12) United States Patent
Gunaga et al.

(10) Patent No.: US 10,851,108 B2
(45) Date of Patent: Dec. 1, 2020

(54) SUBSTITUTED BICYCLIC HETEROCYCLIC COMPOUNDS

(71) Applicant: BRISTOL-MYERS SQUIBB COMPANY, Princeton, NJ (US)

(72) Inventors: Prashantha Gunaga, Bangalore (IN); Jeremy Richter, Yardley, PA (US); Navnath Dnyanoba Yadav, Bangalore (IN); Manoranjan Panda, Bangalore (IN); Sreenivasulu Godesi, Ardhaveedu Mandal (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 10 days.

(21) Appl. No.: 16/094,288

(22) PCT Filed: Apr. 19, 2017

(86) PCT No.: PCT/US2017/028231
§ 371 (c)(1),
(2) Date: Oct. 17, 2018

(87) PCT Pub. No.: WO2017/184662
PCT Pub. Date: Oct. 26, 2017

(65) Prior Publication Data
US 2019/0127380 A1    May 2, 2019

Related U.S. Application Data

(60) Provisional application No. 62/325,255, filed on Apr. 20, 2016.

(51) Int. Cl.
| | |
|---|---|
| *A61K 31/519* | (2006.01) |
| *C07D 487/04* | (2006.01) |
| *C07D 471/04* | (2006.01) |
| *C07D 271/04* | (2006.01) |
| *C07D 407/04* | (2006.01) |
| *C07D 407/06* | (2006.01) |
| *C07D 413/14* | (2006.01) |
| *C07D 519/00* | (2006.01) |

(52) U.S. Cl.
CPC ......... *C07D 487/04* (2013.01); *C07D 271/04* (2013.01); *C07D 407/04* (2013.01); *C07D 407/06* (2013.01); *C07D 413/14* (2013.01); *C07D 471/04* (2013.01); *C07D 519/00* (2013.01)

(58) Field of Classification Search
CPC .................................................. A61K 31/519
See application file for complete search history.

(56) References Cited

FOREIGN PATENT DOCUMENTS

| EP | 0372694 A2 | 6/1990 |
|---|---|---|
| WO | WO2005105759 A1 | 11/2005 |
| WO | WO2013028474 A1 | 2/2013 |
| WO | WO2013062900 A1 | 5/2013 |
| WO | WO2014015495 A1 | 1/2014 |
| WO | WO2014018764 A1 | 1/2014 |
| WO | WO2014085210 A1 | 6/2014 |
| WO | WO2014126944 A2 | 8/2014 |
| WO | WO2014099633 A3 | 10/2014 |
| WO | WO2015011164 A1 | 1/2015 |
| WO | WO2015017305 A1 | 2/2015 |
| WO | WO2015065866 A1 | 5/2015 |
| WO | WO2015095097 A2 | 6/2015 |
| WO | WO-2015095097 A2 * | 6/2015 |
| WO | WO2015100147 A1 | 7/2015 |
| WO | WO2015105736 A1 | 7/2015 |
| WO | WO2016008064 A1 | 1/2016 |
| WO | WO2016010802 A1 | 1/2016 |

* cited by examiner

*Primary Examiner* — John S Kenyon
(74) *Attorney, Agent, or Firm* — Mary K. VanAtten

(57) ABSTRACT

Disclosed are compounds of Formula (I), or a salt thereof, wherein: X is $CR_4$ or N; Y is $CR_4$ or N, provided that Y is N only if X is N; $R_1$ is Formulae (A) or (B); each W is independently $NR_{1b}$ or O; Z is a bond or $CHR_{1d}$; and $R_1$, $R_2$, $R_3$, $R_4$, $L_1$, $R_{1a}$, $R_{1b}$, $R_{1c}$, and n are defined herein. Also disclosed are methods of using such compounds as inhibitors of ROMK, and pharmaceutical compositions comprising such compounds. These compounds are useful in treating cardiovascular diseases.

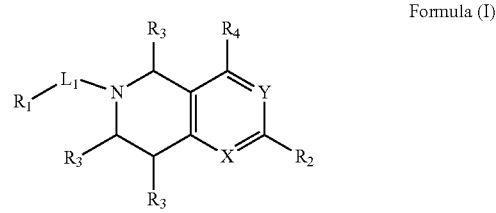

Formula (I)

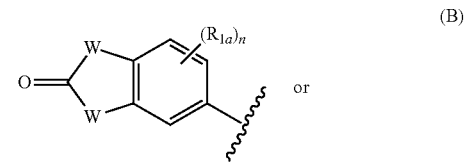

(B)

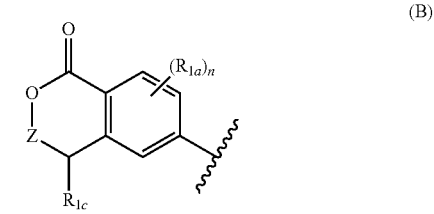

(B)

14 Claims, No Drawings

SUBSTITUTED BICYCLIC HETEROCYCLIC COMPOUNDS

CROSS-REFERENCE TO RELATED APPLICATIONS

This application is a 371 application of PCT/US2017/028231 filed Apr. 19, 2017 which claims priority of U.S. Provisional Application Ser. No. 62/325,255, filed Apr. 20, 2016, which is incorporated herein in its entirety.

DESCRIPTION

The present invention generally relates to substituted bicyclic heterocyclic compounds useful as inhibitors of ROMK channel activity. Provided herein are substituted bicyclic heterocyclic compounds, compositions comprising such compounds, and methods of their use. The invention further pertains to pharmaceutical compositions containing at least one compound according to the invention that are useful for the treatment of conditions related to ROMK channel activity, including cardiovascular diseases.

The renal outer medullary potassium (ROMK, Kir1.1) channel is a weak inward rectifying $K^+$ channel with a key role in renal $K^+$ recycling and secretion (Ho et al., *Nature*, 1993, 362, 31-38; Shuck et al., *The Journal of Biological Chemistry*, 1994, 269(39), 24261-24270; Lee and Hebert, *American Journal of Physiology-Renal Physiology*, 1995, 268(6), F1124-F1131; Lu et al., *The Journal of Biological Chemistry*, 2002, 277, 37881-37887; and Hebert et al., *Physiological Reviews*, 2005, 85:319-371). In the thick ascending limb (TAL) of a nephron, ROMK channel activity provides the $K^+$ gradient necessary for Na and Cl reabsorption by the $Na^+$—$K^+$-$2Cl^-$ (NKCC2) co-transporter. In the distal convoluted tubule (DCT) and cortical collecting duct (CCD), ROMK channels form the major secretory pathway for $K^+$ and as a result, play an important role in $K^+$ homeostasis under physiological conditions (Welling and Ho, *American Journal of Physiology-Renal Physiology*, 2009, 297(4): F849-F863).

Multiple lines of evidence indicate that inhibition of ROMK channel activity results in natriuresis, diuresis and reduced blood pressure. Therefore, ROMK inhibition may offer a novel mechanism of blood pressure regulation and diuresis in patients suffering from hypertension, congestive heart failure or any other edematous disease conditions. The activity of NKCC2 transporter is tightly coupled with ROMK activity in the TAL region and homozygous loss of function mutations in ROMK in humans result in a disease phenotype (renal salt wasting, increased aldosterone levels, metabolic alkalosis, reduction in blood pressure) very similar to that of NKCC2 homozygous mutations but with a milder hypokalemia (Simon et al., *Nature Genetics*, 1996, 14: 152-156). In addition, humans identified with heterozygous ROMK mutations from the Framingham Heart Study presented with reduced blood pressure (Ji et al., *Nature Genetics*, 2008, 40(5): 592-599). Similar to human genetics, mouse genetics also support the role of ROMK in $Na^+$ reabsorption in the kidney and overall blood pressure regulation (Lu et al., *The Journal of Biological Chemistry*, 2002, 277, 37881-37887; and Lorenz et al., *The Journal of Biological Chemistry*, 2002, 277: 37871-37880). Furthermore, pharmacological blockade of the ROMK channel has been shown to induce natriuresis and diuresis in rats upon acute dosing and in dogs upon both acute and prolonged dosing (Tang et al., *Bioorganic and Medicinal Chemistry Letter*, 2013, 23: 5829-5832; Garcia et al., *The Journal of Pharmacology and Experimental Therapeutics*, 2014, 348: 153-164; Walsh et al., *ACS Medicinal Chemistry Letters*, 2015, 6: 747-752; and Dajee et al., *Circulation*, 2014, 130: A12397). Since the ROMK channel is also implicated in regulation of net $K^+$ secretion in the distal part of the nephron, it is believed that ROMK inhibition in this region will mitigate the $K^+$ wasting and hypokalemia associated with loop and thiazide diuretics. Acute or prolonged (up to 122 days) ROMK antagonism does not lead to kaliuresis or hypokalemia in dogs (Garcia et al., *The Journal of Pharmacology and Experimental Therapeutics*, 2014, 348: 153-164; Walsh et al., *ACS Medicinal Chemistry Letters*, 2015, 6: 747-752; Dajee et al., *Circulation*, 2014, 130: A12397). Together, these data suggest that inhibition of ROMK may produce diuretic efficacy that is equivalent to or better than currently available loop diuretics and with potentially lower incidence of hypokalemia.

WO 2015/095097 discloses compounds useful as inhibitors of ROMK. Other publications disclosing compounds useful as inhibitors of ROMK include WO 2010/129379, WO 2010/136144, WO 2012/058116, WO 2012/058134, WO 2013/028474, WO 2013/039802, WO 2013/062892, WO 2013/062900, WO 2013/066714, WO 2013/066717, WO 2013/066718, WO 2013/090271, WO 2014/015495, WO 2014/018764, WO 2014/085210, WO 2014/099633, WO 2014/126944, WO 2014/150132, WO 2015/017305, WO 2015/065866, WO 2015/095097, WO 2015/100147, WO 2015/105736, WO 2016/008064, WO 2016/010801, WO 2016/010802, WO2016/060941, WO2016/065582, WO2016/065602, WO2016/065603, WO2016/069426, WO2016/069427, WO2016/069428, WO2016/069430, WO2016/091042, WO2016/122994, WO2016/127358, WO2016/130444, and CN105693706.

In view of the numerous conditions that are contemplated to benefit by treatment involving inhibition of ROMK, it is immediately apparent that new compounds capable of inhibiting ROMK and methods of using these compounds should provide substantial therapeutic benefits to a wide variety of patients.

The present invention relates to a new class of substituted bicyclic heterocyclic compounds found to be effective inhibitors of ROMK. These compounds are provided to be useful as pharmaceuticals with desirable stability, bioavailability, therapeutic index, and toxicity values that are important to their drugability.

SUMMARY OF THE INVENTION

The present invention provides compounds of Formula (I) that are useful as inhibitors of ROMK, and are useful for the treatment of cardiovascular diseases and prophylaxis and/or treatment of diuresis or natriuresis.

The present invention also provides pharmaceutical compositions comprising a pharmaceutically acceptable carrier and at least one of the compounds of Formula (I) or stereoisomers, tautomers, pharmaceutically acceptable salts, solvates, or prodrugs thereof.

The present invention also provides a method for inhibiting ROMK comprising administering to a host in need of such treatment a therapeutically effective amount of at least one of the compounds of Formula (I) or stereoisomers, tautomers, pharmaceutically acceptable salts, solvates, or prodrugs thereof.

The present invention also provides a method for treating cardiovascular disease comprising administering to a host in need of such treatment a therapeutically effective amount of at least one of the compounds of Formula (I) or stereoisomers, tautomers, pharmaceutically acceptable salts, solvates, or prodrugs thereof.

One embodiment provides a method for treating cardiovascular disease. Particular, cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

One embodiment provides a method for promotion of diuresis or natriuresis.

The present invention also provides the compounds of the present invention or stereoisomers, tautomers, pharmaceutically acceptable salts, solvates, or prodrugs thereof, for use in therapy.

The present invention also provides the use of the compounds of the present invention or stereoisomers, tautomers, pharmaceutically acceptable salts, solvates, or prodrugs thereof, for the manufacture of a medicament for the treatment of cardiovascular disease or prophylaxis and/or promotion of diuresis or natriuresis.

The present invention also provides a compound of Formula (I) or a pharmaceutical composition in a kit with instructions for using the compound or composition.

The present invention also provides processes and intermediates for making the compounds of the present invention or stereoisomers, tautomers, pharmaceutically acceptable salts, solvates, or prodrugs thereof.

These and other features of the invention will be set forth in the expanded form as the disclosure continues.

DETAILED DESCRIPTION

In a first aspect of the present invention provides at least one compound of Formula (I):

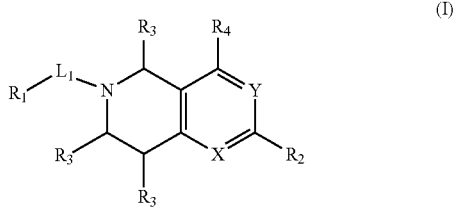

(I)

or a salt thereof, wherein:
X is $CR_4$ or N;
Y is $CR_4$ or N, provided that Y is N only if X is N;
$R_1$ is:

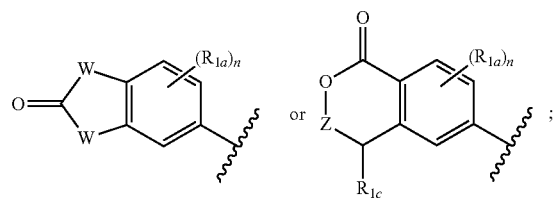

each W is independently $NR_{1b}$ or O;
Z is a bond or $CHR_{1d}$;

each $R_{1a}$ is independently H, F, Cl, —OH, $C_{1-3}$ alkyl, $C_{1-3}$ fluoroalkyl, $C_{3-6}$ cycloalkyl, $C_{1-3}$ alkoxy, or $C_{1-3}$ fluoroalkoxy;
each $R_{1b}$ is independently H, $C_{1-3}$ alkyl, $C_{1-3}$ fluoroalkyl, aryl, or heteroaryl;
$R_{1c}$ is H, $C_{1-4}$ alkyl, or $C_{3-6}$ cycloalkyl;
$R_{1d}$ is H, $C_{1-3}$ alkyl, $C_{3-6}$ cycloalkyl, or $C_{1-3}$ alkoxy;
n is zero, 1, 2, or 3;
$L_1$ is a bond, —$CHR_b$—, or —$CHR_aCHR_b$—;
$R_a$ is H, halo, —OH, $C_{1-4}$ alkyl, $C_{1-3}$ fluoroalkyl, $C_{1-3}$ hydroxyalkyl, $C_{3-6}$ cycloalkyl, $C_{1-3}$ alkoxy, or $C_{1-3}$ fluoroalkoxy;
$R_b$ is H, $C_{1-4}$ alkyl, $C_{1-3}$ fluoroalkyl, $C_{1-3}$ hydroxyalkyl, $C_{3-6}$ cycloalkyl, $C_{1-3}$ alkoxy, or $C_{1-3}$ fluoroalkoxy;
$R_2$ is $R_{2a}$ or -$L_2$-$R_{2b}$;
$L_2$ is —$NR_c$— or —$NR_cCH_2$—;
$R_c$ is H, $C_{1-3}$ alkyl, $C_{1-3}$ fluoroalkyl, $C_{3-6}$ cycloalkyl, or ($C_{1-3}$ alkoxy)-($C_{1-3}$ alkylenyl);
$R_{2a}$ is a nitrogen-linked heterocyclyl selected from imidazolyl, indolinyl, morpholinyl, piperidinyl, pyrazolyl, pyrrolidinyl, pyrrolyl, triazolyl, 1,2,3,4-tetrahydro-1,5-naphthyridinyl, 1,2,3,4-tetrahydro-1,7-naphthyridinyl, 1,2,3,4-tetrahydroquinolinyl, 1,2,3-triazolo[4,5-b]pyridinyl, benzo[d][1,2,3]triazolyl, benzo[d]imidazolyl, imidazo[4,5-b]pyridinyl, imidazo[4,5-c]pyridinyl, indazolyl, indolyl, pyrazolo[3,4-b] pyrazinyl, pyrazolo[3,4-b]pyridinyl, pyrazolo[3,4-c]pyridinyl, pyrazolo[4,3-b] pyridinyl, pyrazolo[4,3-c]pyridinyl, pyrazolo[4,3-d]pyrimidinyl, pyrrolo[2,3-b] pyridinyl, pyrrolo[2,3-c]pyridinyl, pyrrolo[3,2-b] pyridinyl, pyrrolo[3,2-c]pyridinyl, 2,3-dihydro-pyrrolo[2,3-b]pyridinyl, 2,3-dihydro-pyrrolo[2,3-c]pyridinyl, 2,3-dihydro-pyrrolo[3,2-b]pyridinyl, 2,3-dihydro-pyrrolo[3,2-c]pyridinyl, 3,4-dihydro-benzo[b][1,4]oxazinyl, imidazo[4,5-b]pyridinyl, imidazo[4,5-c]pyridinyl, 5,6,7,8-tetrahydropyrido[3,2-d]pyrimidinyl, pyrrolo[2,3-b] pyrazinyl, pyrrolo[3,2-c]pyridazinyl, pyrrolo[3,2-d]pyrimidinyl, 6,7-dihydro-pyrrolo[3,2-d]pyrimidinyl, and purinyl, wherein each of said heterocyclyl is substituted with zero to 4 $R_d$;
$R_{2b}$ is phenyl or a carbon-linked heterocyclyl selected from pyrrolyl, furan, thiophenyl, imidazolyl, oxazolyl, thiazolyl, pyrazolyl, isoxazolyl, isothiazolyl, 1,2,3-triazolyl, 1,2,3-thiadiazolyl, 1,3,4-thiadiazolyl, 1,2,3-oxadiazolyl, 1,3,4-oxadiazolyl, 1,2,4-triazolyl, tetrazolyl, pyridinyl, pyridazinyl, pyrimidinyl, pyrazinyl, 1,2,4-triazinyl, benzo[c][1,2,5]oxadiazolyl, benzo[c]isothiazolyl, benzo[c]isoxazolyl, benzo[d]imidazolyl, benzo[d]isothiazolyl, benzo[d]isoxazolyl, benzo[d]oxazol-2(3H)-onyl, benzo[d] oxazolyl, benzo[d]thiazolyl, indazolyl, indolyl, isobenzofuran-1(3H)-onyl, isochroman-1-only, pyrazolo[1,5-a]pyrimidinyl, pyrrolo[2,3-b]pyridinyl, pyrrolo[2,3-c]pyridinyl, pyrrolo[3,2-b]pyridinyl, and pyrrolo[3,2-c]pyridinyl; wherein each of said phenyl and said heterocyclyl is substituted with zero to 4 $R_d$;
each $R_3$ is independently H, $C_{1-3}$ alkyl, $C_{1-3}$ haloalkyl, $C_{1-3}$ hydroxyalkyl, $C_{3-6}$ cycloalkyl, ($C_{1-3}$ alkoxy)-($C_{1-3}$ alkylenyl), —$C(O)OR_e$, or —$C(O)NR_eR_e$;
each $R_4$ is independently H, $C_{1-3}$ alkyl, $C_{1-3}$ haloalkyl, $C_{1-3}$ hydroxyalkyl, $C_{3-6}$ cycloalkyl, ($C_{1-3}$ alkoxy)-($C_{1-3}$ alkylenyl), aryl, heteroaryl, —$CO_2H$, —$CO_2R_e$, —$CONHR_e$, —$CONR_eR_e$, or —$NR_{4a}R_{4a}$, wherein each of said cycloalkyl, aryl, and said heteroaryl is substituted with zero to 3 $R_d$;
each $R_{4a}$ is independently H, $C_{1-3}$ alkyl, $C_{1-3}$ fluoroalkyl, $C_{3-6}$ cycloalkyl, aryl, or heteroaryl, wherein each of said cycloalkyl, aryl, and said heteroaryl is substituted with zero to 3 $R_d$; or two $R_{4a}$ along with the nitrogen atom to which they are attached form a 3-7 membered heterocyclyl;

each $R_d$ is independently F, Cl, —OH, —CN, $C_{1-3}$ alkyl, $C_{1-3}$ fluoroalkyl, $C_{3-6}$ cycloalkyl, $C_{1-3}$ alkoxy, $C_{1-3}$ fluoroalkoxy, —C(O)OR$_e$, —C(O)NR$_e$R$_e$, —OC(O)NR$_e$R$_e$, —NHC(O)OR$_e$, —NR$_e$C(O)OR$_e$, —S(O)$_2$R$_e$, or tetrazolyl; and each $R_e$ is independently H, $C_{1-3}$ alkyl, $C_{1-3}$ fluoroalkyl, $C_{3-6}$ cycloalkyl, aryl, or heteroaryl; or two $R_e$ along with the nitrogen atom to which they are attached form a 3-7 membered heterocyclyl.

In another aspect of the present invention provides at least one compound of Formula (I):

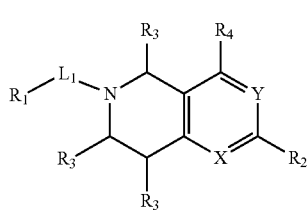

(I)

or a salt thereof, wherein:
X is CR$_4$ or N;
Y is CR$_4$ or N, provided that Y is N only if X is N;
R$_1$ is:

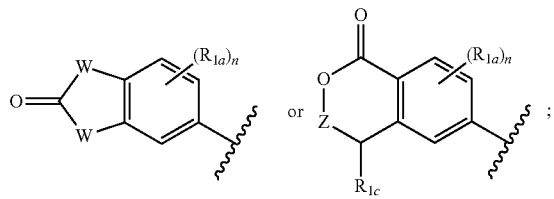

;

each W is independently NR$_{1b}$ or O;
Z is a bond or CHR$_{1d}$;
each $R_{1a}$ is independently H, F, Cl, —OH, $C_{1-3}$ alkyl, $C_{1-3}$ fluoroalkyl, $C_{3-6}$ cycloalkyl, $C_{1-3}$ alkoxy, or $C_{1-3}$ fluoroalkoxy;
each $R_{1b}$ is independently H, $C_{1-3}$ alkyl, $C_{1-3}$ fluoroalkyl, $C_{3-6}$ cycloalkyl, aryl, or heteroaryl;
$R_{1c}$ is H, $C_{1-4}$ alkyl, or $C_{3-6}$ cycloalkyl;
$R_{1d}$ is H, $C_{1-3}$ alkyl, or $C_{3-6}$ cycloalkyl;
n is zero, 1, 2, or 3;
L$_1$ is a bond, —CHR$_b$—, or —CHR$_a$CHR$_b$—;
$R_a$ is H, halo, —OH, $C_{1-4}$ alkyl, $C_{1-3}$ fluoroalkyl, $C_{1-3}$ hydroxyalkyl, $C_{3-6}$ cycloalkyl, $C_{1-3}$ alkoxy, or $C_{1-3}$ fluoroalkoxy;
$R_b$ is H, $C_{1-4}$ alkyl, $C_{1-3}$ fluoroalkyl, $C_{1-3}$ hydroxyalkyl, $C_{3-6}$ cycloalkyl, $C_{1-3}$ alkoxy, or $C_{1-3}$ fluoroalkoxy;
$R_2$ is $R_{2a}$ or -L$_2$-R$_{2b}$;
L$_2$ is —NR$_c$— or —NR$_c$CH$_2$—;
$R_c$ is H, $C_{1-3}$ alkyl, $C_{1-3}$ fluoroalkyl, $C_{3-6}$ cycloalkyl, or ($C_{1-3}$ alkoxy)-($C_{1-3}$ alkylenyl);
$R_{2a}$ is a nitrogen-linked heterocyclyl selected from imidazolyl, indolinyl, morpholinyl, piperidinyl, pyrazolyl, pyrrolidinyl, pyrrolyl, triazolyl, 1,2,3,4-tetrahydro-1,5-naphthyridinyl, 1,2,3,4-tetrahydro-1,7-naphthyridinyl, 1,2,3,4-tetrahydroquinolinyl, 1,2,3-triazolo[4,5-b]pyridinyl, benzo[d][1,2,3]triazolyl, benzo[d]imidazolyl, imidazo[4,5-b]pyridinyl, imidazo[4,5-c]pyridinyl, indazolyl, indolyl, pyrazolo[3,4-b] pyrazinyl, pyrazolo[3,4-b]pyridinyl, pyrazolo[3,4-c]pyridinyl, pyrazolo[4,3-b] pyridinyl, pyrazolo[4,3-c]pyridinyl, pyrazolo[4,3-d]pyrimidinyl, pyrrolo[2,3-b] pyridinyl, pyrrolo[2,3-c]pyridinyl, pyrrolo[3,2-b]pyridinyl, pyrrolo[3,2-c]pyridinyl, 2,3-dihydro-pyrrolo[2,3-b]pyridinyl, 2,3-dihydro-pyrrolo[2,3-c]pyridinyl, 2,3-dihydro-pyrrolo[3,2-b]pyridinyl, 2,3-dihydro-pyrrolo[3,2-c]pyridinyl, 3,4-dihydro-benzo[b][1,4]oxazinyl, imidazo[4,5-b]pyridinyl, imidazo[4,5-c]pyridinyl, 5,6,7,8-tetrahydropyrido[3,2-d]pyrimidinyl, pyrrolo[2,3-b] pyrazinyl, pyrrolo[3,2-c]pyridazinyl, pyrrolo[3,2-d]pyrimidinyl, 6,7-dihydro-pyrrolo[3,2-d]pyrimidinyl, and purinyl, wherein each of said heterocyclyl is substituted with zero to 4 $R_d$;

$R_{2b}$ is phenyl or a carbon-linked heterocyclyl selected from pyrrolyl, furan, thiophenyl, imidazolyl, oxazolyl, thiazolyl, pyrazolyl, isoxazolyl, isothiazolyl, 1,2,3-triazolyl, 1,2,3-thiadiazolyl, 1,3,4-thiadiazolyl, 1,2,3-oxadiazolyl, 1,3,4-oxadiazolyl, 1,2,4-triazolyl, tetrazolyl, pyridinyl, pyridazinyl, pyrimidinyl, pyrazinyl, 1,2,4-triazinyl, benzo[c][1,2,5]oxadiazolyl, benzo[c]isothiazolyl, benzo[c]isoxazolyl, benzo[d]imidazolyl, benzo[d]isothiazolyl, benzo[d]isoxazolyl, benzo[d]oxazol-2(3H)-onyl, benzo[d]oxazolyl, benzo[d]thiazolyl, indazolyl, indolyl, isobenzofuran-1(3H)-onyl, isochroman-1-only, pyrazolo[1,5-a]pyrimidinyl, pyrrolo[2,3-b]pyridinyl, pyrrolo[2,3-c]pyridinyl, pyrrolo[3,2-b]pyridinyl, and pyrrolo[3,2-c]pyridinyl; wherein each of said phenyl and said heterocyclyl is substituted with zero to 4 $R_d$;

each $R_3$ is independently H, $C_{1-3}$ alkyl, $C_{1-3}$ haloalkyl, $C_{1-3}$ hydroxyalkyl, $C_{3-6}$ cycloalkyl, ($C_{1-3}$ alkoxy)-($C_{1-3}$ alkylenyl), —C(O)OR$_e$, or —C(O)NR$_e$R$_e$;

each $R_4$ is independently H, $C_{1-3}$ alkyl, $C_{1-3}$ haloalkyl, $C_{1-3}$ hydroxyalkyl, $C_{3-6}$ cycloalkyl, ($C_{1-3}$ alkoxy)-($C_{1-3}$ alkylenyl), aryl, heteroaryl, —CO$_2$H, —CO$_2$R$_e$, —CONHR$_e$, —CONR$_e$R$_e$, or —NR$_{4a}$R$_{4a}$, wherein each of said cycloalkyl, aryl, and said heteroaryl is substituted with zero to 3 $R_d$;

each $R_{4a}$ is independently H, $C_{1-3}$ alkyl, $C_{1-3}$ fluoroalkyl, $C_{3-6}$ cycloalkyl, aryl, or heteroaryl, wherein each of said cycloalkyl, aryl, and said heteroaryl is substituted with zero to 3 $R_d$; or two $R_{4a}$ along with the nitrogen atom to which they are attached form a 3-7 membered heterocyclyl;

each $R_d$ is independently F, Cl, —OH, —CN, $C_{1-3}$ alkyl, $C_{1-3}$ fluoroalkyl, $C_{3-6}$ cycloalkyl, $C_{1-3}$ alkoxy, $C_{1-3}$ fluoroalkoxy, —C(O)OR$_e$, —C(O)NR$_e$R$_e$, —OC(O)NR$_e$R$_e$, —NHC(O)OR$_e$, —NR$_e$C(O)OR$_e$, or —S(O)$_2$R$_e$; and each $R_e$ is independently H, $C_{1-3}$ alkyl, $C_{1-3}$ fluoroalkyl, $C_{3-6}$ cycloalkyl, aryl, or heteroaryl; or two $R_e$ along with the nitrogen atom to which they are attached form a 3-7 membered heterocyclyl.

The second aspect of the present invention provides at least one compound of Formula (I) or a salt thereof, wherein X is CR$_4$ and Y is CR$_4$. Compounds of this aspect have the structure of Formula (Ia):

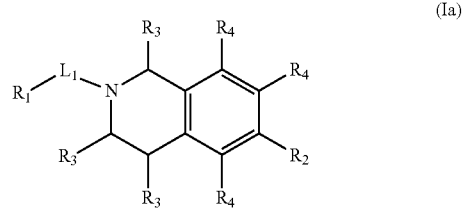

(Ia)

wherein $R_1$, $R_2$, $R_3$, $R_4$, and $L_1$ are defined in the first aspect.

The third aspect of the present invention provides at least one compound of Formula (I) or a salt thereof, wherein X is N and Y is $CR_4$. Compounds of this aspect have the structure of Formula (Ib):

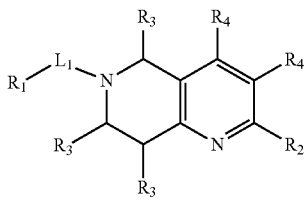
(Ib)

wherein $R_1$, $R_2$, $R_3$, $R_4$, and $L_1$ are defined in the first aspect.

The fourth aspect of the present invention provides at least one compound of Formula (I) or a salt thereof, wherein X is N and Y is N. Compounds of this aspect have the structure of Formula (Ic):

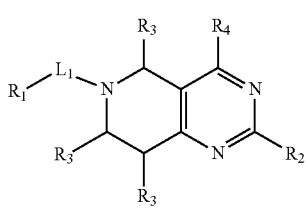
(Ic)

wherein $R_1$, $R_2$, $R_3$, $R_4$, and $L_1$ are defined in the first aspect.

One embodiment provides a compound of Formula (I) or a salt thereof, wherein:
$R_1$ is:

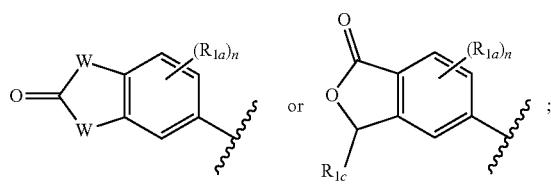

one W is $NR_{1b}$ and the other W is O; each $R_{1a}$ is independently selected from F, Cl, $C_{1-3}$ alkyl, $C_{1-3}$ fluoroalkyl, and $C_{3-6}$ cycloalkyl; $R_{1b}$ is H, $C_{1-3}$ alkyl, or $C_{1-3}$ fluoroalkyl; $R_{1c}$ is H, $C_{1-2}$ alkyl, or $C_{3-6}$ cycloalkyl; n is zero, 1, or 2; $R_a$ is H, F, —OH, $C_{1-2}$ alkyl, —$CF_3$, —$CH_2OH$, cyclopropyl, —$OCH_3$, or —$OCF_3$; $R_b$ is H, $C_{1-2}$ alkyl, or cyclopropyl; $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 3 $R_d$; $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; each $R_3$ is independently H, $C_{1-2}$ alkyl, $C_{1-2}$ fluoroalkyl, $C_{1-2}$ hydroxyalkyl, or $C_{3-6}$ cycloalkyl; each $R_4$ is independently H, —$CH_3$, —$CF_3$, cyclopropyl, phenyl, or —$NR_{4a}R_{4a}$; each $R_{4a}$ is independently H or —$CH_3$; each $R_d$ is independently F, Cl, —OH, —CN, $C_{1-2}$ alkyl, $C_{1-2}$ fluoroalkyl, $C_{3-6}$ cycloalkyl, $C_{1-2}$ alkoxy, —$OCF_3$, —$C(O)OR_e$, —$C(O)NR_eR_e$, —$OC(O)NR_eR_e$, —$NHC(O)OR_e$, —$NR_eC(O)OR_e$, or —$S(O)_2R_e$; each $R_e$ is independently H, —$CH_3$, —$CF_3$, or $C_{3-6}$ cycloalkyl; and X, Y, $L_1$, $L_2$, and $R_2$ are defined in the first aspect. Included in this embodiment are the compounds of Formula (Ia) in which X is $CR_4$ and Y is $CR_4$. Also included in this embodiment are the compounds of Formula (Ib) in which X is N and Y is $CR_4$. Other compounds included in this embodiment are the compounds of Formula (Ic) in which X is N and Y is N.

One embodiment provides a compound of Formula (I) or a salt thereof, wherein $R_1$ is:

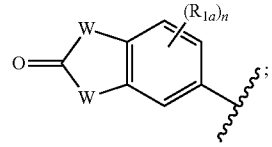

and X, Y, W, $R_2$, $R_3$, $R_4$, $L_1$ $R_{1a}$, and n are defined in the first aspect.

One embodiment provides a compound of Formula (I) or a salt thereof, wherein $R_1$ is:

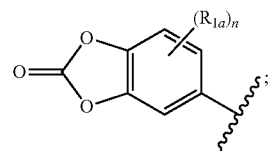

and X, Y, $R_2$, $R_3$, $R_4$, $L_1$ $R_{1a}$, and n are defined in the first aspect.

One embodiment provides a compound of Formula (I) or a salt thereof, wherein $R_1$ is:

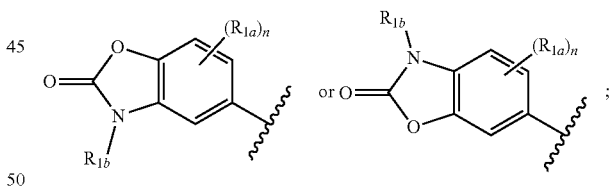

and X, Y, $R_2$, $R_3$, $R_4$, $L_1$ $R_{1a}$, $R_{1b}$, and n are defined in the first aspect.

One embodiment provides a compound of Formula (I) or a salt thereof, wherein $R_1$ is:

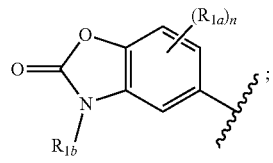

and X, Y, $R_2$, $R_3$, $R_4$, $L_1$ $R_{1a}$, $R_{1b}$, and n are defined in the first aspect.

One embodiment provides a compound of Formula (I) or a salt thereof, wherein $R_1$ is:

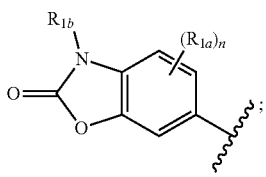

and X, Y, $R_2$, $R_3$, $R_4$, $L_1$ $R_{1a}$, $R_{1b}$, and n are defined in the first aspect.

One embodiment provides a compound of Formula (I) or a salt thereof, wherein $R_1$ is:

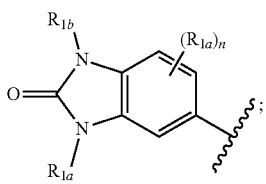

and X, Y, $R_2$, $R_3$, $R_4$, $L_1$ $R_{1a}$, $R_{1b}$, and n are defined in the first aspect.

One embodiment provides a compound of Formula (I) or a salt thereof, wherein $R_1$ is:

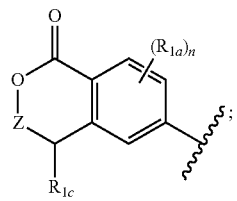

and X, Y, Z, $R_2$, $R_3$, $R_4$, $L_1$ $R_{1a}$, $R_{1c}$, and n are defined in the first aspect.

One embodiment provides a compound of Formula (I) or a salt thereof, wherein $R_1$ is:

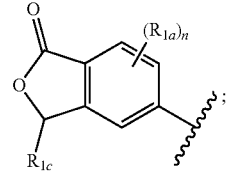

and X, Y, $R_2$, $R_3$, $R_4$, $L_1$ $R_{1a}$, $R_{1c}$, and n are defined in the first aspect. Included in this embodiment are compounds in which each $R_{1a}$ is independently selected from F, Cl, $C_{1-3}$ alkyl, $C_{1-3}$ fluoroalkyl, and $C_{3-6}$ cycloalkyl; and $R_{1c}$ is H, $C_{1-2}$ alkyl, or $C_{3-6}$ cycloalkyl. Also included in this embodiment are compounds in which each $R_{1a}$ is independently H or —$CH_3$; and $R_{1c}$ is H or —$CH_3$.

One embodiment provides a compound of Formula (I) or a salt thereof, wherein $R_1$ is:

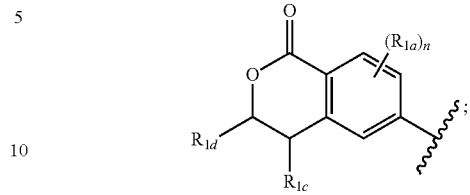

and X, Y, $R_2$, $R_3$, $R_4$, $L_1$ $R_{1a}$, $R_{1c}$, $R_{1d}$, and n are defined in the first aspect. Included in this embodiment are compounds in which each $R_{1a}$ is independently selected from F, Cl, $C_{1-3}$ alkyl, $C_{1-3}$ fluoroalkyl, and $C_{3-6}$ cycloalkyl; $R_{1l}$ is H, $C_{1-2}$ alkyl, or $C_{3-6}$ cycloalkyl; and $R_{1d}$ is H, $C_{1-2}$ alkyl, or $C_{3-6}$ cycloalkyl. Also included in this embodiment are compounds in which each $R_{1a}$ is independently H or —$CH_3$; $R_{1c}$ is H or —$CH_3$; and $R_{1d}$ is H, —$CH_3$, or —$OCH_3$.

One embodiment provides a compound of Formula (I) or a salt thereof, wherein $R_2$ is $R_{2a}$; and X, Y, $R_1$, $R_{2a}$, $R_3$, $R_4$, $R_d$, and $L_1$ are defined in the first aspect. Included in this embodiment are compounds in which $R_{2a}$ is a nitrogen-linked heterocyclyl selected from benzo[d]imidazolyl, imidazo[4,5-b]pyridinyl, imidazolyl, indazolyl, indolinyl, indolyl, pyrazolo[3,4-b]pyridinyl, pyrazolo[3,4-c]pyridinyl, pyrazolo[4,3-b]pyridinyl, pyrazolo[4,3-b]pyridinyl, pyrazolyl, pyrrolo[2,3-b]pyridinyl, pyrrolo[2,3-c]pyridinyl, and pyrrolo[3,2-b]pyridinyl, wherein each of said heterocyclyl is substituted with zero to 3 $R_d$. Also included are compounds in which $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 3 $R_d$.

One embodiment provides a compound of Formula (I) or a salt thereof, wherein $R_2$ is $R_{2a}$; X, Y, $R_1$, $R_{2a}$, $R_3$, $R_4$, $R_d$, and $L_1$ are defined in the first aspect; and $R_{2a}$ is heterocyclyl selected from

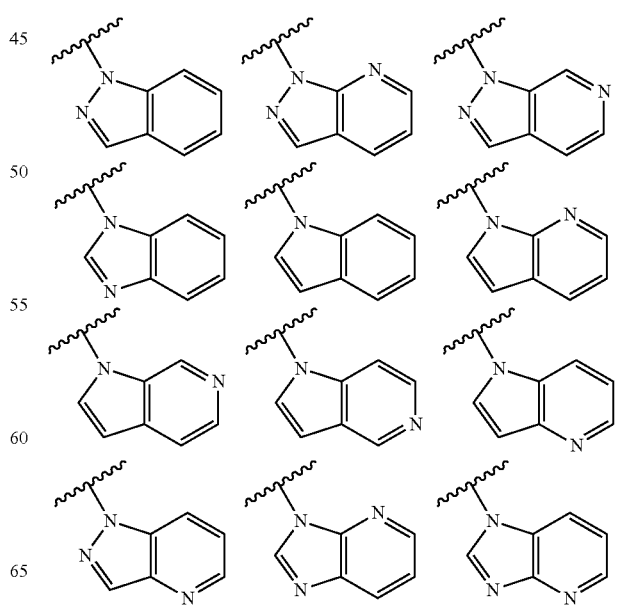

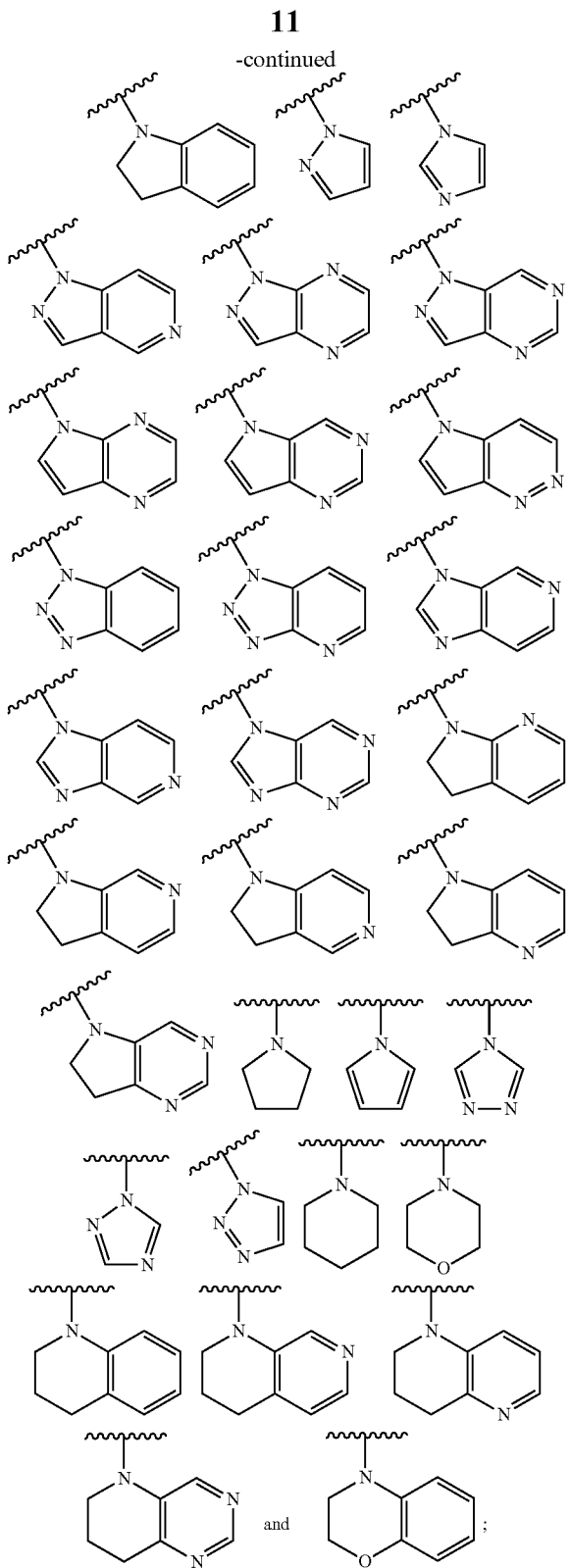

wherein each of said heterocyclyl is substituted with zero to 4 $R_d$.

One embodiment provides a compound of Formula (I) or a salt thereof, wherein $R_2$ is $R_{2a}$; X, Y, $R_1$, $R_{2a}$, $R_3$, $R_4$, $R_d$, and $L_1$ are defined in the first aspect; and $R_{2a}$ is a heterocyclyl selected from:

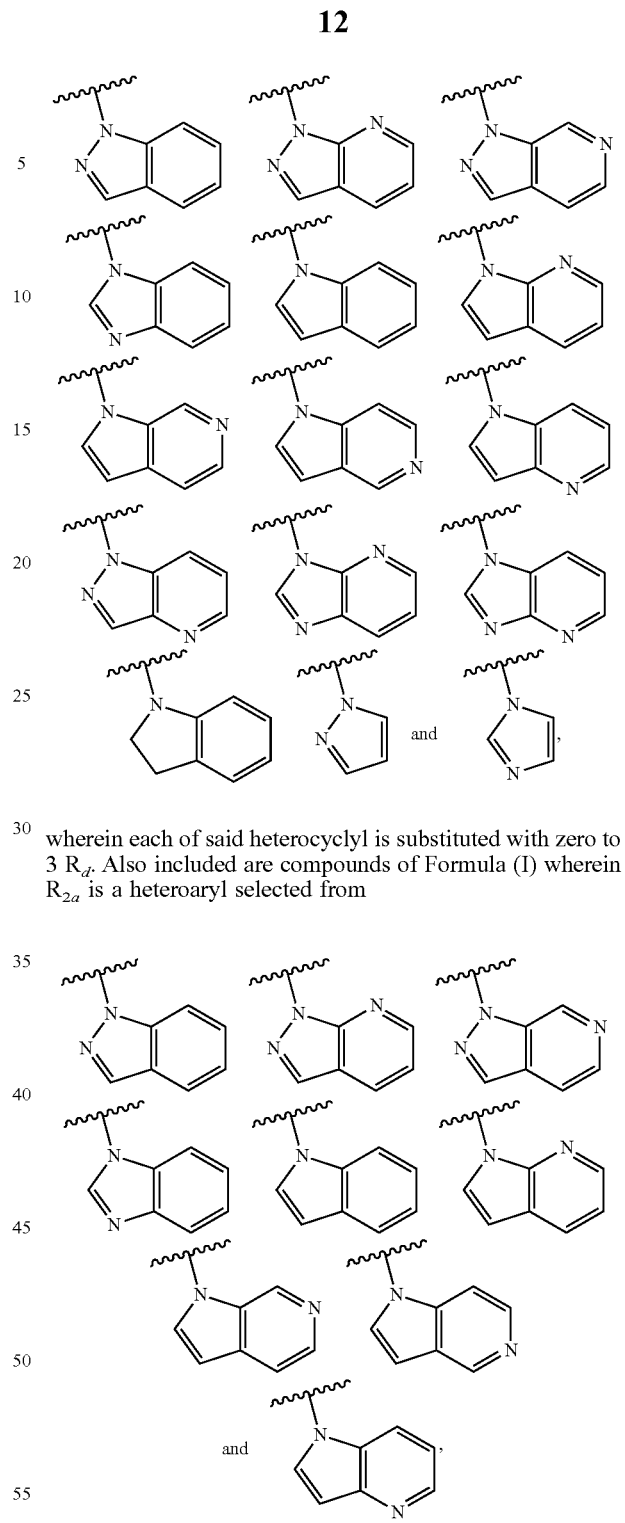

wherein each of said heterocyclyl is substituted with zero to 3 $R_d$. Also included are compounds of Formula (I) wherein $R_{2a}$ is a heteroaryl selected from wherein each of said heteroaryl is substituted with zero to 3 $R_d$.

One embodiment provides a compound of Formula (I) or a salt thereof, wherein $R_2$ is $R_{2a}$; and X, Y, $R_1$, $R_{2a}$, $R_3$, $R_4$, and $L_1$ are defined in the second aspect. Included in this embodiment are compounds in which $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]

pyridinyl, wherein each of said heteroaryl is substituted with zero to 3 $R_d$; and $R_d$ is defined in the first aspect.

One embodiment provides a compound of Formula (I) or a salt thereof, wherein $R_2$ is $R_{2a}$; and X, Y, $R_1$, $R_{2a}$, $R_3$, $R_4$, and $L_1$ are defined in the third aspect. Included in this embodiment are compounds in which $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 3 $R_d$; and $R_d$ is defined in the first aspect.

One embodiment provides a compound of Formula (I) or a salt thereof, wherein $R_2$ is $R_{2a}$; and X, Y, $R_1$, $R_{2a}$, $R_3$, $R_4$, and $L_1$ are defined in the fourth aspect. Included in this embodiment are compounds in which $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 3 $R_d$; and $R_d$ is defined in the first aspect.

One embodiment provides a compound of Formula (I) or a salt thereof, wherein $R_2$ is -$L_2$-$R_{2b}$; and X, Y, $R_1$, $R_{2b}$, $R_3$, $R_4$, $L_1$, and $L_2$ are defined in the first aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; and $R_d$ is defined in the first aspect.

One embodiment provides a compound of Formula (I) or a salt thereof, wherein $R_2$ is -$L_2$-$R_{2b}$; and X, Y, $R_1$, $R_{2b}$, $R_3$, $R_4$, $L_1$, and $L_2$ are defined in the second aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; and $R_d$ is defined in the first aspect.

One embodiment provides a compound of Formula (I) or a salt thereof, wherein $R_2$ is -$L_2$-$R_{2b}$; and X, Y, $R_1$, $R_{2b}$, $R_3$, $R_4$, $L_1$, and $L_2$ are defined in the third aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; and $R_d$ is defined in the first aspect.

One embodiment provides a compound of Formula (I) or a salt thereof, wherein $R_2$ is -$L_2$-$R_{2b}$; and X, Y, $R_1$, $R_{2b}$, $R_3$, $R_4$, $L_1$, and $L_2$ are defined in the fourth aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; and $R_d$ is defined in the first aspect.

One embodiment provides a compound of Formula (I) or a salt thereof, wherein $R_2$ is —$NR_cCH_2$—$R_{2b}$; and X, Y, $R_1$, $R_3$, $R_4$, and $L_1$ are defined in the first aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; and $R_d$ is defined in the first aspect.

One embodiment provides a compound of Formula (I) or a salt thereof, wherein $R_2$ is —$NR_cCH_2$—$R_{2b}$; and X, Y, $R_1$, $R_c$, $R_{2b}$, $R_3$, $R_4$, and $L_1$ are defined in the first aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$; and $R_d$ is defined in the first aspect. Also included in this embodiment are compounds in which $R_c$ is H, $C_{1-2}$ alkyl, $C_{1-2}$ fluoroalkyl, $C_{3-6}$ cycloalkyl, or ($C_{1-2}$ alkoxy)-($C_{1-2}$ alkylenyl). Additionally, included in this embodiment are compounds in which $R_c$ is H, —$CH_3$, —$CF_3$, or —$CH_2OCH_3$. Other compounds included in this embodiment are compounds in which $R_c$ is H or —$CH_3$.

One embodiment provides a compound of Formula (I) or a salt thereof, wherein $R_2$ is $R_{2a}$; $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 4 $R_d$; and X, Y, $R_1$, $R_3$, $R_4$, $L_1$, and $R_d$ are defined in the first aspect. Included in this embodiment are compounds in which $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 3 $R_d$. Also included in this embodiment are compounds in which $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 1 substituent selected from —CN.

One embodiment provides a compound of Formula (I) or a salt thereof, wherein $R_2$ is -$L_2$-$R_{2b}$; $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 4 $R_d$; and X, Y, $R_1$, $R_3$, $R_4$, $L_1$, $L_2$, and $R_d$ are defined in the first aspect. Included in this embodiment are compounds in which $R_{2b}$ is phenyl or a carbon-linked heteroaryl selected from pyridinyl, pyrimidinyl, isobenzofuranonyl, benzo[d]oxazolonyl, and pyrazolo[1,5-a] pyrimidinyl, wherein each of said phenyl and said heteroaryl is substituted with zero to 3 $R_d$. Also included in this embodiment are compounds in which $R_{2a}$ is a nitrogen-linked heteroaryl selected from benzo[d]imidazolyl, indazolyl, indolyl, pyrazolo[3,4-b] pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 1 substituent selected from —CN.

One embodiment provides a compound of Formula (I) or a salt thereof, wherein each $R_3$ is independently H, $C_{1-2}$ alkyl, $C_{1-2}$ fluoroalkyl, $C_{1-2}$ hydroxyalkyl, $C_{3-6}$ cycloalkyl, ($C_{1-2}$ alkoxy)-($C_{1-2}$ alkylenyl), —C(O)$OR_e$, or —C(O)$NR_eR_e$; each $R_e$ is independently H or —$CH_3$; and X, Y, $R_1$, $L_1$, $R_2$, and $R_4$ are defined in the first aspect. Included in this embodiment are compounds in which each $R_3$ is independently H, $C_{1-2}$ alkyl, $C_{1-2}$ fluoroalkyl, $C_{1-2}$ hydroxyalkyl, or $C_{3-6}$ cycloalkyl. Also included in this embodiment are compounds in which each $R_3$ is independently H, —$CH_3$, —$CF_3$, —$CH_2OH$, or cyclopropyl. Additionally, included in this embodiment are compounds in which each $R_3$ is H.

One embodiment provides a compound of Formula (I) or a salt thereof, wherein each $R_4$ is independently H, $C_{1-2}$ alkyl, $C_{1-2}$ haloalkyl, $C_{1-2}$ hydroxyalkyl, $C_{3-6}$ cycloalkyl, ($C_{1-2}$ alkoxy)-($C_{1-2}$ alkylenyl), phenyl, monocyclic heteroaryl, or —$NR_{4a}R_{4a}$, wherein each of said cycloalkyl, phenyl, and said heteroaryl is substituted with zero to 3 $R_d$; each $R_{4a}$ is independently H, $C_{1-2}$ alkyl, $C_{1-2}$ fluoroalkyl, $C_{3-6}$ cycloalkyl, phenyl, or monocyclic heteroaryl, wherein each of said cycloalkyl, phenyl, and said heteroaryl is substituted with zero to 3 $R_d$; each $R_d$ is F, Cl, —OH, —CN, $C_{1-2}$ alkyl, $C_{1-2}$ fluoroalkyl, $C_{3-6}$ cycloalkyl, $C_{1-2}$ alkoxy, $C_{1-2}$ fluoroalkoxy, —C(O)$OR_e$, —C(O)$NR_eR_e$, —OC(O)$NR_eR_e$, —NHC(O)$OR_e$, —$NR_eC(O)OR_e$, or —S(O)$_2R_e$; each $R_e$ is independently H, $C_{1-2}$ alkyl, $C_{1-2}$ fluoroalkyl, or $C_{3-6}$ cycloalkyl; and X, Y, $R_1$, $L_1$, $R_2$, and $R_3$ are defined in the first aspect. Included in this embodiment are compounds in which each $R_4$ is independently H, —$CH_3$, —$CF_3$, cyclopropyl, phenyl, or —$NR_{4a}R_{4a}$; each $R_{4a}$ is independently H or —$CH_3$; each $R_d$ is independently F, Cl, —OH, —CN, $C_{1-2}$ alkyl, $C_{1-2}$ fluoroalkyl, $C_{3-6}$ cycloalkyl, $C_{1-2}$ alkoxy, —$OCF_3$, —C(O)$OR_e$, —C(O)$NR_eR_e$, —OC(O)$NR_eR_e$, —NHC(O)$OR_e$, —$NR_eC(O)OR_e$, or —S(O)$_2R_e$; and each $R_e$ is independently H, —$CH_3$, —$CF_3$, or $C_{3-6}$ cycloalkyl. Also included in this embodiment are compounds in which each $R_4$ is H.

One embodiment provides a compound of Formula (I) or a salt thereof, wherein: $R_1$ is

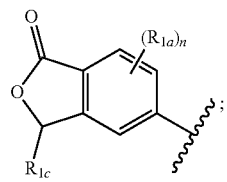

X is N; Y is N; and $L_1$, $R_{1a}$, $R_{1c}$, $R_2$, $R_3$, $R_4$ and n are defined in the first aspect. Included in this embodiment are compounds in which $R_2$ is $R_{2a}$; and $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 2 $R_d$; and each $R_d$ is independently F, Cl, —OH, —CN, —$CH_3$, or —$CF_3$. Also included in this embodiment are compounds in which $R_{1c}$ is H or —$CH_3$; n is zero; and $L_1$ is —$CH_2$— or —CH(OH)$CH_2$—.

One embodiment provides a compound of Formula (I) or a salt thereof, wherein: $R_1$ is

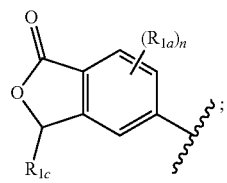

X is N; Y is N; $R_2$ is -$L_2$-$R_{2b}$; and $L_1$, $L_2$, $R_{1a}$, $R_{1c}$, $R_{2b}$, $R_3$, $R_4$ and n are defined in the first aspect. Included in this embodiment are compounds in which $R_{2b}$ is phenyl or a carbon-linked heteroaryl selected from pyridinyl, isobenzofuranonyl, and benzo[d]oxazolonyl, wherein each of said phenyl and said heteroaryl is substituted with zero to 2 $R_d$; and $R_d$ is F, Cl, —OH, —CN, —$CH_3$, or —$CF_3$. Also included in this embodiment are compounds in which $L_2$ is —NH— or —NH($CH_3$)—.

One embodiment provides a compound of Formula (I) or a salt thereof, wherein: $R_1$ is

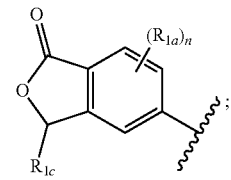

X is $CR_4$; Y is $CR_4$; and $L_1$, $R_{1a}$, $R_{1c}$, $R_2$, $R_3$, $R_4$ and n are defined in the first aspect. Included in this embodiment are compounds in which $R_2$ is -$L_2$-$R_{2b}$; $L_2$ is —NH— or —NHCH$_2$—; and $R_{2b}$ is phenyl or a carbon-linked heteroaryl selected from pyridinyl, pyrimidinyl, benzo[d]oxazolonyl, isobenzofuranonyl, and pyrazolo[1,5-a]pyrimidinyl, wherein each of said phenyl and said heteroaryl is substituted with zero to 2 $R_d$; and $R_d$ is F, Cl, —OH, —CN, —$CH_3$, or —$CF_3$. Also included in this embodiment are compounds in which $R_{2b}$ is phenyl substituted with F and —CN.

One embodiment provides a compound of Formula (I) or a salt thereof, wherein: $R_1$ is

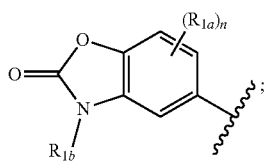

and X, Y, $R_2$, $R_3$, $R_4$, $L_1$ $R_{1a}$, $R_{1b}$, and n are defined in the first aspect. Included in this embodiment are compounds in which $R_{1b}$ is H or —$CH_3$; n is zero; and $L_1$ is —$CH_2$— or —CH(OH)$CH_2$—. Also included in this embodiment are compounds in which X is N; Y is N; $R_2$ is $R_{2a}$; $R_{2a}$ is a nitrogen-linked heteroaryl selected from indolyl and indazolyl, each substituted with —CN.

One embodiment provides a compound of Formula (I) or a salt thereof, wherein $R_1$ is

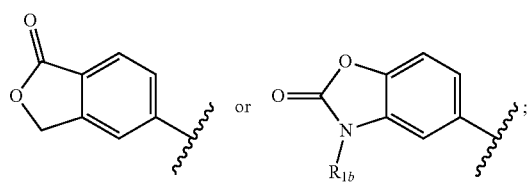

$R_{1b}$ is H or —$CH_3$; $L_1$ is a bond, —$CH_2$—, —$CH_2CH_2$—, —CH(CH$_2$OH)—, or —CH(OH)CH$_2$—; $L_2$ is —NH—, —N(CH$_3$)—, or —NHCH$_2$—; $R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 1 substituent selected from —CN; $R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 2 substituents independently selected from F, —CN, and —CH₃; each R₃ is H; each R₄ is H; and X, Y, and R₂ are defined in the first aspect.

One embodiment provides a compound of Formula (Ia) or a salt thereof, wherein said compound is 2-fluoro-4-((2-((1-oxo-1,3-dihydroisobenzofuran-5-yl)methyl)-1,2,3,4-tetrahydroisoquinolin-6-yl)amino)benzonitrile (4);

2-fluoro-4-((2-(2-(1-oxo-1,3-dihydroisobenzofuran-5-yl)ethyl)-1,2,3,4-tetrahydroisoquinolin-6-yl)amino)benzonitrile (6);

2-fluoro-4-(((2-(4-methyl-1-oxo-1,3-dihydroisobenzofuran-5-yl)-1,2,3,4-tetrahydroisoquinolin-6-yl)amino)methyl)benzonitrile (10);

3-methyl-5-((2-((4-methyl-1-oxo-1,3-dihydroisobenzofuran-5-yl)methyl)-1,2,3,4-tetrahydroisoquinolin-6-yl)amino)benzo[d]oxazol-2(3H)-one (14);

5-((6-((1-oxo-1,3-dihydroisobenzofuran-5-yl)amino)-3,4-dihydroisoquinolin-2(1H)-yl)methyl)isobenzofuran-1(3H)-one (15);

1-(2-((4-methyl-1-oxo-1,3-dihydroisobenzofuran-5-yl)methyl)-1,2,3,4-tetrahydroisoquinolin-6-yl)-1H-indole-4-carbonitrile (24);

2-fluoro-4-((2-((4-methyl-1-oxo-1,3-dihydroisobenzofuran-5-yl)methyl)-1,2,3,4-tetrahydroisoquinolin-6-yl)amino)benzonitrile (30);

2-fluoro-4-((2-(2-hydroxy-2-(4-methyl-1-oxo-1,3-dihydroisobenzofuran-5-yl)ethyl)-1,2,3,4-tetrahydroisoquinolin-6-yl)amino)benzonitrile (32);

2-fluoro-4-((2-(2-hydroxy-1-(4-methyl-1-oxo-1,3-dihydroisobenzofuran-5-yl)ethyl)-1,2,3,4-tetrahydroisoquinolin-6-yl)amino)benzonitrile (33);

4-methyl-6-((2-((1-oxo-1,3-dihydroisobenzofuran-5-yl)methyl)-1,2,3,4-tetrahydroisoquinolin-6-yl)amino)nicotinonitrile (34);

2-((2-((4-methyl-1-oxo-1,3-dihydroisobenzofuran-5-yl)methyl)-1,2,3,4-tetrahydroisoquinolin-6-yl)amino)pyrimidine-5-carbonitrile (37);

4-methyl-5-((6-(pyrazolo[1,5-a]pyrimidin-5-ylamino)-3,4-dihydroisoquinolin-2(1H)-yl)methyl)isobenzofuran-1(3H)-one (38);

2-fluoro-6-((2-((4-methyl-1-oxo-1,3-dihydroisobenzofuran-5-yl)methyl)-1,2,3,4-tetrahydroisoquinolin-6-yl)amino)benzonitrile (39); or 2-fluoro-4-((2-((3-methyl-2-oxo-2,3-dihydrobenzo[d]oxazol-5-yl)methyl)-1,2,3,4-tetrahydroisoquinolin-6-yl)amino)benzonitrile (48).

One embodiment provides a compound of Formula (Ib) or a salt thereof, wherein said compound is 2-fluoro-4-((6-(2-(1-oxo-1,3-dihydroisobenzofuran-5-yl)ethyl)-5,6,7,8-tetrahydro-1,6-naphthyridin-2-yl)amino)benzonitrile (7).

One embodiment provides a compound of Formula (Ic) or a salt thereof, wherein said compound is 1-(6-(2-hydroxy-2-(4-methyl-1-oxo-1,3-dihydroisobenzofuran-5-yl) ethyl)-5,6,7,8-tetrahydropyrido[4,3-d]pyrimidin-2-yl)-1H-indole-4-carbonitrile (1);

2-fluoro-5-((6-((1-oxo-1,3-dihydroisobenzofuran-5-yl)methyl)-5,6,7,8-tetrahydropyrido[4,3-d]pyrimidin-2-yl)amino)benzonitrile (2);

1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indazole-4-carbonitrile (3);

4-methyl-5-((2-((4-methyl-1-oxo-1,3-dihydroisobenzofuran-5-yl)amino)-7,8-dihydropyrido[4,3-d]pyrimidin-6(5H)-yl)methyl)isobenzofuran-1(3H)-one (5);

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile (8);

1-(6-(2-hydroxy-1-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile (9);

1-(6-((1-oxo-1,3-dihydroisobenzofuran-5-yl)methyl)-5,6,7,8-tetrahydropyrido[4,3-d]pyrimidin-2-yl)-1H-indazole-5-carbonitrile (11);

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-4-carbonitrile (12);

1-(6-((4-methyl-1-oxo-1,3-dihydroisobenzofuran-5-yl)methyl)-5,6,7,8-tetrahydropyrido[4,3-d]pyrimidin-2-yl)-1H-indazole-5-carbonitrile (13);

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-5-carbonitrile (16);

1-(6-(2-hydroxy-2-(1-oxo-1,3-dihydroisobenzofuran-5-yl)ethyl)-5,6,7,8-tetrahydropyrido[4,3-d]pyrimidin-2-yl)-1H-indole-5-carbonitrile (17);

1-(6-(2-hydroxy-2-(1-oxo-1,3-dihydroisobenzofuran-5-yl)ethyl)-5,6,7,8-tetrahydropyrido[4,3-d]pyrimidin-2-yl)-1H-indole-4-carbonitrile (18);

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-4-carbonitrile (19);

1-(6-((4-methyl-1-oxo-1,3-dihydroisobenzofuran-5-yl)methyl)-5,6,7,8-tetrahydropyrido[4,3-d]pyrimidin-2-yl)-1H-indole-4-carbonitrile (20);

1-(6-((4-methyl-1-oxo-1,3-dihydroisobenzofuran-5-yl)methyl)-5,6,7,8-tetrahydropyrido[4,3-d]pyrimidin-2-yl)-1H-indole-5-carbonitrile (21);

1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indole-4-carbonitrile (22);

1-(6-((4-methyl-1-oxo-1,3-dihydroisobenzofuran-5-yl)methyl)-5,6,7,8-tetrahydropyrido[4,3-d]pyrimidin-2-yl)-1H-indole-3-carbonitrile (23);

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-6-carbonitrile (25);

2-fluoro-4-((6-((4-methyl-1-oxo-1,3-dihydroisobenzofuran-5-yl)methyl)-5,6,7,8-tetrahydropyrido[4,3-d]pyrimidin-2-yl)amino)benzonitrile (26);

2-fluoro-4-((6-(2-(4-methyl-1-oxo-1,3-dihydroisobenzofuran-5-yl)ethyl)-5,6,7,8-tetrahydropyrido[4,3-d]pyrimidin-2-yl)amino)benzonitrile (27);

2-fluoro-4-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)benzonitrile (28);

2-fluoro-4-((6-(2-hydroxy-1-(4-methyl-1-oxo-1,3-dihydroisobenzofuran-5-yl)ethyl)-5,6,7,8-tetrahydropyrido[4,3-d]pyrimidin-2-yl)amino)benzonitrile (29);

4-methyl-6-((6-((4-methyl-1-oxo-1,3-dihydroisobenzofuran-5-yl)methyl)-5,6,7,8-tetrahydropyrido[4,3-d]pyrimidin-2-yl)amino)nicotinonitrile (31);

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-b]pyridine-4-carbonitrile (35);

5-(2-(2-(1H-pyrrolo[3,2-b]pyridin-1-yl)-7,8-dihydropyrido[4,3-d]pyrimidin-6(5H)-yl)-1-hydroxyethyl)-4-methyl-isobenzofuran-1(3H)-one (36);

1-(6-((4-methyl-1-oxo-1,3-dihydroisobenzofuran-5-yl)
methyl)-5,6,7,8-tetrahydropyrido[4,3-d]pyrimidin-2-yl)-
1H-benzo[d]imidazole-4-carbonitrile (40);
5-(2-(2-(1H-pyrazolo[4,3-b]pyridin-1-yl)-7,8-dihydro-
pyrido[4,3-d]pyrimidin-6(5H)-yl)-1-hydroxyethyl)-4-
methylisobenzofuran-1(3H)-one (41);
1-(6-(2-hydroxy-2-(4-methyl-1-oxo-1,3-dihydroisobenzo-
furan-5-yl)ethyl)-5,6,7,8-tetrahydropyrido[4,3-d]pyrimi-
din-2-yl)-1H-pyrrolo[2,3-c]pyridine-4-carbonitrile (42);
1-(6-(2-hydroxy-2-(4-methyl-1-oxo-1,3-dihydroisobenzo-
furan-5-yl)ethyl)-5,6,7,8-tetrahydropyrido[4,3-d]pyrimi-
din-2-yl)-1H-pyrazolo[3,4-c]pyridine-4-carbonitrile (43);
1-(6-(2-hydroxy-2-(4-methyl-1-oxo-1,3-dihydroisobenzo-
furan-5-yl)ethyl)-5,6,7,8-tetrahydropyrido[4,3-d]pyrimi-
din-2-yl)-1H-pyrrolo[2,3-b]pyridine-5-carbonitrile (44);
1-(6-(2-hydroxy-1-(4-methyl-1-oxo-1,3-dihydroisobenzo-
furan-5-yl)ethyl)-5,6,7,8-tetrahydropyrido[4,3-d]pyrimi-
din-2-yl)-1H-pyrrolo[2,3-b]pyridine-5-carbonitrile (45);
1-(6-((1-oxo-1,3-dihydroisobenzofuran-5-yl)methyl)-5,6,7,
8-tetrahydropyrido[4,3-d]pyrimidin-2-yl)-1H-pyrrolo[2,
3-b]pyridine-5-carbonitrile (46);
2-fluoro-4-(methyl(6-((4-methyl-1-oxo-1,3-dihydroisoben-
zofuran-5-yl)methyl)-5,6,7,8-tetrahydropyrido[4,3-d]py-
rimidin-2-yl)amino)benzonitrile (47);
3-methyl-5-((6-((4-methyl-1-oxo-1,3-dihydroisobenzo-
furan-5-yl)methyl)-5,6,7,8-tetrahydropyrido[4,3-d]py-
rimidin-2-yl)amino)benzo[d]oxazol-2(3H)-one (49); or
1-(6-(2-hydroxy-2-(4-methyl-1-oxo-1,3-dihydroisobenzo-
furan-5-yl)ethyl)-5,6,7,8-tetrahydropyrido[4,3-d]pyrimi-
din-2-yl)-1H-indazole-5-carbonitrile (50).

In another aspect, there are disclosed compounds of Formula (I), or compounds of Formula (I) as described by any of the other embodiments or aspects, including salts, enantiomers, diastereomers, tautomers, pharmaceutically-acceptable salts, hydrates, or solvates thereof, wherein: the compounds are selected from the Examples.

In another aspect, there is disclosed a pharmaceutical composition, comprising a pharmaceutically acceptable carrier and any one or more compounds of Formula (I), or compounds of Formula (I) as described by any of the other embodiments or aspects or examples, or a pharmaceutically acceptable salt thereof.

In another aspect, there is disclosed a method for the treatment of one or more diseases or disorders which can be modulated by inhibition of ROMK, comprising administering to a patient in need of such treatment or prophylaxis a therapeutically effective amount of at least one of the compounds of Formula (I), or compounds of Formula (I) as described by any of the other emodiments or aspects or examples, wherein the disease or disorder is treated by promotion of diuresis or natriuresis.

In another aspect, there is disclosed a method for the treatment or prophylaxis of one or more diseases or disorders which can be modulated by ROMK inhibition, wherein the compound of any of the embodiments is administered in combination with at least one other type of therapeutic agent.

In another aspect, there is disclosed a method for the treatment or prophylaxis of multiple diseases or disorders, comprising administering to a patient in need of such treatment or prophylaxis a therapeutically effective amount of at least one of the compounds of Formula (I), or compounds of Formula (I) as described by any of the other emodiments or aspects, wherein the disease or disorder is treated by the promotion of diuresis or natriuresis, or for ROMK associated disorders.

In another aspect, there is disclosed a method for the treatment or prophylaxis of diseases or disorders, wherein the compound of any of the embodiments is administered in combination with at least one other type of therapeutic agent. In another aspect, the present invention provides a compound selected from the exemplified examples or a stereoisomer, a tautomer, a pharmaceutically acceptable salt, or a solvate thereof.

In another aspect, the present invention provides a compound selected from any subset list of compounds within the scope of the examples.

In another aspect, the present invention provides treatment of hypertension or heart failure for patients in need of diuresis or natriuresis.

In another aspect, the present invention provides for the treatment of hypertension.

In another aspect, the present invention provides for the treatment of hypertension, idiopathic hypertension, regractory hypertension, and/or pulmonary hypertension.

In another aspect, the present invention provides for the treatment of heart failure.

In another aspect, the present invention provides for the treatment of edema, cardiac insufficiency, systolic heart failure, diastolic heart failure, diabetic heart filure, and/or acute-decompensated heart failure.

The present invention may be embodied in other specific forms without parting from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment.

Furthermore, any element of an embodiment is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I); and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "haloalkyl" as used herein is intended to include both branched and straight-chain saturated aliphatic hydrocarbon groups substituted with one or more halogen atoms. For example, "$C_{1-4}$ haloalkyl" is intended to include $C_1$, $C_2$, $C_3$, and $C_4$ alkyl groups substituted with one or more halogen atoms. Representative examples of haloalkyl groups include, but are not limited to, —CF$_3$, —CCl$_3$, —CFCl$_2$, and —CH$_2$CF$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and $C_{1-4}$ hydroxyalkyl.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "aryl" as used herein, refers to a group of atoms derived from a molecule containing aromatic ring(s) by removing one hydrogen that is bonded to the aromatic ring(s). Aryl groups that have two or more rings must include only aromatic rings. Representative examples of aryl groups include, but are not limited to, phenyl and naphthyl. The aryl ring may be unsubstituted or may contain one or more substituents as valence allows.

The term "benzyl," as used herein, refers to a methyl group in which one of the hydrogen atoms is replaced by a phenyl group. The phenyl ring may be unsubstituted or may contain one or more substituents as valence allows.

The term "heteroatom" refers to oxygen (O), sulfur (S), and nitrogen (N).

The terms "heterocyclyl" as used herein, refers to substituted and unsubstituted saturated, partially saturated, and aromatic 3- to 7-membered monocyclic groups, 7- to 11-membered bicyclic groups, and 10- to 15-membered tricyclic groups, in which at least one of the rings has at least one heteroatom (0, S or N), said heteroatom containing ring having 1, 2, 3, or 4 heteroatoms selected from O, S, and N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic and tricyclic groups may contain other heteroatoms or only carbon atoms; and may be saturated, partially saturated, or aromatic. The heterocyclo group may be attached at any available nitrogen or carbon atom in the heterocyclo group. The term "heterocyclyl" includes "heteroaryl" groups. As valence allows, if said further ring is cycloalkyl or heterocyclo it is additionally optionally substituted with =O (oxo).

The term "heteroaryl" refers to substituted and unsubstituted aromatic 5- or 6-membered monocyclic groups, 9- or 10-membered bicyclic groups, and 11- to 14-membered tricyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain other heteroatoms or only carbon atoms. The nitrogen and sulfur atoms may optionally be oxidized and the nitrogen atoms may optionally be quaternized. Bicyclic and tricyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The term "nitrogen-linked heterocyclyl" refers to substituted and unsubstituted heterocyclyl groups that include at least one nitrogen heteroatom and are attached by a bond to a nitrogen heteroatom in the heterocyclyl group.

The term "nitrogen-linked heteroaryl" refers to substituted and unsubstituted heteroaryl groups that include at least one nitrogen heteroatom and are attached by a bond to a nitrogen heteroatom in the heteroaryl group.

The term "carbon-linked heterocyclyl" refers to substituted and unsubstituted heterocyclyl groups that are attached by a bond to a carbon atom in the heterocyclyl group.

The term "carbon-linked heteroaryl" refers to substituted and unsubstituted heteroaryl groups that are attached by a bond to a carbon atom in the heteroaryl group.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to ROMK, or effective to treat or prevent cardiovascular disease.

In another aspect, there is disclosed a method for the treatment or prophylaxis of one or more disease or disorder which can be modulated by ROMK inhibition, comprising administering to a patient in need of such treatment or prophylaxis a therapeutically effective amount of at least one of the compounds of Formula (I), or compounds of Formula (I) as described by any of the other emodiments or aspects, wherein the disease or disorder is treated by the promotion of diuresis or natriuresis. In another aspect, there is disclosed a method for the treatment of one or more disease or disorder which can be treated by promotion of diuresis or natriuresis, wherein the cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, refractory hypertension cardiac insufficiency, nephrotic syndrome and acute kidney insufficiency.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—$CH_3$) also includes deuterated methyl groups such as —$CD_3$.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, *arachis* oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an anti-oxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and *arachis* oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutical compositions can be presented in a pack or dispenser device which can contain one or more unit dosage forms including the compound of Formula (I). The pack can, for example, comprise metal or plastic foil, such as a blister pack. The pack or dispenser device can be accompanied by instructions for administration.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The pharmaceutical compositions may contain other therapeutic agents and may be formulated, for example, by employing conventional solid or liquid vehicles or diluents, as well as pharmaceutical additives of a type appropriate to the mode of desired administration (e.g., excipients, binders, preservatives, stabilizers, and flavors) according to techniques such as those well known in the art of pharmaceutical formulation.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, and/or promote diuresis, and/or natriuresis. In another embodiment, the package insert states that the pharmaceutical composition can be used in combination (as defined previously) with a second therapeutic agent to treat cardiovascular disorder, and/or promote diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Utility

The compounds of the invention inhibit the activity of ROMK. Accordingly, compounds of Formula (I) have utility in treating conditions associated with the inhibition of ROMK.

The compounds described herein are intended for the treatment and/or prophylaxis of any disorders that benefit from increased excretion of water and sodium from the body, or for any patient in need of diuresis or natriuresis. Specific disorders would include any form of hypertension or heart failure (acute-decompensated and chronic, diastolic and systolic). For heart failure treatment, the compounds would be used to treat acute-decompensated heart failure to reduce edema and other symptoms and/or to overcome resistance to other classes of diuretics, or to shorten hospital stay. The compounds could also be used in heart failure after discharge from hospital or during chronic therapy to treat symptoms and reduce recurrences of acute-decompensations and hospital admissions. Other disorders for which a diuretic or natriuretic or both would have therapeutic or prophylactic benefit include post-operative volume overload, any edematous states including idiopathic edema, pulmonary hypertension including pulmonary arterial hypertension, cardiac insufficiency, nephrotic syndrome and acute kidney insufficiency.

The compounds in accordance with the present invention are beneficial in the treatment and/or prevention of various human ailments. The compounds in accordance with the present invention can be beneficial either as a stand alone therapy or in combination with other therapies that therapeutically could provide greater benefit. The ailments for which the compounds in the present invention could be of benefit include cardiovascular disease; and prophylaxis and/or treatment of diuresis or natriuresis.

One embodiment provides a method for treating cardiovascular disease. Particular, cardiovascular diseases include, but are not limited to, hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome and acute kidney insufficiency. For example, a therapeutically effective amount for treating a disorder may be administered in the method of the present embodiment.

One embodiment provides a method for the promotion of diuresis or natriuresis.

One or more additional pharmacologically active agents may be administered in combination with the compounds described herein including any other diuretic from any other diuretic class (thiazides, loops, potassium-sparing, osmotic, carbonic anhydrase inhibitors, mineralocorticoid receptor antagonists), acetylcholinesterase inhibitors, angiotensin receptor blockers, neutral endopeptidase inhibitors, dual angiotensin receptor antagonists and neutral endopeptidase inhibitors, aldosterone antagonists, natriuretic peptides, calcium channel blockers, relaxin or relaxin mimetics, inotropic agents, peripheral vasodilators, or mineralocorticoid receptor antagonists. One embodiment provides the compounds of Formula (I) for use in therapy. In the present embodiment, the use in therapy may include the administration of a therapeutically-effective amount of a compound of Formula (I).

The present invention also provides the use of the compounds of Formula (I) for the manufacture of a medicament for the treatment of cardiovascular disease. In the present embodiment, the use for the manufacture of a medicament may include the administration of a therapeutically-effective amount of a compound of Formula (I) for the treatment of cardiovascular disease.

The present invention also provides the use of the compounds of Formula (I) for the manufacture of a medicament for promotion of diuresis or natriuresis.

In one embodiment, the compounds of Formula (I) inhibit ROMK activity with $IC_{50}$ values of less than 10 µM, for example, from 0.001 to less than 10 µM, as measured by the Thallium Flux assay. Preferably, the compounds of Formula (I) inhibit ROMK activity with $IC_{50}$ values of less than 1 µM, for example, from 0.001 to less than 1 µM. Other preferred compounds inhibit ROMK activity with $IC_{50}$ values of 100 nM and less, for example, from 1 to 100 nM.

Examples of compounds of Formula (I) as specified in the "Examples" section below, have been tested in one or more of the assays described below.

Methods of Preparation

The compounds of the present invention may be synthesized by many methods available to those skilled in the art of organic chemistry. A compendium of synthetic methods which may be applicable to the preparation of compounds of the present invention may be found in Larock, R. C., *Comprehensive Organic Transformations*, VCH, New York (1989). General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. In the description of the synthetic methods described below, it is to be understood that all proposed reaction conditions, including choice of solvent, reaction atmosphere, reaction temperature, duration of the experiment and workup procedures, are typically chosen to be the conditions standard for that reaction, which should be readily recognized by one skilled in the art. Restrictions to the substituents that are compatible with the reaction conditions will be readily apparent to one skilled in the art and alternate methods must then be used. It will also be recognized that another major consideration in the planning of any synthetic route in this field is the judicious choice of the protecting group used for protection of the reactive functional groups present in the compounds. An authoritative account describing the many alternatives is Greene et al. (*Protective Groups in Organic Synthesis*, Wiley and Sons (1991)). Additionally, the various steps in the synthesis may be performed in an alternate sequence in order to give the desired compound or compounds. Examples of compounds of the present invention prepared by methods described in the general schemes are given in the preparations and examples section set out hereinafter. Preparation of homochiral examples may be carried out by techniques known to one skilled in the art. For example, homochiral compounds may be prepared by separation of racemic products by chiral phase preparative HPLC. Alternatively, the example compounds may be prepared by methods known to give enantiomerically enriched products.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

Compounds of general formula D, E, F may be synthesized according to Scheme 1.

SCHEME 1

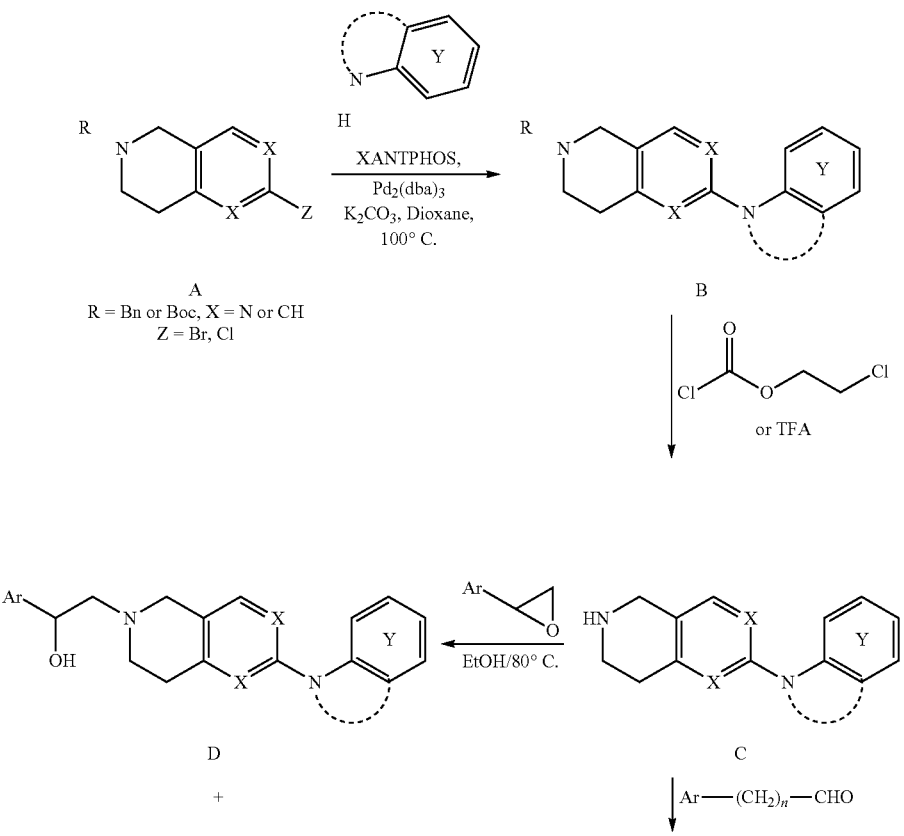

Compound A can be synthesized according to literature procedures. Compound A is subjected to Buchwald coupling reactions to install various substituted nitrogen-linked groups to yield B. Compound B is deprotected using choro-ethylchloroformate or TFA to yield compound C. Compound C is treated with epoxides, aldehydes or halomethylcarbonyl compounds followed by reduction to generate compounds of the general formula D, E and F.

Compounds of general formula J may be synthesized according to Scheme 2.

SCHEME 2

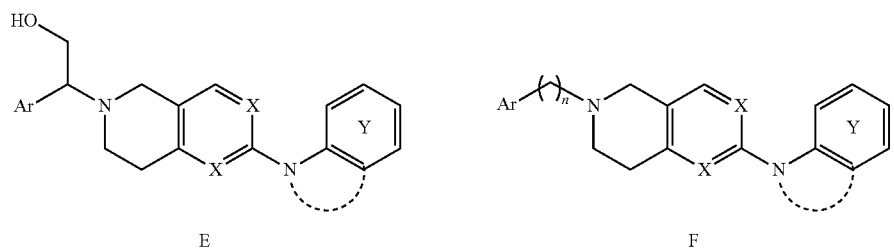

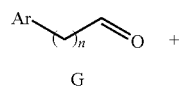

-continued

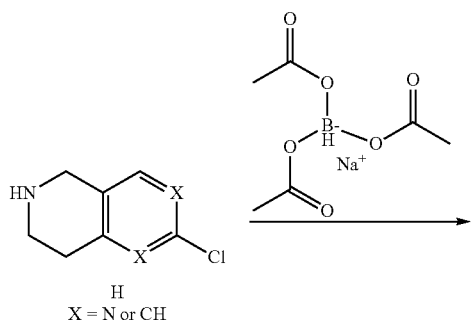

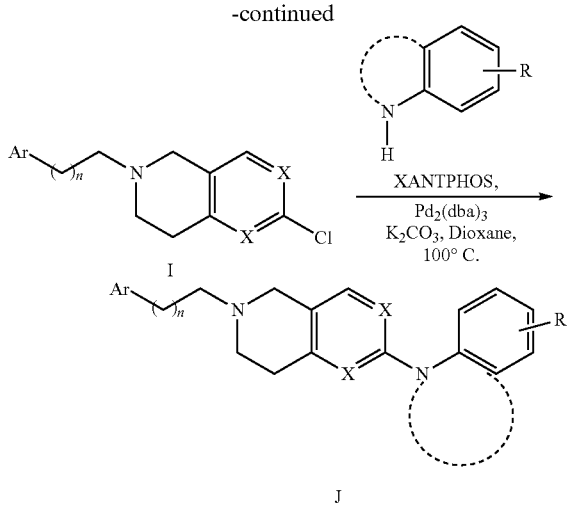

The substituted acetaldehyde (G) can be converted to (I) by reductive amination with compound H and sodium triacetoxyborohydride. Compound I is subjected to Buchwald coupling reactions to install various appropriately substituted nitrogen-linked groups to generate compounds of the general formula J.

Abbreviations

Ar aryl
ACN acetonitrile
Boc tert-butoxycarbonyl
$CH_2Cl_2$ dichloromethane
$CHCl_3$ chloroform
$CDCl_3$ deuterated chloroform
$CD_3OD$ deuterated methanol
DCM dichloromethane
DEA diethylamine
DMF N,N-dimethyl formamide
DMSO dimethyl sulfoxide
DMSO-$d_6$ deuterated dimethyl sulfoxide
Et ethyl
EtOAc ethyl acetate
EtOH ethanol
HCOOH formic acid
IPA isopropyl alcohol
$K_2CO_3$ potassium carbonate
Me methyl
MeOH methanol
$NaHCO_3$ sodium bicarbonate
$Na_2SO_4$ sodium sulfate
NBS N-bromosuccinimide
$NH_4OAc$ ammonium acetate
$Pd_2(dba)_3$ tris(dibenzylideneacetone)dipalladium (O)
$PdCl_2(dppf)CH_2Cl_2$ 1,1'-Bis(diphenylphosphino)ferrocene] dichloropalladium(II), complex with dichloromnethane
$POCl_3$ phosphorus oxychloride
TEA triethylamine
TFA trifluoroacetic acid
THF tetrahydrofuran
XANTPHOS 4,5-bis(diphenylphosphino)-9,9-dimethylxanthe
HPLC/MS High Pressure Liquid Chromatography-Mass Spectroscopy
LC Liquid Chromatography
min minute(s)
mmol millimole(s)
NMR nuclear magnetic resonance spectroscopy

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined above. Common intermediates are generally useful for the preparation of more than one Example and are identified sequentially (e.g., Intermediate 1, Intermediate 2, etc.) and are abbreviated as Int. 1, Int. 2, etc. Compounds of the Examples are identified by the example and step in which they were prepared (e.g., "1-A" denotes the Example 1, step A), or by the example only where the compound is the title compound of the example (for example, "1" denotes the title compound of Example 1). In some instances alternate preparations of intermediates or examples are described. Frequently chemists skilled in the art of synthesis may devise alternative preparations which may be desirable based on one or more considerations such as shorter reaction time, less expensive starting materials, ease of operation, amenable to catalysis, avoidance of toxic reagents, accessibility of specialized instrumentation, and decreased number of linear steps. The intent of describing alternative preparations is to further enable the preparation of the examples of this invention. In some instances some functional groups in the outlined examples and claims may be replaced by well known bioisosteric replacements known in the art, for example, replacement of a carboxylic acid group with a tetrazole or a phosphate moiety.

General Methods:

The following methods were used in the working Examples, except where noted otherwise.

Analytical HPLC and HPLC/MS Methods Employed in Characterization of Examples:

Reverse phase analytical HPLC/MS was performed on Shimadzu LC 10AS systems coupled with Waters ZMD Mass Spectrometers or Waters Aquity system coupled with a Waters Micromass ZQ Mass Spectrometer. Chiral analytical LC was performed on a Berger Analytical SFC instrument.

Method A: Ascentis Express C18 (2.1×50 mm) 2.7 μm particles; Solvent A: 95% water, 5% acetonitrile, 0.1% TFA; Solvent B: 95% acetonitrile, 5% water, 0.1% TFA; Temperature: 50° C.; Gradient: 0-100% B over 3 minutes, then a 1-minute hold at 100% B; Flow: 1.1 mL/min.

Method B: Ascentis Express C18 (2.1×50 mm) 2.7 μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 3 minutes, then a 1-minute hold at 100% B; Flow: 1.1 mL/min. UV 220 nm.

Method C: SunFire C18 column (4.6×150 mm) 3.5 am. Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm. UV 220 nm.

Method D: XBridge Phenyl column (4.6×150 mm) 3.5 m. Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method E: Kinetex, XB C18 (2.6 jam x 75.3 mm). Gradient elution (1.0 mL/min) from 20-100% Solvent B over 4 min and then 100% Solvent B for 0.6 min was used. Solvent A is 10 mM $NH_4CO_2H$ in 98% water, 2% acetonitrile and Solvent B is 10 mM $NH_4CO_2H$ in 2% water, 98% acetonitrile, UV 220 nm Method F: Ascentis Express C18 (2.1×50 mm) 2.7-μm particles; Solvent A: 95% water, 5% acetonitrile, 0.1% TFA; Solvent B: 95% acetonitrile, 5% water, 0.1% TFA; Temperature: 50° C.; Gradient: 0-100% B over 4 minutes, then a 1-minute hold at 100% B; Flow: 1.1 mL/min. UV 220 nm Method G: Ascentis Express C18 (2.1×50 mm) 2.7-μm particles; Solvent A: 95% water, 5% acetonitrile with 10 mM ammonium acetate; Solvent B: 95% acetonitrile, 5% water with 10 mM ammonium acetate; Temperature: 50° C.; Gradient: 0-100% B over 4 minutes, then a 1-minute hold at 100% B; Flow: 1.1 mL/min. UV 220 nm.

Method H: Sunfire C18 (3.0×150 mm) 3.5 am. Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method I: XBridge Phenyl C18 (3.0×150 mm) 3.5 am. Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method J: Sunfire C18 (3.0×150 mm) 3.5 am. Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method K: XBridge C18 (3.0×150 mm) 3.5 am. Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method L: Sunfire C18 (4.6×150 mm) 3.5 am. Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method M: XBridge Phenyl (4.6×150 mm) 3.5 m. Gradient elution (1.0 mL/min) from 10-100% Solvent B over 25 min and then 100% Solvent B for 5 min was used. Solvent A is 95% water, 5% acetonitrile, 0.05% TFA and Solvent B is 5% water, 95% acetonitrile, 0.05% TFA, UV 220 nm Method N: Sunfire C18 (4.6×150 mm) 3.5 m. Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method O: XBridge Phenyl (4.6×150 mm) 3.5 m. Gradient elution (1.0 mL/min) from 10-100% Solvent B over 18 min and then 100% Solvent B for 5 min was used. Solvent A is 95% water, 5% acetonitrile, 0.05% TFA and Solvent B is 5% water, 95% acetonitrile, 0.05% TFA, UV 220 nm.

Method P: Sunfire C18 (3.5 jam, 4.6×250 mm). Gradient elution (1.0 mL/min) from 10-100% Solvent B over 12 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method Q: Eclipse XDB-C18 column (4.6×150 mm). Gradient elution (1.0 mL/min) from 10-100% Solvent B over 7 min and then 100% Solvent B for 3 min was used. Solvent A is 95% water, 5% acetonitrile, 0.05% TFA and Solvent B is 5% water, 95% acetonitrile, 0.05% TFA, UV 220 nm.

Method R: Acquity BEH C8 (2.1×50 mm) 1.7 micron. Gradient elution (0.5 mL/min) from 20-90% Solvent B over 1.1 min then 90% Solvent B for 0.7 min was used. Solvent A: 95% water, 5% acetonitrile with 10 mM ammonium acetate; Solvent B: 95% acetonitrile, 5% water with 10 mM ammonium acetate; UV 220 nm.

Method S: Sunfire OBD (30×250 mm) 5 micron. Gradient elution (28 mL/min) from 30-100% Solvent B over 55 min. Solvent A: 10 mM Ammonium Acetate in $H_2O$, Solvent B: acetonitrile. UV 220 nm.

Method T: Acquity BEH C8 (2.1×50 mm) 1.7 micron. Gradient elution (0.5 mL/min) from 10-90% Solvent B over 1.1 min then 90% Solvent B for 0.6 min was used. Solvent A: 95% water, 5% acetonitrile with 0.1% TFA; Solvent B: 95% acetonitrile, 5% water with 0.1% TFA; UV 220 nm.

SFC and Chiral Purity Methods:

Method I: Chiralpak AD-H (250×4.6 mm) 5.0 am particles; % $CO_2$: 60%, % Co-solvent: 40% {0.2% DEA in IPA:ACN (1:1)}, Total Flow: 4.0 mL/min, Back pressure: 100 bars, Temperature: 25° C., UV: 218 nm.

Method II: Chiralpak OD-H (250×4.6 mm) 5.0 am particles; % $CO_2$: 60%, % Co-solvent: 40% {0.2% DEA in IPA:ACN (1:1)}, Total Flow: 4.0 mL/min, Back pressure: 104 bars, Temperature: 24.9° C., UV: 287 nm.

Method III: Chiralpak OJ-H (250×4.6 mm) 5.0 am particles; % $CO_2$: 60%, % Co-solvent: 30% (0.3% DEA in MeOH), Total Flow: 4.0 mL/min, Back pressure: 101 bars, Temperature: 23.6° C., UV: 272 nm.

Method IV: Chiralpak AS-H (250×4.6 mm) 5.0 am particles; % $CO_2$: 60%, % Co-solvent: 40% (0.3% DEA in MeOH), Total Flow: 4.0 mL/min, Back pressure: 102 bars, Temperature: 25.4° C., UV: 272 nm.

Method V: Chiralcel OJ-H (250×4.6 mm) 5.0 am particles; % $CO_2$: 60%, % Co-solvent: 40% (0.2% DEA in MeOH), Total Flow: 4.0 mL/min, Back pressure: 102 bars, Temperature: 24.6° C., UV: 272 nm.

Method VI: Luxcellulose-2 (250×4.6 mm) 5.0-μm particles; % $CO_2$: 60%, % Co-solvent: 35% (0.2% DEA in MeOH), Total Flow: 3.0 mL/min, Back pressure: 101 bars, Temperature: 23.6° C., UV: 260 nm.

Method VII: Chiralcel AS-H (250×4.6 mm) 5.0 jam particles; % $CO_2$: 60%, % Co-solvent: 40% (0.2% DEA in MeOH), Total Flow: 4.0 mL/min, Back pressure: 101 bars, Temperature: 24.4° C., UV: 270 nm.

Method VIII: Chiralpak IC (250×4.6 mm) 5.0 jam particles; % $CO_2$: 60%, % Co-solvent: 40% (0.2% DEA in EtOH), Total Flow: 4.0 mL/min, Back Pressure: 101 bars, Temperature: 24.4° C., UV: 270 nm.

Method IX: Chiralpak IF (250×4.6 mm) 5 micron; 0.2% DEA in n-hexane:EtOH:MeOH: 1:1:1, Flow: 1.0 mL/min, Temperature: 25° C., UV: 270 nm.

Method X: Lux Amylose 2 (250×4.6 mm) 5 micron; 0.2% DEA in n-hexane:EtOH: 5:95 Flow: 1.0 mL/min, Temperature: 25° C., UV: 270 nm.

Method XI: Chiralcel OD-H (250×4.6 mm) 5 micron; 0.2% DEA in n-hexane:EtOH: 70:30 Flow: 1.0, mL/min, Temperature: 25° C., UV: 260 nm.

Method XII: Chiralpack ID (250×4.6 mm) 5 micron; 0.1% DEA in MeOH, Flow: 1.0 mL/min, Temperature: 25° C., UV: 270 nm.

Method XIII: ChiralpackAD-H (250×4.6 mm) 5 micron; 0.1% DEA in n-hexane:EtOH: 70:30, Flow: 1.0 mL/min, Temperature: 25° C., UV: 270 nm.

Method XIV: Luxcellulose-2 (250×4.6 mm) 5.0 micron; % CO$_2$: 60%, % Co-solvent: 40% (0.2% DEA in n-hexane: EtOH: 80:20), Total Flow: 1.0 mL/min, Temperature: 25° C., UV: 260 nm Method XV: Chiralpak AD-H (250×4.6 mm) 5.0 micron. % CO$_2$: 60%, % Co-solvent: 40% (0.2% DEA in MeOH) Total Flow: 4.0 mL/min, Back Pressure: 100 bars, Temperature: 30° C., UV: 218 nm.

Method XVI: Chiralpak AD-H (250×4.6 mm) 5.0 micron. % CO$_2$: 60%, % Co-solvent: 40% (0.2% DEA in EtOH) Total Flow: 2.5 mL/min, Back pressure: 98 bars, Temperature: 15° C., UV: 218 nm.

Method XVII: Chiralpak ID (250×4.6 mm) 5 micron; 0.1% DEA in EtOH, Flow: 1.0 mL/min. Temperature: 25° C., UV: 254 nm Method XVIII: Chiralcell ADH (250×4.6 mm) 5 micron; 0.2% DEA in n-hexane:EtOH: 10:90, Flow: 1.0 mL\min, Temperature: 25° C., UV: 272 nm Method XIX: Chiralcel OJ-H (250×4.6 mm) 5.0 m particles; % CO$_2$: 60%, % Co-solvent: 40% (0.2% DEA in n-hexane: EtOH), Total Flow: 1.0 mL/min, Back pressure: 102 bars, Temperature: 24.6° C., UV: 272 nm.

Method XX: Chiralpak IE (250×4.6 mm) 5.0 m particles; 0.2% DEA in EtOH, Flow: 1.0 mL/min, Temperature: 25° C., UV: 220 nm Method XXI: Luxcellulose-4 (250×4.6 mm) 5.0 micron; % CO$_2$: 50%, % Co-solvent: 50% (0.2% DEA in IPA:ACN: 1:1), Total Flow: 4 mL/min, Temperature: 25° C., UV: 260 nm Method XXII: Chiralpak IC (250×4.6 mm) 5 micron; 0.1% DEA in EtOH, Flow: 1.0 mL/min, Temperature: 25° C., UV: 254 nm Method XXIII: Chiralpak IC (250×4.6 mm) 5 micron; 0.1% DEA in n-hexane: EtOH (50:50) Flow: 1.0 mL/min, Temperature: 25° C., UV: 260 nm Method XXIV: Chiralpak ID (250×4.6 mm) 5 micron; 0.2% TEA in n-hexane: EtOH (10:90) Flow: 1.0 mL/min, Temperature: 25° C., UV: 254 nm Method XXV: Chiralpak IA (250×4.6 mm) 5 micron; 0.2% DEA in n-hexane: IPA (5:95) Flow: 1.0 mL/min. Temperature: 25° C., UV: 254 nm Method XXVI: Chiralpak ADH (250×4.6 mm) 5 micron; 0.2% DEA in n-hexane: EtOH (5:95) Flow: 1.0 mL/min. Temperature: 25° C., UV: 254 nm Method XXVII: Chiralpak IA (250×4.6 mm) 5; 0.2% DEA in n-hexane: EtOH (10:90) Flow: 1.0 mL/min. Temperature: 25° C., UV: 254 nm NMR Employed in Characterization of Examples:

$^1$H NMR spectra were obtained with Bruker or JEOL Fourier transform spectrometers operating at frequencies as follows: $^1$H NMR: 400 MHz or 300 MHz (Bruker). $^{13}$C NMR: 100 MHz or 75 MHz (Bruker). Spectra data are reported in the format: chemical shift (multiplicity, coupling constants, and number of hydrogens). Chemical shifts are specified in ppm downfield of a tetramethylsilane internal standard (δ units, tetramethylsilane=0 ppm) and/or referenced to solvent peaks, which in $^1$H NMR spectra appear at 2.49 ppm for CD$_2$HSOCD$_3$, 3.30 ppm for CD$_2$HOD, and 7.24 ppm for CHCl$_3$, and which in $^{13}$C NMR spectra appear at 39.7 ppm for CD$_3$SOCD$_3$, 49.0 ppm for CD$_3$OD, and 77.0 ppm for CDCl$_3$. All $^{13}$C NMR spectra were proton decoupled.

Intermediates I-1-I and I-1-II

4-Methyl-5-(oxiran-2-yl)isobenzofuran-1(3H)-one

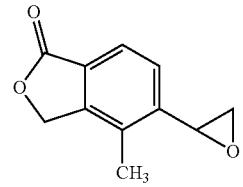

(Enantiomer I (I-1-I))

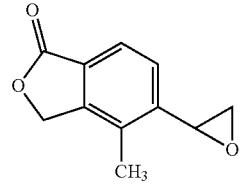

(Enantiomer II (I-1-II))

The two enantiomers were synthesized according to procedures disclosed in WO 2010/129379.

Intermediate I-2 tert-butyl 2-amino-7,8-dihydropyrido[4,3-d]pyrimidine-6(5H)-carboxylate

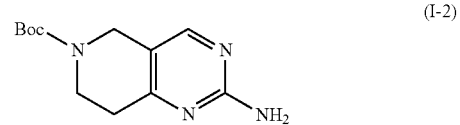 [SMILES: CC(C)(C)OC(=O)N1CCc2nc(N)ncc2C1]

(I-2)

Intermediate I-2 was synthesized according to procedures disclosed in WO 2014/089324.

Intermediate I-3

1-oxo-1,3-dihydroisobenzofuran-5-carbaldehyde

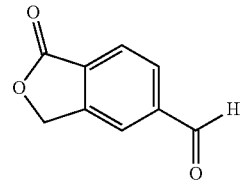

(I-3)

Intermediate I-3A: 5-vinylisobenzofuran-1(3H)-one

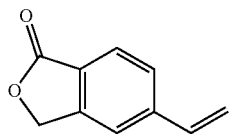
(I-3A)

5-bromoisobenzofuran-1(3H)-one (5.00 g, 23.5 mmol) was combined with potassium vinyltrifluoroborate (4.72 g, 35.2 mmol), PdCl$_2$(dppf)CH$_2$Cl$_2$ (1.91 g, 2.35 mmol) and TEA (6.54 mL, 46.9 mmol) in ethanol (50 mL). The reaction mixture was purged with nitrogen gas and stirred at 85° C. for 16 h. The reaction mixture was cooled to room temperature, diluted with water and extracted with EtOAc (3×50 mL). The combined extracts were washed with brine (30 mL), dried over sodium sulfate and concentrated under reduced pressure. The crude was purified by column chromatography using CombiFlash (Redisep-40 g, 15% EtOAc in n-hexane) to give Intermediate I-3A (3.60 g, 83.0%) as an off white solid. $^1$H NMR (300 MHz, DMSO-d$_6$) δ ppm 5.41 (s, 2H), 5.49 (d, J=10.9 Hz, 1H), 6.07 (d, J=17.4 Hz, 1H), 6.90 (dd, J=17.8, 10.9 Hz, 1H), 7.65-7.72 (m, 1H), 7.76 (s, 1H), 7.78-7.86 (m, 1H). LCMS (Method R), retention time: 0.64 min, (M+H) 161.1.

Intermediate I-3

Intermediate I-3A (3.60 g, 22.5 mmol) was dissolved in a mixture of MeOH: THF/1:1 (60 mL) and was cooled to −78° C. Ozone gas was bubbled through the solution until the color of the reaction mixture changed to orange. Residual ozone was removed by nitrogen gas bubbling through the reaction mixture for about one minute. Dimethyl sulfide (4.99 mL, 67.4 mmol) was added to the reaction mixture, allowed to warm to ambient temperature and stirred for 2 h. The volatiles were removed under vacuum and the crude material was purified by column chromatography using CombiFlash (Redisep-40 g, 40% EtOAc in n-hexane) to give Intermediate I-3 (1.70 g, 46.6%) as an off-white solid. $^1$H NMR (300 MHz, DMSO-d$_6$) δ ppm 5.52 (s, 2H), 8.04-8.12 (m, 2H), 8.20 (s, 1H), 10.18 (s, 1H). LCMS (method E), retention time 0.92 min, [M+H] 162.9.

Intermediate I-4

5-bromo-3-methylbenzo[d]oxazol-2(3H)-one

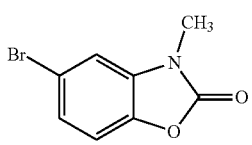
(I-4)

Intermediate I-4 was synthesized according to the procedures disclosed in WO 2010/130773.

Intermediate I-5

1H-indazole-5-carbonitrile

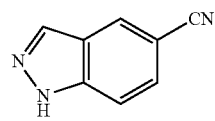
(I-5)

Intermediate I-5 was synthesized according to the procedures disclosed in WO 2014/0171432.

Intermediate I-6

1H-indazole-4-carbonitrile

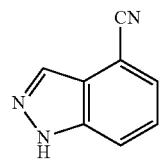
(I-6)

Intermediate I-6 was synthesized according to the procedures disclosed in WO 2013/026914.

Intermediate I-7

1H-pyrrolo[2,3-b]pyridine-4-carbonitrile

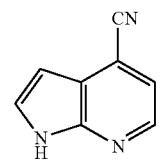
(I-7)

Intermediate I-7 was synthesized according to the procedures disclosed in WO 2014073904.

Intermediate I-8

1H-pyrazolo[4,3-b]pyridine

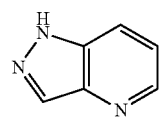
(I-8)

Intermediate I-8 was synthesized according to the procedures disclosed in WO 2008/071451.

Intermediate I-9

1H-pyrrolo[2,3-c]pyridine-4-carbonitrile

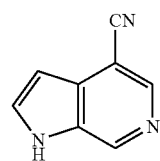
(I-9)

Intermediate I-9 was synthesized according to the procedures disclosed in WO 2013/092940.

Intermediate I-10

1H-pyrazolo[3,4-c]pyridine-4-carbonitrile

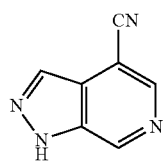
(I-10)

To a stirred solution of 4-bromo-1H-pyrazolo[3,4-c]pyridine (0.320 g, 1.62 mmol) in DMF (10 mL) were added Zn(CN)$_2$ (0.190 g, 1.62 mmol) and ZnCl$_2$ (0.110 g, 0.808 mmol). The resulting reaction mixture was degassed with nitrogen for 5 minutes and tetrakis(triphenylphosphine)palladium(O) (0.373 g, 0.323 mmol) was added and again degassed with nitrogen for 5 minutes. The reaction mixture was heated in a sealed tube at 100° C. for 10 h. The reaction mixture was cooled and concentrated under reduced pressure, diluted with water (40 mL) and extracted with EtOAc (2×20 mL). The combined organic layer was dried over anhydrous sodium sulfate, filtered and concentrated under reduced pressure. The resulting residue was purified by CombiFlash (Redisep-24 g, 70% EtOAc/n-hexanes), to obtain Intermediate I-10 (0.14 g, 60%). $^1$H NMR (400 MHz, DMSO-d$_6$) δ ppm 8.50 (s, 1H), 8.75 (s, 1H), 9.38 (s, 1H), 14.32 (br, s, 1H). LCMS (method E), retention time 0.647 min, [M+H] 145.0.

Intermediate I-11

Pyrazolo[1,5-a]pyrimidin-5-amine

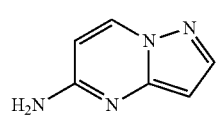
(I-11)

Intermediate I-11 was synthesized according to the procedures disclosed in WO 2014/074657.

Intermediate I-12

4-methyl-1-oxo-1,3-dihydroisobenzofuran-5-carbaldehyde

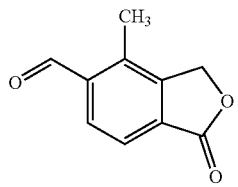
(I-12)

Intermediate I-12 was synthesized according to the procedures disclosed in WO 2015/095097.

Intermediate I-13

2-(1-oxo-1,3-dihydroisobenzofuran-5-yl)acetaldehyde

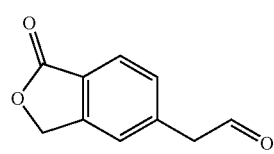
(I-13)

Intermediate I-13 was synthesized according to the procedures disclosed in WO 2012/058134 A1, 2012.

Intermediate I-14

1H-pyrazolo[3,4-b]pyridine-4-carbonitrile

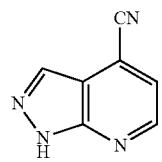
(I-14)

Intermediate I-14 was synthesized according to the procedures disclosed in WO 2007/48070 A2, 2007.

Intermediate I-15

1H-indole-3-carbonitrile

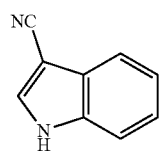
(I-15)

Intermediate I-15 was synthesized according to the procedures disclosed in *Tetrahedron* 69 (2013) 4236-4240.

Intermediate I-16

6-benzyl-2-chloro-5,6,7,8-tetrahydro-1,6-naphthyridine

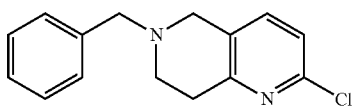
(I-16)

Intermediate I-16 was synthesized according to the procedures disclosed in WO 2007/52124.

Intermediate I-17

4-(bromomethyl)-2-fluorobenzonitrile

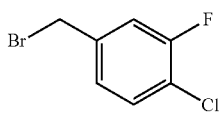
(I-18)

Intermediate I-18 was synthesized according to the procedures disclosed in *Organic and Biomolecular Chemistry*, 2, (2004) 1339-1352.

Intermediate I-19

6-benzyl-2-chloro-5,6,7,8-tetrahydropyrido[4,3-d]pyrimidine

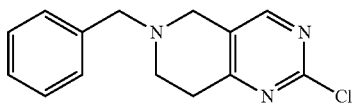
(I-19)

Intermediate I-19A: 6-benzyl-5,6,7,8-tetrahydropyrido[4,3-d]pyrimidine-2,4-diol

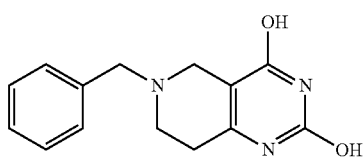
(I-19A)

Methyl 1-benzyl-4-oxopiperidine-3-carboxylate (10.0 g, 40.4 mmol) and urea (4.86 g, 81.0 mmol) were dissolved in ethanol (35 mL), and a 1 M solution of sodium methoxide (20 mL, 20.0 mmol) in methanol was added dropwise. The resulting reaction mixture was heated to reflux under nitrogen atmosphere for 24 h. The reaction mixture was cooled to 0° C. for 15 min and the resulting crystals were isolated by suction filtration. The crystals were suspended in water and hydrochloric acid was added so as to adjust the pH to 6.0. This mixture was stirred at room temperature for 1 h and the resulting crystals were isolated by suction filtration and dried under vacuum to obtain Intermediate I-19A (5.20 g, 50.1%), which was used without further purification. $^1$H NMR (400 MHz, DMSO-$d_6$) δ 2.27 (t, J=5.5 Hz, 2H), 2.53-2.59 (m, 2H), 2.98 (s, 2H), 3.57 (s, 2H), 5.42 (br s, 2H), 7.23-7.37 (m, 5H). LCMS (Method R): retention time 0.67 min, [M+H] 258.4.

Intermediate I-19B: 6-benzyl-2,4-dichloro-5,6,7,8-tetrahydropyrido[4,3-d]pyrimidine

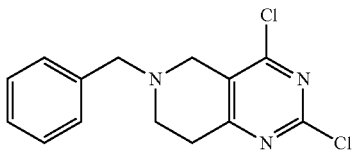
(I-19B)

POCl$_3$ (25 mL, 268 mmol) was slowly added over a period of 15 min into a flask containing Intermediate 19A (5.00 g, 19.4 mmol). The resulting reaction mixture was heated to 100° C. for 16 h then concentrated completely. The residue was quenched with ice water and basified to pH 8 with saturated sodium bicarbonate solution. The aqueous mixture was extracted with DCM (3×200 mL) and the combined organic layer was dried over anhydrous sodium sulfate, filtered and concentrated under reduced pressure. The residue was purified by silica gel column chromatography using CombiFlash (Redisep-40 g column and 25-30% EtOAc in hexane) to afford Intermediate I-19B (3.20 g, 56.0%) as a yellow solid. $^1$H NMR (400 MHz, CDCl$_3$) δ 2.77-2.84 (m, 2H), 2.95-3.04 (m, 2H), 3.63 (s, 2H), 3.77 (s, 2H), 7.27-7.40 (m, 5H). LCMS (Method E): retention time 3.02 min, [M+H] 294.0.

Intermediate I-19

To a solution of Intermediate I-19B (3.00 g, 10.20 mmol) in ethanol (60 mL) was added zinc (3.33 g, 51.0 mmol) and ammonium hydroxide (2.00 mL, 51.4 mmol). The resulting reaction mixture was heated to 75° C. for 15 h then was cooled, filtered through celite, and washed with ethyl acetate (20 mL). The filtrate was extracted with ethyl acetate (3×50 mL) and the combined organic phase was dried over anhydrous sodium sulfate and filtered. The filtrate was concentrated under reduced pressure. The residue was purified by silica gel column chromatography using CombiFlash (Redisep-24 g, 40-50% EtOAc in pet ether) to afford Intermediate I-19 (1.30 g, 49.1%) as a yellow gum. $^1$H NMR (400 MHz, CDCl$_3$) δ 2.80-2.90 (m, 2H), 2.97-3.05 (m, 2H), 3.58 (d, J=1.0 Hz, 2H), 3.73 (s, 2H), 7.28-7.42 (m, 5H), 8.23 (s, 1H). LCMS (Method E): retention time 2.24 min, [M+H] 260.1.

Intermediate I-20 tert-butyl 2-bromo-7,8-dihydropyrido[4,3-d]pyrimidine-6(5H)-carboxylate

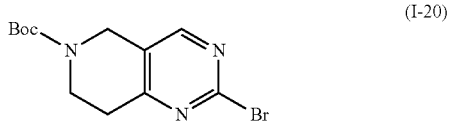 [SMILES: CC(C)(C)OC(=O)N1CCc2nc(Br)ncc2C1]
(I-20)

To a stirred solution of CuBr$_2$ (6.69 g, 30.0 mmol) in acetonitrile (3 mL) at 0° C., was added isoamyl nitrite (26.9 mL, 200 mmol) and stirring was continued for 20 min. To this resulting reaction mixture was added Intermediate I-2 (5.00 g, 19.9 mmol) and was allowed to warm to ambient temperature. After 3 h, the reaction was quenched with water (10 mL) and extracted with ethyl acetate (3×250 mL). The combined organic extracts were dried over anhydrous Na$_2$SO$_4$, filtered and concentrated under reduced pressure. The residue was purified by CombiFlash (Redisep-40 g, 35% EtOAc/n-hexanes) to obtain Intermediate I-20 (1.50 g, 23.9%), as a colorless liquid. $^1$H NMR (400 MHz, DMSO-d$_6$) δ ppm 1.43 (s, 9H) 2.87 (t, J=6.0 Hz, 2H) 3.64 (t, J=6.0 Hz, 2H) 4.53 (s, 2H) 8.56 (s, 1H). LCMS (Method E): retention time 2.08 min, [M+H] 316.2.

Intermediate I-21

5-(2-bromoacetyl)-3-methylbenzo[d]oxazol-2(3H)-one

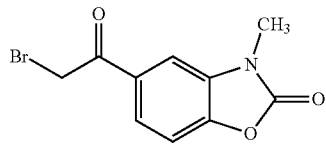
(I-21)

Intermediate I-21A: 5-(1-ethoxyvinyl)-3-methylbenzo[d]oxazol-2(3H)-one

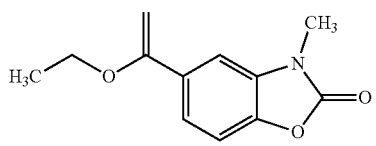
(I-21A)

A solution of Intermediate I-4 (4.00 g, 17.4 mmol), tributyl(1-ethoxyvinyl)tin (7.05 mL, 20.8 mmol) and LiCl (1.47 g, 34.8 mmol) in toluene (30 mL), was degassed with nitrogen for 15 minutes and tetrakis(triphenylphosphine) palladium (0.603 g, 0.522 mmol) was added. The resulting reaction mixture was degassed with nitrogen for another 5 minutes and was heated to 100° C. for 16 h. The reaction mixture was then cooled, diluted with water (40 mL) and extracted with ethyl acetate (3×100 mL). The combined organic layers were washed with brine (50 mL), dried over sodium sulfate, filtered and concentrated under reduced pressure to obtain Intermediate I-21A (5.50 g, 70.0%). LCMS (Method E): Retention time 2.50 min, [M+H] 221. The compound was taken forward directly to the subsequent step without further purification or characterization.

Intermediate I-21

To a solution of Intermediate I-21A (5.50 g, 12.5 mmol) in dioxane (50 mL) and H$_2$O (15 mL) at 0° C. was added NBS (2.68 g, 15.0 mmol) portion wise. The resulting reaction mixture was stirred for 1 h at ambient temperature, then diluted with water (50 mL) and extracted with ethyl acetate (3×100 mL). The combined organic layers were washed with brine (50 mL), dried over sodium sulphate, and evaporated under reduced pressure. The residue was purified by CombiFlash (Redisep-40 g, 50% EtOAc/n-Hexanes), to afford Intermediate I-21 (5.00 g, 73.8%) as a brown solid. $^1$H NMR (400 MHz, CDCl$_3$) δ ppm 3.45 (s, 3H), 4.44 (s, 2H), 7.28 (d, J=8.0 Hz, 1H), 7.67 (d, J=1.6 Hz, 1H), 7.82 (dd, J=8.0 Hz, J=1.6 Hz, 1H). LCMS (Method R): retention time 0.99 min, [M–H] 268.

Intermediate I-22 tert-butyl 6-bromo-3,4-dihydroisoquinoline-2(1H)-carboxylate

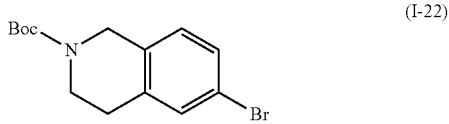 [SMILES: CC(C)(C)OC(=O)N1CCc2cc(Br)ccc2C1]
(I-22)

To a solution of 6-bromo-1,2,3,4-tetrahydroisoquinoline (1.00 g, 4.72 mmol) in DCM (20 mL) was added TEA (1.314 mL, 9.43 mmol) followed by di-tertbutyl dicarbonate (1.31 mL, 5.66 mmol) and the reaction mixture was stirred at ambient temperature for 12 h. The reaction was quenched with water and extracted with DCM (2×50 mL). The combined organic layer was dried over anhydrous sodium sulfate, and concentrated under reduced pressure. The crude was purified by CombiFlash (Redisep-12 g, 15% EtOAc/n-hexanes) to obtain Intermediate I-22 (1.10 g, 74.7%), as a light brown liquid. $^1$H NMR (300 MHz, DMSO-d$_6$) δ ppm 1.42 (s, 9H), 2.77 (t, J=5.85 Hz, 2H), 3.52 (t, J=5.85 Hz, 2H), 4.45 (s, 2H), 7.14 (d, J=7.93 Hz, 1H), 7.33-7.40 (m, 2H). LCMS (Method E): retention time 3.41 min, [M+H] 316.0.

Intermediate I-23

2-chloro-5,6,7,8-tetrahydro-1,6-naphthyridine

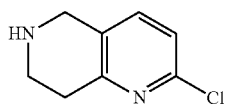
(I-23)

A mixture of Intermediate I-16 (0.475 g, 1.84 mmol) and 1-chloroethyl chloroformate (0.240 mL, 2.203 mmol) were dissolved in DCE (20 mL) and refluxed for 3 h. The reaction mixture was concentrated under reduced pressure and the residue was re-dissolved in MeOH (20 mL) and refluxed for 30 min. The reaction mixture was cooled and concentrated under reduced pressure. The residue was redissolved in water and washed with EtOAc (3×30 mL). The aqueous layer was basified with 10% sodium bicarbonate solution (100 mL) and extracted with DCM (2×50 mL). The combined DCM layer was washed with brine, dried over anhydrous $Na_2SO_4$, filtered and concentrated under reduced pressure. The crude was purified by CombiFlash (Redisep-12 g, 2% MeOH in chloroform) to obtain Intermediate I-23 (0.300 g 79%) as a brown solid. $^1$H NMR (300 MHz, DMSO-$d_6$) δ ppm 3.07 (t, J=6.2 Hz, 2H), 3.47 (br s, 2H), 4.31 (br s, 2H), 7.44 (d, J=8.3 Hz, 1H), 7.75 (d, J=8.3 Hz, 1H), 9.46 (br s, 1H). LCMS (Method B): retention time 0.57 min, [M−1] 174.9.

Intermediate I-25

5-bromo-4-methylisobenzofuran-1(3H)-one

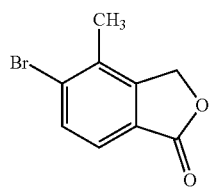

(I-25)

Intermediate I-25 was synthesized according to the procedures disclosed in WO 2015/095097.

Intermediate I-26

3-methyl-2-oxo-2,3-dihydrobenzo[d]oxazole-5-carbaldehyde

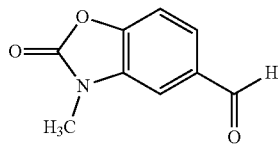

(I-26)

Intermediate I-26A: 3-methyl-5-vinylbenzo[d]oxazol-2(3H)-one

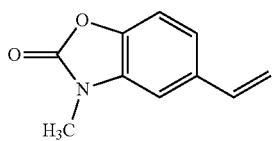

(I-26A)

Intermediate I-26A was prepared (1.60 g, 89.0%) as a brown solid according to the general synthetic protocol of Intermediate I-3A and starting from Intermediate I-4 (2.00 g, 8.77 mmol). $^1$H NMR (400 MHz, DMSO-$d_6$) δ ppm 3.41 (s, 3H), 5.26 (d, J=10.4 Hz, 1H), 5.71 (d, J=16.8 Hz, 1H), 6.72 (dd, J=16.8, 10.4 Hz, 1H), 7.01 (s, 1H), 7013 (s, 2H). LCMS (Method E): retention time 2.013 min, (M+H) 175.0.

Intermediate I-26

Intermediate I-26 was prepared (1.10 g, 80.0%) as an off white solid according to the general synthetic protocol of Intermediate I-3 and starting from Intermediate I-26A (1.60 g, 7.76 mmol). $^1$H NMR (400 MHz, DMSO-$d_6$) δ ppm 3.45 (s, 3H), 7.34 (d, J=8.0 Hz, 1H), 7.65 (s, 1H), 7.67 (d, J=7.2 Hz, 1H), 9.95 (s, 1H).

Example numbers followed by an -I or -II refer to discrete enantiomers. The enantiomer is determined based on the selection of either enantiomer of intermediate I-1 (I-1-I or I-1-II). If intermediate I-1-I is used, then the products are designated as "-I". If intermediate I-1-II is used, then the products are designated as "-II".

Examples 1-I and 1-II 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-4-carbonitrile (Enantiomer-I and II)

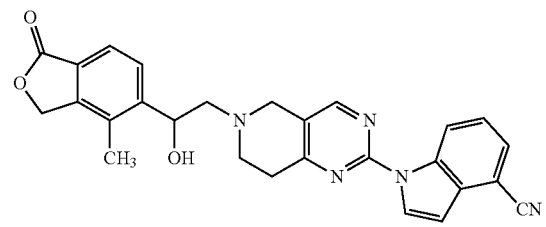

(1-I and 1-II)

Intermediate 1A 1-(6-benzyl-5,6,7,8-tetrahydropyrido[4,3-d]pyrimidin-2-yl)-1H-indole-4-carbonitrile

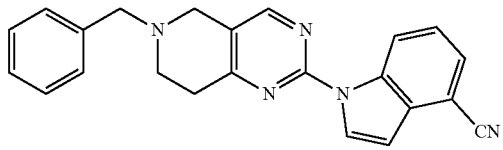

(1A)

To a stirred solution of Intermediate I-19 (0.500 g, 1.92 mmol) and 1H-indole-4-carbonitrile (0.328 g, 2.31 mmol) in dioxane (15 mL) were added $K_2CO_3$ (0.798 g, 5.78 mmol) and XANTPHOS (0.223 g, 0.385 mmol). The resulting reaction mixture was degassed with nitrogen for 5 minutes then $Pd_2(dba)_3$ (0.176 g, 0.193 mmol) was added and the reaction mixture was degassed with nitrogen for an additional 5 minutes. The reaction mixture was heated in a sealed tube at 100° C. for 16 h, cooled and concentrated under reduced pressure. The residue was diluted with EtOAc and filtered through celite. The filtrate was dried over anhydrous sodium sulfate, filtered and concentrated under reduced pressure. The crude solid was washed with diethyl ether (50 mL) to give Intermediate IA (0.600 g, 81.1%) as a pale yellow solid. $^1$H NMR (400 MHz, DMSO-d$_6$) δ ppm 2.85 (t, J=5.6 Hz, 2H), 3.02 (t, J=5.6 Hz, 2H), 3.62 (s, 2H), 3.74 (s, 2H), 6.90 (d, J=3.6 Hz, 1H), 7.27-7.30 (m, 1H), 7.34-7.40 (m, 4H), 7.48 (t, J=8.4 Hz, 1H), 7.74 (d, J=7.2 Hz, 1H), 8.48 (d, J=3.6 Hz, 1H), 8.66 (s, 1H), 9.04 (d, J=8.4 Hz, 1H). LCMS (Method-R): retention time 1.60 min, [M+H] 366.4.

Intermediate 1B 1-(5,6,7,8-tetrahydropyrido[4,3-d]pyrimidin-2-yl)-1H-indole-4-carbonitrile

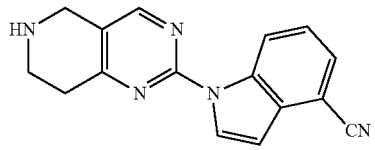

(1B)

Intermediate 1B was prepared (0.380 g, 58.0%) as an off white solid according to the general synthetic protocol of Intermediate I-23 and starting from Intermediate 1A (0.600 g, 1.64 mmol). $^1$H NMR (400 MHz, DMSO-d$_6$) δ ppm 2.88 (t, J=8.0 Hz, 3H), 3.07 (t, J=8.0 Hz, 2H), 3.89 (s, 2H), 6.90 (d, J=4.8 Hz, 1H), 7.48 (t, J=10.0 Hz, 1H), 7.75 (d, J=10.0 Hz, 1H), 8.49 (d, J=5.2 Hz, 1H), 8.57 (s, 1H), 9.06 (d, J=11.8 Hz, 1H). LCMS (Method R): retention time 1.59 min, [M+H] 276.2.

Example 1-I: (Enantiomer-I)

Intermediate 1B (0.0950 g, 0.345 mmol) and Intermediate I-1-I (0.0980 g, 0.518 mmol) were dissolved in ethanol (15 mL) and heated to reflux for 48 h. The resulting reaction mixture was evaporated to dryness under reduced pressure. The residue was purified by preparative HPLC [Sunfire (250×30 ID) 5 micron, mobile phase A: 0.1% HCOOH in water, mobile phase B: ACN, Gradient: 10-45% B over 7 minutes, Flow rate: 25 mL/min, retention time 12.05, UV 254 nm] to give Example 1-I (Enantiomer-I) (0.0800 g, 48.3%) as an off-white solid. $^1$H NMR (400 MHz, DMSO-d$_6$) δ ppm 2.33 (s, 3H), 2.66-2.77 (m, 2H), 3.00 (t, J=5.2 Hz, 4H), 3.84 (q, J=8.4 Hz, 2H), 5.22 (t, J=4.4 Hz, 1H), 5.40 (d, J=2.8 Hz, 3H), 5.44 (d, J=4.0 Hz, 1H), 6.91 (dd, J=0.4 Hz, J=3.2 Hz, 1H), 7.49 (t, J=8.0 Hz, 1H), 7.70 (t, J=8.0 Hz, 1H), 7.74 (d, J=3.2 Hz, 1H), 8.50 (d, J=3.6 Hz, 1H), 8.64 (s, 1H), 9.06 (d, J=8.4 Hz, 1H). LCMS (Method-E): retention time 2.85, [M+H] 466.2. HPLC (Method-N): retention time 6.71 min, purity 95.4%. (Method-O): retention time 8.39 min, purity 97.4%. Chiral purity (method XVI): retention time 14.67 min, 100% ee.

Example 1-II: (Enantiomer-II)

Example 1-II (Enantiomer-II) was prepared (0.010 g, 6.28%) as off white solid according to the general synthetic protocol of Example 1-I and starting from Intermediate 1B (0.095 g, 0.345 mmol) and Intermediate I-1-II. $^1$H NMR (400 MHz, DMSO-d$_6$) δ ppm 2.33 (s, 3H), 2.66-2.77 (m, 2H), 3.00 (t, J=5.2 Hz, 4H), 3.84 (q, J=8.4 Hz, 2H), 5.22 (t, J=4.4 Hz, 1H), 5.40 (d, J=2.8 Hz, 3H), 5.44 (d, J=4.0 Hz, 1H), 6.91 (dd, J=0.4 Hz, J=3.2 Hz, 1H), 7.49 (t, J=8.0 Hz, 1H), 7.70 (t, J=8.0 Hz, 1H), 7.74 (d, J=3.2 Hz, 1H), 8.50 (d, J=3.6 Hz, 1H), 8.64 (s, 1H), 9.06 (d, J=8.4 Hz, 1H). LCMS/HPLC (Method A): retention time 2.18, [M+1] 466.1, purity: 96.3%. (Method B): retention time 1.39, [M+1] 466.1, purity: 94.5%. Chiral purity (Method XVI): retention time 11.37 min, 98.4% ee.

Example 2

2-fluoro-5-((6-((1-oxo-1,3-dihydroisobenzofuran-5-yl)methyl)-5,6,7,8-tetrahydropyrido[4,3-d]pyrimidin-2-yl)amino)benzonitrile

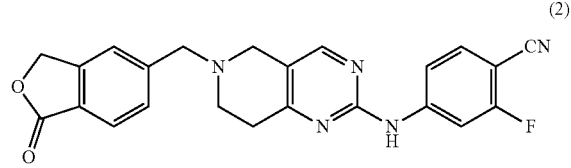 [SMILES: N#Cc1ccc(Nc2ncc3c(n2)CCN(Cc2ccc4c(c2)COC4=O)C3)cc1F]

(2)

Intermediate 2A: tert-butyl 2-((4-cyano-3-fluorophenyl)amino)-7,8-dihydropyrido[4,3-d]pyrimidine-6(5H)-carboxylate

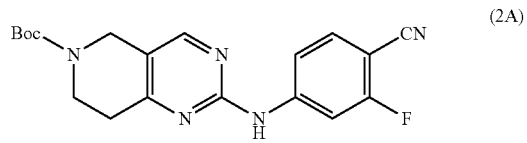 [SMILES: CC(C)(C)OC(=O)N1CCc2nc(Nc3ccc(C#N)c(F)c3)ncc2C1]

(2A)

To a solution of Intermediate I-20 (0.500 g, 1.59 mmol) and 4-amino-2-fluorobenzonitrile (0.260 g, 1.91 mmol) in dioxane (3 mL) was added K$_2$CO$_3$ (0.440 g, 3.18 mmol). The reaction mixture was purged with nitrogen for 10 min. Pd$_2$(dba)$_3$ (0.146 g, 0.159 mmol) and XANTPHOS (0.0460 g, 0.0800 mmol) were added and the reaction mixture was heated to 100° C. for 12 h in a sealed tube. The reaction mixture was cooled to ambient temperature and filtered through celite and then washed with ethyl acetate (2×20 mL). The filtrate was diluted with water (50 mL) and extracted with ethyl acetate (2×150 mL). The combined organic extracts were dried over anhydrous Na$_2$SO$_4$, filtered, and concentrated under reduced pressure. The residue was purified by CombiFlash (Redisep-12 g, 40% EtOAc/n-hexanes), to obtain Intermediate 2A (0.350 g, 59.5%). $^1$H NMR (400 MHz, DMSO-d$_6$) δ ppm 1.44 (s, 9H), 2.83 (t, J=6.0 Hz, 2H), 3.67 (t, J=5.8 Hz, 2H), 4.49 (s, 2H), 7.62 (dd, J=9.0, 2.0 Hz, 1H), 7.71-7.84 (m, 1H), 8.11 (dd, J=13.3, 1.8 Hz, 1H), 8.48 (s, 1H), 10.43 (s, 1H). LCMS (Method E): retention time 3.01 min, [M−H] 370.2.

53

Intermediate 2B: 2-fluoro-4-((5,6,7,8-tetrahydro-pyrido[4,3-d]pyrimidin-2-yl)amino)benzonitrile

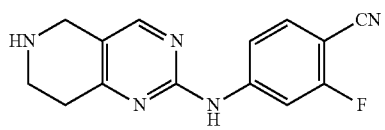

(2B)

To a stirred solution of Intermediate 2A (0.350 g, 0.948 mmol) in DCM (5 mL) was added TFA (0.730 mL, 9.48 mmol). The reaction mixture was stirred at ambient temperature for 3 h. The reaction mixture was concentrated under reduced pressure and the residue was diluted with water and basified with 10% NaHCO$_3$ solution. The aqueous mixture was extracted with DCM (2×10 mL) and the combined organic layers were concentrated under reduced pressure to obtain Intermediate 2B (0.200 g, 78.0%). $^1$H NMR (400 MHz, DMSO-d$_6$) δ ppm 3.04 (t, J=6.3 Hz, 2H), 3.40 (t, J=6.3 Hz, 2H), 4.28 (br s, 2H), 7.63 (dd, J=8.8, 2.3 Hz, 1H), 7.75-7.85 (m, 1H), 8.11 (dd, J=13.3, 1.76 Hz, 1H), 8.53 (s, 1H), 9.07 (br s, 1H), 10.5 (s, 1H). LCMS (Method E): retention time 1.55 min, [M+H] 270.2.

Example 2

To a stirred solution of Intermediate 2B (0.0500 g, 0.186 mmol) in MeOH (3 mL), was added Intermediate I-3 (0.0360 g, 0.223 mmol). The reaction mixture was stirred at ambient temperature for 15 min, after which NaCNBH$_4$ (0.0180 g, 0.279 mmol) was added. The reaction mixture was stirred at ambient temperature for 14 h and evaporated to dryness under reduced pressure. The residue was diluted with water (20 mL) and extracted with ethyl acetate (3×20 mL). The combined organic extracts were dried over anhydrous sodium sulfate, filtered and concentrated under reduced pressure. The residue was purified via preparative LC/MS [XBridge C18 (19×10 mm) 5 μm; Mobile Phase A: 10 mM NH$_4$OAc in water; Mobile Phase B: ACN; Gradient: 10-35% B over 25 min, followed by a 10 minute hold at 35% B and 5 minute hold at 100% B; Flow: 15 mL/min. UV 220 nm] to obtain Example 2 (0.009 g, 11.6%). $^1$H NMR (400 MHz, DMSO-d$_6$) δ ppm 2.81-2.92 (m, 4H), 3.55 (s, 2H), 3.87 (s, 2H), 5.41 (s, 2H), 7.57-7.63 (m, 2H), 7.69 (s, 1H), 7.71-7.78 (m, 1H), 7.83 (d, J=7.8 Hz, 1H), 8.10 (dd, J=13.3, 1.8 Hz, 1H), 8.33 (s, 1H), 10.4 (s, 1H). $^{19}$F NMR (400 MHz, DMSO-d$_6$) δ ppm 107.4. LCMS/HPLC (Method A): retention time 1.34 min, [M+H] 416.2, purity: 98.5%, (Method B): retention time 1.98 min, [M+H] 416.2, purity: 100%.

54

Examples 3-I and 3-II 1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indazole-4-carbonitrile (Enantiomer-I and II)

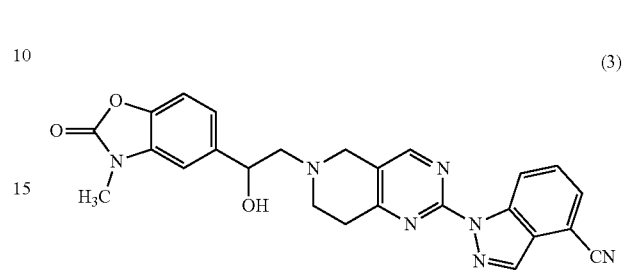

(3)

Intermediate 3A 1-(6-benzyl-5,6,7,8-tetrahydropyrido[4,3-d]pyrimidin-2-yl)-1H-indazole-4-carbonitrile

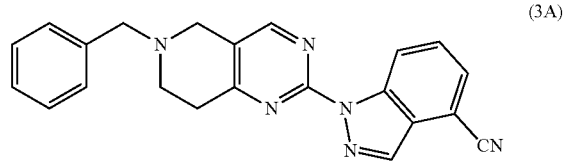 [SMILES: N#Cc1cccc2c1cnn2-c1ncc2c(n1)CCN(Cc1ccccc1)C2]

(3A)

Intermediate 3A was prepared (0.300 g, 34%) as yellow solid according to the general synthetic protocol of Intermediate 1A and starting from Intermediate I-19 (0.500 g, 1.92 mmol). $^1$H NMR (400 MHz, DMSO-d$_6$) δ ppm 2.85-2.91 (m, 2H), 2.97-3.06 (m, 2H), 3.66 (s, 2H), 3.75 (s, 2H), 7.23-7.41 (m, 5H), 7.75 (t, J=8.8 Hz, 1H), 7.91 (d, J=7.2 Hz, 1H), 8.65 (d, J=8.8 Hz, 2H), 8.96 (d, J=8.8 Hz, 1H). LCMS (Method E): retention time 2.95 min, [M+H] 367.2.

Intermediate 3B 1-(5,6,7,8-tetrahydropyrido[4,3-d]pyrimidin-2-yl)-1H-indazole-4-carbonitrile

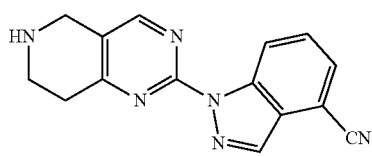

(3B)

Intermediate 3B was prepared (0.160 g, 83.0%) as pale yellow solid according to the general synthetic protocol of Intermediate 1B and starting from Intermediate 3A (0.300 g, 0.657 mmol). $^1$H NMR (400 MHz, DMSO-d$_6$) δ ppm 2.85-2.92 (m, 2H), 3.04-3.12 (m, 2H), 3.91 (s, 2H), 7.24-7.38 (m, 1H), 7.74 (t, J=8.0 Hz, 1H), 7.93 (d, J=6.8 Hz, 1H), 8.64 (d, J=5.6 Hz, 2H), 8.97 (d, J=7.6 Hz, 1H). LCMS (Method E): retention time 1.24 min, [M+H] 277.2.

Intermediate 3C 1-(6-(2-(3-methyl-2-oxo-2,3-dihydrobenzo[d]ox-azol-5-yl)-2-oxoethyl)-5,6,7,8-tetrahydropyrido[4,3-d]pyrimidin-2-yl)-1H-indazole-4-carbonitrile

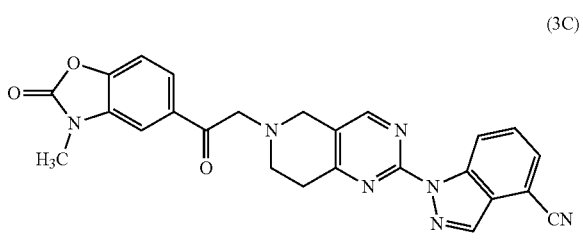 [SMILES: Cn1c(=O)oc2ccc(C(=O)CN3CCc4nc(-n5ncc6c(C#N)cccc65)ncc4C3)cc21]

(3C)

To a solution of Intermediate 3B (0.150 g, 0.432 mmol) in THF (20 mL) was added DIPEA (0.167 g, 1.29 mmol) and Intermediate I-21 (0.280 g, 0.518 mmol). The resulting reaction mixture was stirred at ambient temperature for 4 h and was evaporated to dryness under reduced pressure to obtain Intermediate 3C (0.400 g 85.0%). LCMS (method R): retention time 1.11 min, [M+H] 466.3. The compound was taken forward directly to the subsequent step without further purification or characterization.

Examples 3-I and 3-II: (Enantiomers I and II)

To a solution of Intermediate 3C (0.400 g, 0.378 mmol) in THF (20 mL) was added MeOH (5 mL) followed by NaBH$_4$ (0.0430 g, 1.13 mmol) portion wise at 0° C. The reaction mixture was stirred at ambient temperature for 1 h. The reaction mixture was diluted with water then extracted with 10% MeOH/DCM (3×50 mL). The combined organic layers were washed with brine (50 mL), dried over anhydrous sodium sulfate, and evaporated under reduced pressure. The crude residue was purified by Prep HPLC [Sunfire C18 (250×30 ID) 5 micron, A: 0.1% HCOOH in H$_2$O, B: Acetonitrile, % B: 0-100 at 16 min, Flow: 17 mL/min, retention time 14.5 min, UV 220 nm] to obtain racemate (0.0600 g, 33.6%). The racemate was chirally separated by SFC [Luxcellulose-4 (250×21.5 mm) 5 micron, mobile phase 50% DEA in MeOH, Total flow: 80.0 g/min, Back pressure: 100 bar temperature: 30° C., UV: 251 nm]. The faster eluting compound (retention time 21.00 min) was designated as Example 3-I (Enantiomer-I), (0.0080 g, 13.0%). $^1$H NMR (400 MHz, DMSO-d$_6$) δ ppm 2.55-2.70 (m, 2H), 2.95-3.05 (m, 4H), 3.35 (s, 3H), 3.84 (s, 2H), 4.85-4.93 (m, 1H), 5.33 (d, J=3.6 Hz, 1H), 7.17 (dd, J=8.0 Hz, J=1.2 Hz, 1H), 7.27 (s, 1H), 7.30 (d, J=7.2 Hz, 1H), 7.75-7.79 (m, 1H), 7.95 (d, J=8.0 Hz, 1H), 8.67 (s, 1H), 8.68 (d, J=8.8 Hz, 1H), 9.0 (d, J=8.8 Hz, 1H). LCMS/HPLC (Method A): retention time 1.28 min, [M+H] 468.1, purity: 100%. (Method B): retention time 1.70 min, [M+H] 468.2, purity: 98.5%, Chiral purity (Method IX): retention time 39.0 min, 100% ee.

The slower eluting compound (retention time 27.0 min) was designated as Example 3-II (Enantiomer-II) (0.0070 g 12.0%). $^1$H NMR (400 MHz, DMSO-d$_6$) δ 2.55-2.7 (m, 2H), 2.95-3.05 (m, 4H), 3.35 (s, 3H), 3.84 (s, 2H), 4.85-4.93 (m, 1H), 5.33 (d, J=3.6 Hz, 1H), 7.17 (dd, J=8.0 Hz, J=1.2 Hz, 1H), 7.27 (s, 1H), 7.30 (d, J=7.2 Hz, 1H), 7.75-7.79 (m, 1H), 7.95 (d, J=8.0 Hz, 1H), 8.67 (s, 1H), 8.68 (d, J=8.8 Hz, 1H), 9.0 (d, J=8.8 Hz, 1H). LCMS/HPLC (Method A): retention time 1.28 min, [M+H] 468.1, purity: 100%. (Method B): retention time 1.70 min, [M+H] 468.2, purity: 98.6%. Chiral purity (Method IX): retention time 47.14 min, 95% ee.

Example 4

2-fluoro-4-((2-((1-oxo-1,3-dihydroisobenzofuran-5-yl)methyl)-1,2,3,4-tetrahydroisoquinolin-6-yl)amino)benzonitrile

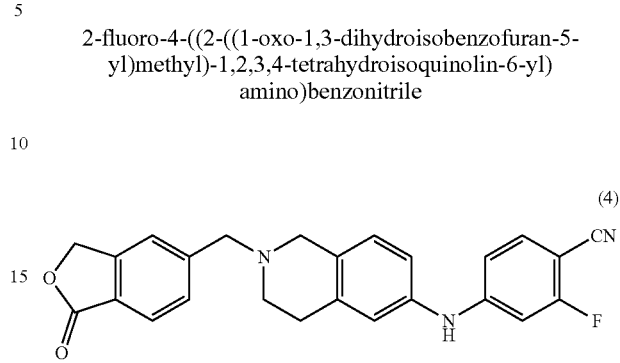

(4)

Intermediate 4A: tert-butyl 6-((4-cyano-3-fluorophenyl)amino)-3,4-dihydroisoquinoline-2(1H)-carboxylate

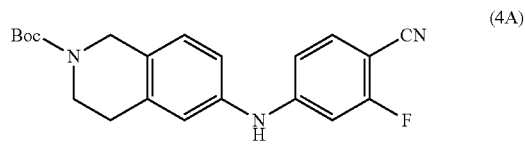 [SMILES: CC(C)(C)OC(=O)N1CCc2cc(Nc3ccc(C#N)c(F)c3)ccc2C1]

(4A)

To a solution of Intermediate I-22 (0.100 g, 0.320 mmol) and 4-amino-2-fluorobenzonitrile (0.0520 g, 0.384 mmol) in dioxane (1 mL) was added K$_2$CO$_3$ (0.0890 g, 0.641 mmol). The resulting reaction mixture was purged with nitrogen for 10 min and Pd$_2$(dba)$_3$ (0.0290 g, 0.0320 mmol), followed by the addition of XANTPHOS (9.27 mg, 0.0160 mmol). The resulting reaction mixture was heated at 100° C. for 12 h in a sealed tube and was cooled to ambient temperature and filtered through celite. The filtrate was diluted with water (20 mL) and extracted with EtOAc (2×15 mL). The combined organic extracts were dried over anhydrous sodium sulfate, filtered and concentrated under reduced pressure. The residue was purified by CombiFlash (Redisep-12 g, 40% EtOAc/n-hexanes), to obtain Intermediate 4A (0.0700 g, 59.5%) as a yellow solid. $^1$H NMR (300 MHz, DMSO-d$_6$) δ ppm 1.43 (s, 9H), 2.77 (t, J=6.04 Hz, 2H), 3.54 (t, J=5.85 Hz, 2H), 4.47 (s, 2H), 6.79-6.82 (m, 1H), 6.84 (s, 1H), 7.00-7.05 (m, 2H), 7.17 (d, J=8.69 Hz, 1H), 7.54-7.66 (m, 1H), 9.14 (s, 1H). LCMS (Method E): retention time 3.36 min, [M−H] 366.0.

Intermediate 4B: 2-fluoro-4-((1,2,3,4-tetrahydroisoquinolin-6-yl)amino)benzonitrile

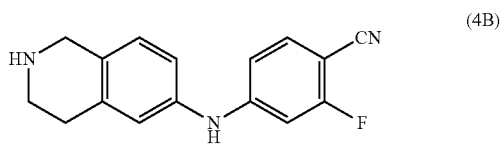 [SMILES: N#Cc1ccc(Nc2ccc3c(c2)CCNC3)cc1F]

(4B)

Intermediate 4B was prepared (0.0200 g, 55.0%) as a pale yellow solid according to the general synthetic protocol of Intermediate 2B and starting from Intermediate 4A (0.05 g, 0.136 mmol). $^1$H NMR (300 MHz, DMSO-$d_6$) δ ppm 2.62-2.77 (m, 2H), 2.93 (br s, 2H), 3.81 (br s, 2H), 6.70-6.84 (m, 3H), 6.87-7.07 (m, 3H), 7.58 (t, J=8.50 Hz, 1H), 9.07 (br s, 1H). LCMS (Method E): retention time 1.50 min, [M+H] 268.0.

Example 4

Example 4 was prepared (0.0110 g 14.2%) as a yellow solid according to the general synthetic protocol of Example 2 and starting from Intermediate 4B (0.0800 g, 0.215 mmol). $^1$H NMR (400 MHz, DMSO-$d_6$) δ ppm 2.68-2.76 (m, 2H), 2.84 (d, J=5.52 Hz, 2H), 3.56 (s, 2H), 3.82 (s, 2H), 5.41 (s, 2H), 6.75-6.83 (m, 2H), 6.91-6.98 (m, 2H), 7.00-7.04 (m, 1H), 7.54-7.62 (m, 2H), 7.68 (s, 1H), 7.83 (d, J=8.03 Hz, 1H), 9.10 (s, 1H). $^{19}$F NMR (400 MHz, DMSO-$d_6$) δ ppm 107.84. LCMS/HPLC (Method A): retention time 1.14 min, [M+H] 414.3, purity: 99.2. (Method B): retention time 1.80 min, [M+H] 414.3, purity: 100%.

Example 5

4-methyl-5-((2-((4-methyl-1-oxo-1,3-dihydroisobenzofuran-5-yl)amino)-7,8-dihydropyrido[4,3-d]pyrimidin-6(5H)-yl)methyl)isobenzofuran-1(3H)-one (5)

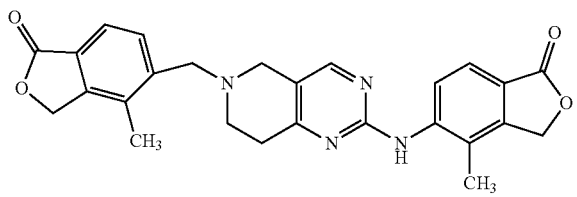

Intermediate 5A: tert-butyl 2-((4-methyl-1-oxo-1,3-dihydroisobenzofuran-5-yl)amino)-7,8-dihydropyrido[4,3-d]pyrimidine-6(5H)-carboxylate (5A)

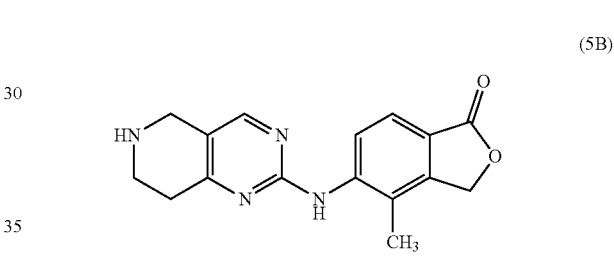

To a stirred solution of Intermediate 2 (0.500 g, 1.92 mmol) and 5-bromo-4-methylisobenzofuran-1(3H)-one (0.454 g, 1.99 mmol) in dioxane (15 mL) were added $K_2CO_3$ (0.552 g, 4.00 mmol) and XANTPHOS (0.0580 g, 0.100 mmol). The resulting reaction mixture was degassed with nitrogen for 5 minutes followed by the addition of $Pd_2(dba)_3$ (0.183 g, 0.200 mmol). The reaction mixture was degassed with nitrogen for an additional 5 minutes. The reaction mixture was heated 100° C. for 1 h by using microwave reactor, cooled and concentrated under reduced pressure. The residue was diluted with EtOAc and filtered through celite. The filtrate was dried over anhydrous sodium sulfate, filtered and concentrated under reduced pressure. The crude solid was purified by CombiFlash (Redisep-24 g, 65% EtOAc/n-hexanes), to obtained Intermediate 5A (0.380 g, 48.0%) as a yellow solid. $^1$H NMR (400 MHz, DMSO-$d_6$) δ ppm 1.40-1.48 (m, 9H), 2.20 (s, 3H), 2.74 (t, J=6.02 Hz, 2H), 3.64 (t, J=6.02 Hz, 2 H), 4.45 (s, 2H), 5.38 (s, 2H), 7.63 (d, J=8.03 Hz, 1H), 7.92 (d, J=8.03 Hz, 1H), 8.32 (s, 1H), 9.12 (s, 1H). LCMS (Method E): retention time 2.42 min, [M+H] 397.2.

Intermediate 5B: 4-methyl-5-((5,6,7,8-tetrahydropyrido[4,3-d]pyrimidin-2-yl)amino) isobenzofuran-1(3H)-one (5B)

Intermediate 5B was synthesized (0.130 g, 69.6%) as a yellow solid according to the general synthetic protocol of Intermediate 4B and starting from Intermediate 5A (0.250 g, 0.631 mmol). $^1$H NMR (400 MHz, DMSO-$d_6$) δ ppm 2.18 (s, 3H), 2.93 (t, J=6.27 Hz, 2H), 3.46 (d, J=6.53 Hz, 2H), 4.22 (s, 2H), 5.38 (s, 2H), 7.64 (d, J=8.53 Hz, 1H), 7.82 (d, J=8.53 Hz, 1H), 8.35 (s, 1H), 9.14 (br s, 1H), 9.32 (s, 1H). LCMS (Method E): retention time 0.97 min, [M+H] 297.2.

Example 5

Example 5 was synthesized (12.9 mg, 16.8%) as a yellow solid according to the general synthetic protocol of Example 2 and starting from Intermediate 5B (0.0500 g, 0.169 mmol). $^1$H NMR (400 MHz, DMSO-$d_6$) δ ppm 2.32 (s, 3H), 2.66-2.74 (m, 2H), 2.99 (t, J=4.8 Hz, 4H), 3.83 (d, J=8.8 Hz, 2H), 5.23 (t, J=4.0 Hz, 1H), 5.40 (d, J=2.8 Hz, 2H), 5.44 (d, J=4.0 Hz, 1H), 6.90 (dd, J=3.6 Hz, J=0.8 Hz, 1H), 7.68-7.76 (m, 3H), 8.20 (d, J=1.2 Hz, 1H), 8.42 (d, J=3.6 Hz, 1H), 8.63 (s, 1H), 8.88 (d, J=8.8 Hz, 1H). LCMS/HPLC (Method A): retention time 0.96 min, [M+H] 457.2, purity: 100%. (Method B): retention time 1.62 min, [M+H] 457.2, purity: 100%.

Example 6

2-fluoro-4-((2-(2-(1-oxo-1,3-dihydroisobenzofuran-5-yl)ethyl)-1,2,3,4-tetrahydroisoquinolin-6-yl)amino)benzonitrile (6)

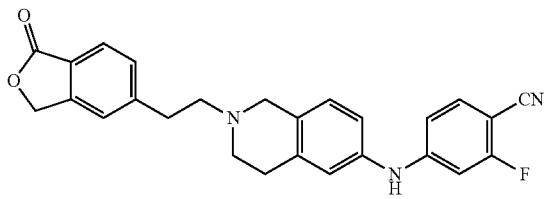

Intermediate 6A 5-(2-(6-bromo-3,4-dihydroisoquinolin-2(1H)-yl)ethyl)isobenzofuran-1(3H)-one (6A)

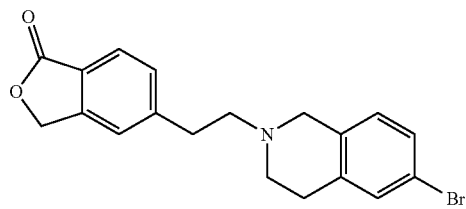

To a solution of 6-bromo-1,2,3,4-tetrahydroisoquinoline (0.700 g, 3.30 mmol) in DCM (30 mL) was added Intermediate I-13 (0.640 g, 3.63 mmol) followed by sodium triacetoxyborohydride (1.40 g, 6.60 mmol). The resulting reaction mixture was stirred at ambient temperature for 14 h. The reaction mixture was diluted by water (50 mL) and extracted with DCM (2×50 mL). The combined extracts were washed with brine (50 mL), dried over anhydrous sodium sulfate and concentrated. The crude was washed with diethyl ether (2×50 mL) to afford Intermediate 6A (1.05 g, 73.5%) as a brown solid. $^1$H NMR (400 MHz, DMSO-$d_6$) δ ppm 2.70-2.80 (m, 6H), 2.99 (t, J=10 Hz, 2H), 3.59 (s, 2H), 5.37 (s, 2H), 7.03 (d, J=10.8 Hz, 1H), 7.27 (d, J=2.4 Hz, 1H), 7.31 (s, 1H), 7.50 (d, J=10.4 Hz, 1H), 7.56 (s, 1H), 7.76 (d, J=10.4 Hz, 1H). LCMS (Method R): retention time 1.03 min, (M+H) 374.2.

Example 6

Example 6 was prepared (0.00500 g, 5.44%) as a yellow solid according to the general synthetic protocol of Intermediate 1A and starting from Intermediate 6A (0.0800 g, 0.215 mmol). $^1$H NMR (400 MHz, DMSO-$d_6$) δ ppm 2.69-2.83 (m, 6H), 3.01 (t, J=7.53 Hz, 2H), 3.61 (s, 2H), 5.38 (s, 2H), 6.75-6.83 (m, 2H), 6.91-6.99 (m, 2H), 7.06 (d, J=8.53 Hz, 1H), 7.51 (d, J=8.03 Hz, 1H), 7.54-7.63 (m, 2H), 7.76 (d, J=8.03 Hz, 1H), 9.09 (s, 1H). $^{19}$F NMR (400 MHz, DMSO-$d_6$) δ ppm −107.85. LCMS/HPLC (Method A): retention time 1.22 min, [M+H] 428.3, purity: 94.0%. (Method B): retention time 1.84 min, [M+H] 428.3, purity: 95.0%.

Example 7

2-fluoro-4-((6-(2-(1-oxo-1,3-dihydroisobenzofuran-5-yl)ethyl)-5,6,7,8-tetrahydro-1,6-naphthyridin-2-yl)amino)benzonitrile (7)

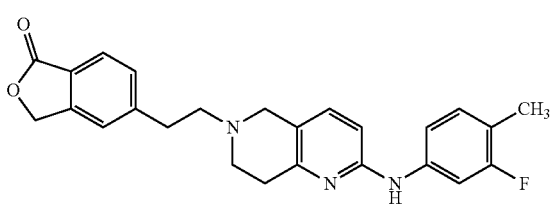

Intermediate 7A: 5-(2-(2-chloro-7,8-dihydro-1,6-naphthyridin-6(5H)-yl)ethyl) isobenzofuran-1(3H)-one (7A)

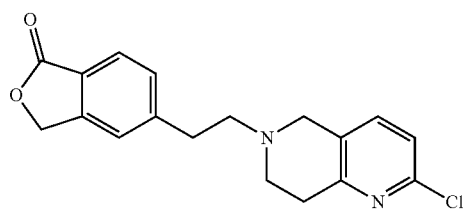

Intermediate 7A was prepared (0.300 g, 79.0%) as a brown solid according to the general synthetic protocol of Intermediate 6A and starting from Intermediate I-23 (0.350 g, 2.08 mmol). The compound was taken forward directly to the subsequent step without further purification or characterization. LCMS (Method B): retention time 0.90 min, [M+1] 329.1.

Example 7

Example 7 was prepared (0.0090 g, 13.8%) as yellow solid according to the general synthetic protocol of Intermediate 1A and starting from Intermediate 7A (0.0500 g, 0.152 mmol). $^1$H NMR (400 MHz, DMSO-$d_6$) δ ppm 2.74-2.89 (m, 6H), 2.97-3.05 (m, 2H), 3.58 (s, 2H), 5.38 (s, 2H), 6.75 (d, J=8.0 Hz, 1H), 7.35-7.43 (m, 2H), 7.51 (d, J=8.0 Hz, 1H), 7.57 (s, 1H), 7.68 (t, J=8.5 Hz, 1H), 7.76 (d, J=8.0 Hz, 1H), 8.14 (dd, J=13.5, 1.5 Hz, 1H), 9.82 (s, 1H). $^{19}$F NMR (400 MHz, DMSO-$d_6$) δ ppm 107.29. LCMS/HPLC (Method A): retention time 1.17 min, purity: 97.0% [M+H] 429.3. (Method B): retention time 1.13 min, purity: 96.0%, [M+H] 429.3.

Examples 8-I and 9-I 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile (8-I) and 1-(6-(2-hydroxy-1-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile (9-I)

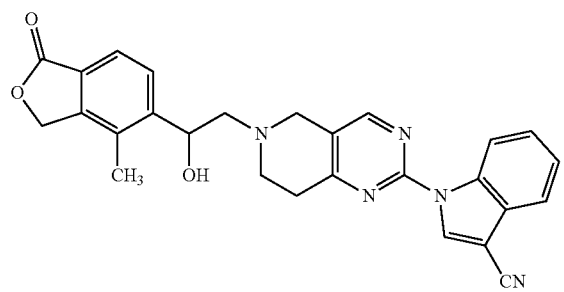

Intermediate 8A: tert-butyl 2-(3-cyano-1H-indol-1-yl)-7,8-dihydropyrido[4,3-d]pyrimidine-6(5H)-carboxylate

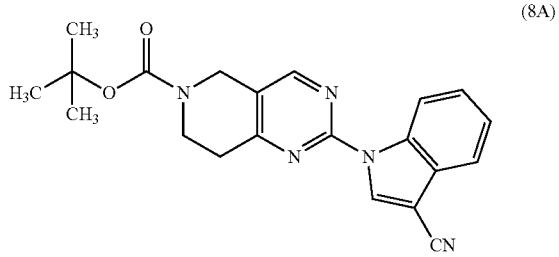 [SMILES: CC(C)(C)OC(=O)N1CCc2nc(-n3cc(C#N)c4ccccc43)ncc2C1]

Intermediate 8A was prepared (0.450 g, 90.0%) as pale yellow solid according to the general synthetic protocol of Intermediate 1A and starting from Intermediate I-20 (0.200 g, 0.637 mmol). LCMS (method B): retention time 1.55 min, [M+1] 376.3. The compound was taken forward directly to the subsequent step without further purification or characterization.

Intermediate 8B 1-(5,6,7,8-tetrahydropyrido[4,3-d]pyrimidin-2-yl)-1H-indole-3-carbonitrile

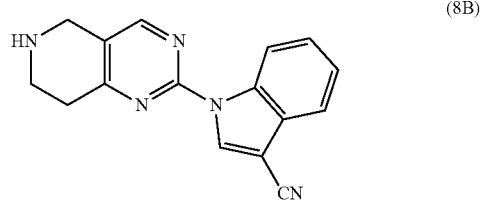 [SMILES: N#Cc1cn(-c2ncc3c(n2)CCNC3)c2ccccc12]

Intermediate 8B was prepared (0.150 g, 53.1%) as an off white solid according to the general synthetic protocol of Intermediate 4B and starting from Intermediate 8A (0.650 g, 0.831 mmol). $^1$H NMR (400 MHz, DMSO-$d_6$) δ ppm 2.90 (t, J=5.8 Hz, 2H), 3.03-3.14 (m, 2H), 3.92 (s, 2H), 7.37-7.46 (m, 1H), 7.47-7.57 (m, 1H), 7.75 (d, J=8.0 Hz, 1H), 8.62 (s, 1H), 8.75-8.85 (m, 1H), 9.06 (s, 1H). LCMS (Method B): retention time 0.71 min, [M+H] 276.1.

Examples 8-I and 9-I

Example 8-I (Enantiomer I) was prepared (0.0390 g, 38.8%) as a white solid according to the general synthetic protocol of Intermediate 1-I and starting from Intermediate 8B (0.0600 g, 0.218 mmol). $^1$H NMR (400 MHz, DMSO-$d_6$) δ ppm 2.31 (s, 3H), 2.66-2.77 (m, 2H), 2.99-3.03 (m, 4H), 3.80-3.90 (m, 2H), 5.20-5.23 (m, 1H), 5.40 (d, J=3.2 Hz, 2H), 5.45 (d, J=4.0 Hz, 1H), 7.43 (t, J=7.6 Hz, 1H), 7.51 (t, J=7.6 Hz, 1H), 7.70 (d, J=8.0 Hz, 1H), 7.73-7.76 (m, 2H), 8.68 (s, 1H), 8.81 (d, J=8.4 Hz, 1H), 9.07 (s, 1H). LCMS/HPLC (Method A): retention time 1.49 min, [M+H] 466.2, purity: 96.7%. (Method B): retention time 2.26 min, [M+H] 466.2, purity: 100%. Chiral purity (Method XX): retention time 13.08 min, 100% ee.

Example 9-I (Enantiomer II) obtained as a side product, as an off white solid (0.0100 g, 9.76%). $^1$H NMR (400 MHz, DMSO-$d_6$) δ ppm 2.32 (s, 3H), 2.88-3.00 (m, 4H), 3.71-3.77 (m, 2H), 3.93-4.02 (m, 3H), 4.91 (t, J=1.6 Hz, 1H), 5.42 (s, 2H), 7.42 (t, J=7.6 Hz, 1H), 7.50 (t, J=7.6 Hz, 1H), 7.66-7.74 (m, 3H), 8.63 (s, 1H), 8.79 (d, J=8.8 Hz, 1H), 9.05 (s, 1H). LCMS/HPLC (Method A): retention time 1.52 min, [M+H] 466.0, purity: 98.5%, LCMS (Method B): retention time 2.21 min, [M+H] 466.0, purity: 97.9%. Chiral purity: (Method-XVIII): retention time 13.60 min, 100% ee.

Example 10

2-fluoro-4-(((2-(4-methyl-1-oxo-1,3-dihydroisobenzofuran-5-yl)-1,2,3,4-tetrahydroisoquinolin-6-yl)amino)methyl)benzonitrile (10)

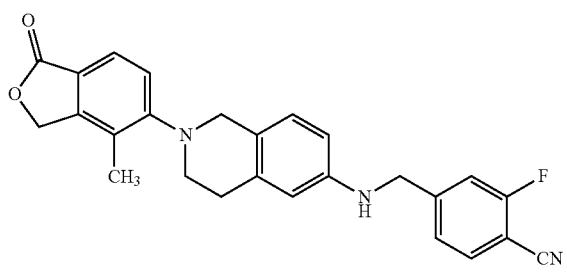

Intermediate 10A: tert-butyl 6-((4-cyano-3-fluorobenzyl)amino)-3,4-dihydroisoquinoline-2(1H)-carboxylate (10A)

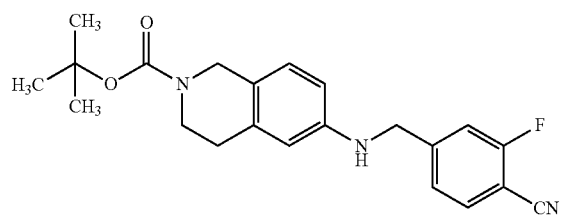

To a solution of tert-butyl 6-amino-3,4-dihydroisoquinoline-2(1H)-carboxylate (0.250 g, 1.01 mmol) in acetonitrile (10 mL) were added $K_2CO_3$ (0.417 g, 3.02 mmol) and KI (0.016 g, 0.101 mmol). The reaction mixture was stirred for 15 min. Intermediate I-18 (0.259 g, 1.21 mmol) was added to the resulting mixture and the reaction mixture was stirred at room temperature for 12 h. Reaction mixture was diluted by water (20 mL) and extracted with EtOAc (2×30 mL). The combined organic layer was washed with brine, dried over sodium sulfate and concentrated under vacuum. The resulting residue was purified by column chromatography using CombiFlash (Redisep-12 g, 30% EtOAc/n-hexane) to afford Intermediate 10A (0.300 g, 78.0%) as an off white solid. $^1$H NMR (400 MHz, DMSO-$d_6$) δ ppm 1.35-1.47 (m, 9H), 2.60 (s, 2H), 3.46 (t, J=6.0 Hz, 2H), 4.31 (br s, 2H), 4.37 (d, J=6.0 Hz, 2H), 6.26-6.37 (m, 2H), 6.40 (dd, J=8.3, 2.8 Hz, 1H), 6.84 (d, J=7.5 Hz, 1H), 7.32-7.51 (m, 2H), 7.80-7.95 (m, 1H). LCMS (Method T): retention time 1.19 min, [M+H] 382.1.

Intermediate 10B: 2-fluoro-4-(((1,2,3,4-tetrahydroisoquinolin-6-yl)amino)methyl) benzonitrile (10B)

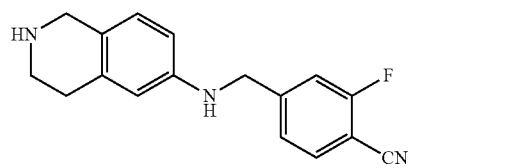

Intermediate 10B was prepared (0.150 g, 67.8%) as an off white solid according to the general synthetic protocol of Intermediate 4B and starting from Intermediate 10A (0.300 g, 0.786 mmol). $^1$H NMR (300 MHz, DMSO-$d_6$) δ ppm 2.84 (t, J=5.8 Hz, 2H), 3.36 (t, J=5.8 Hz, 2H), 3.66 (s, 2H), 4.34 (d, J=6.4 Hz, 2H), 6.15 (t, J=6.0 Hz, 1H), 6.24 (s, 1H), 6.31 (d, J=7.9 Hz, 1H), 6.68 (d, J=8.3 Hz, 1H), 7.28-7.51 (m, 2H), 7.86 (t, J=7.5 Hz, 1H), LCMS (Method E): retention time 1.86 min, [M+H] 282.2.

Example 10

Example 10 was prepared (0.0013 g, 0.90%) as an off white solid according to the general synthetic protocol of Intermediate 1A and starting from Intermediate 10B (0.100 g, 0.355 mmol). $^1$H NMR (400 MHz, DMSO-$d_6$) δ ppm 2.21 (s, 3H), 2.82 (t, J=5.5 Hz, 2H), 3.23 (t, J=5.7 Hz, 2H), 4.07 (s, 2H), 4.39 (d, J=6.4 Hz, 2H), 5.33 (s, 2H), 6.30 (t, J=6.4 Hz, 1H), 6.35-6.45 (m, 2H), 6.86 (d, J=8.3 Hz, 1H), 7.24 (d, J=8.3 Hz, 1H), 7.40 (dd, J=8.1, 1.5 Hz, 1H), 7.47 (d, J=11.5 Hz, 1H), 7.64 (d, J=8.1 Hz, 1H), 7.88 (dd, J=8.1, 6.8 Hz, 1H). $^{19}$F NMR (400 MHz, DMSO-$d_6$) δ ppm 109.04. LCMS/HPLC (Method A): retention time 2.25 min, [M+H] 428.1, purity: 96.4%. (Method B): retention time 2.23 min, [M+H] 428.2, purity: 100%.

The Examples in Table 1 were synthesized according to the general synthetic procedures described in Examples 1 to 10.

TABLE 1

| Ex. No. | Structure | Name |
| --- | --- | --- |
| 8-II | 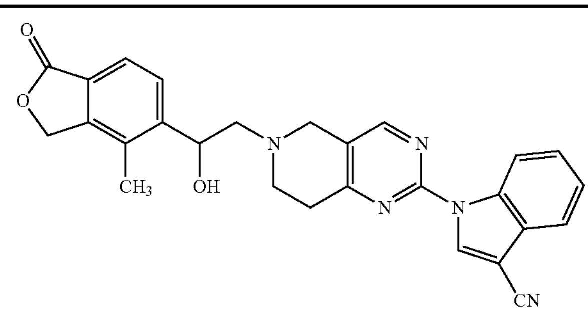 | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile (Enantiomer-II) |

TABLE 1-continued

| Ex. No. | Structure | Name |
|---|---|---|
| 9-II | 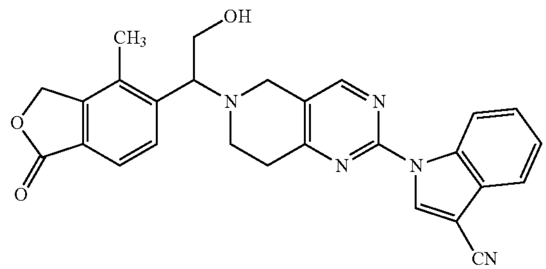 [SMILES: Cc1c(C(CO)N2CCc3nc(-n4cc(C#N)c5ccccc54)ncc3C2)ccc2c1COC2=O] | 1-(6-(2-hydroxy-1-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile (Enantiomer-II) |
| 11 | 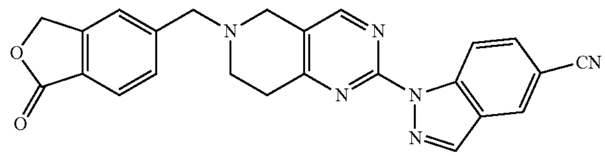 [SMILES: N#Cc1ccc2c(cnn2-c2ncc3c(n2)CCN(Cc2ccc4c(c2)COC4=O)C3)c1] | 1-(6-((1-oxo-1,3-dihydroisobenzofuran-5-yl)methyl)-5,6,7,8-tetrahydropyrido[4,3-d]pyrimidin-2-yl)-1H-indazole-5-carbonitrile |
| 12-I | 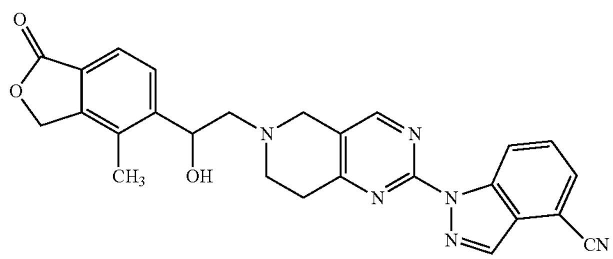 [SMILES: Cc1c(C(O)CN2CCc3nc(-n4ncc5c(C#N)cccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-4-carbonitrile (Enantiomer-I) |
| 12-II | 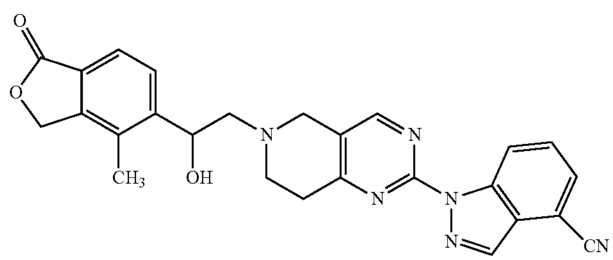 | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-4-carbonitrile (Enantiomer-II) |
| 13 | 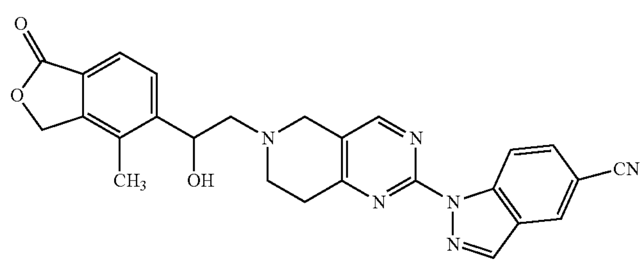 | 1-(6-((4-methyl-1-oxo-1,3-dihydro-isobenzofuran-5-yl)methyl)-5,6,7,8-tetrahydropyrido[4,3-d]pyrimidin-2-yl)-1H-indazole-5-carbonitrile |
| 14 | 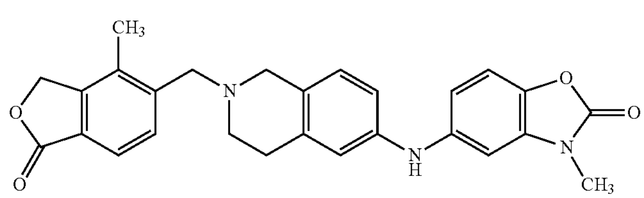 | 3-methyl-5-((2-((4-methyl-1-oxo-1,3-dihydroisobenzofuran-5-yl)methyl)-1,2,3,4-tetrahydroisoquinolin-6-yl)amino)benzo[d]oxazol-2(3H)-one |

TABLE 1-continued

| Ex. No. | Structure | Name |
|---|---|---|
| 15 | 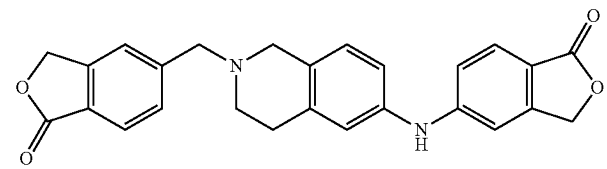 [SMILES: O=C1OCc2cc(CN3CCc4cc(Nc5ccc6c(c5)COC6=O)ccc4C3)ccc21] | 5-((6-((1-oxo-1,3-dihydroisobenzofuran-5-yl)amino)-3,4-dihydroisoquinolin-2(1H)-yl)methyl)isobenzofuran-1(3H)-one |
| 16-I | 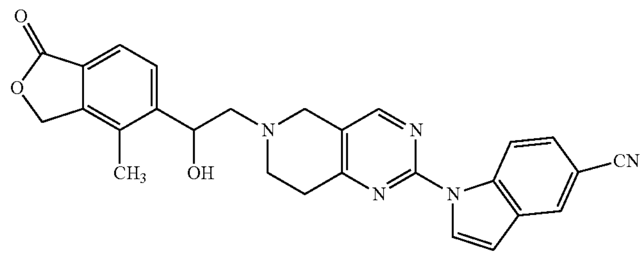 [SMILES: Cc1c(C(O)CN2CCc3nc(-n4ccc5cc(C#N)ccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-5-carbonitrile (Enantiomer I) |
| 16-II | 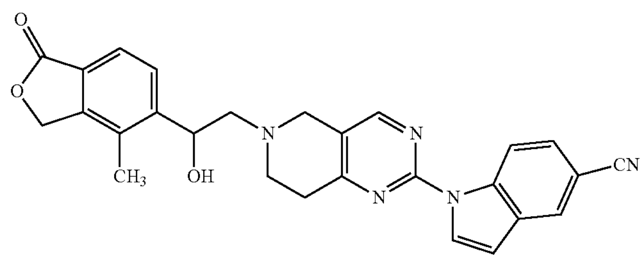 | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-5-carbonitrile (Enantiomer II) |
| 17-I | 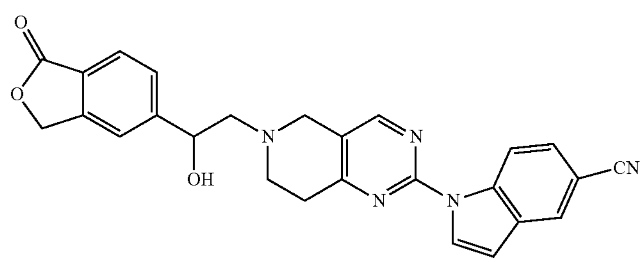 [SMILES: N#Cc1ccc2c(ccn2-c2ncc3c(n2)CCN(CC(O)c2ccc4c(c2)COC4=O)C3)c1] | 1-(6-(2-hydroxy-2-(1-oxo-1,3-dihydro-isobenzofuran-5-yl)ethyl)-5,6,7,8-tetrahydropyrido[4,3-d]pyrimidin-2-yl)-1H-indole-5-carbonitrile (Enantiomer I) |
| 17-II | 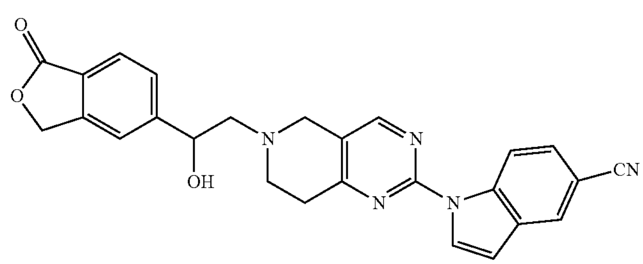 [SMILES: N#Cc1ccc2c(ccn2-c2ncc3c(n2)CCN(CC(O)c2ccc4c(c2)COC4=O)C3)c1] | 1-(6-(2-hydroxy-2-(1-oxo-1,3-dihydro-isobenzofuran-5-yl)ethyl)-5,6,7,8-tetrahydropyrido[4,3-d]pyrimidin-2-yl)-1H-indole-5-carbonitrile (Enantiomer II) |
| 18-II | 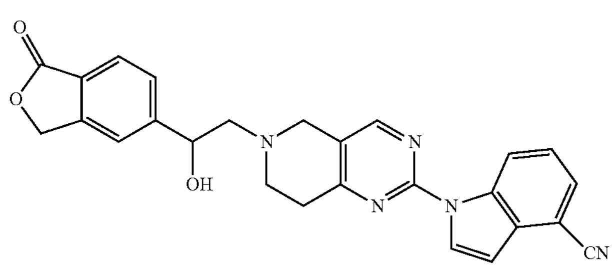 [SMILES: N#Cc1cccc2c1ccn2-c1ncc2c(n1)CCN(CC(O)c1ccc3c(c1)COC3=O)C2] | 1-(6-(2-hydroxy-2-(1-oxo-1,3-dihydro-isobenzofuran-5-yl)ethyl)-5,6,7,8-tetrahydropyrido[4,3-d]pyrimidin-2-yl)-1H-indole-4-carbonitrile (Enantiomer II) |

TABLE 1-continued

| Ex. No. | Structure | Name |
|---|---|---|
| 19-I | 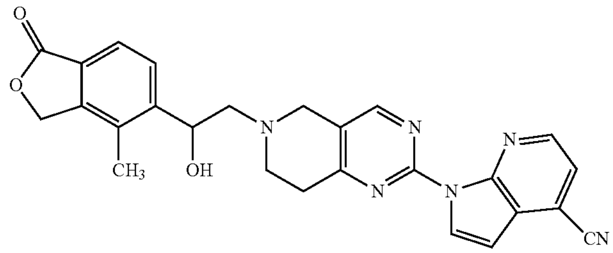 [SMILES: Cc1c(C(O)CN2CCc3nc(-n4ccc5c(C#N)ccnc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-4-carbonitrile (Enantiomer-I) |
| 19-II | 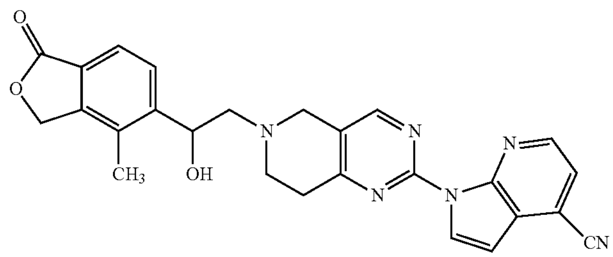 | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-4-carbonitrile (Enantiomer-II) |
| 20 | 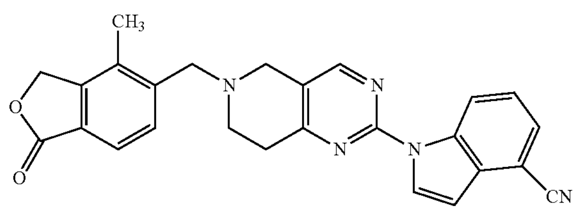 [SMILES: Cc1c(CN2CCc3nc(-n4ccc5c(C#N)cccc54)ncc3C2)ccc2c1COC2=O] | 1-(6-((4-methyl-1-oxo-1,3-dihydro-isobenzofuran-5-yl)methyl)-5,6,7,8-tetrahydropyrido[4,3-d]pyrimidin-2-yl)-1H-indole-4-carbonitrile |
| 21 | 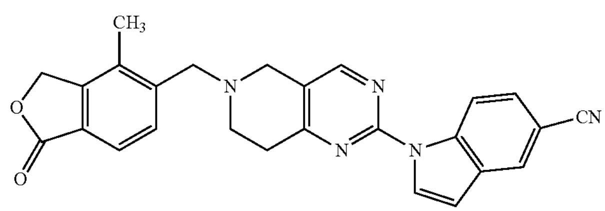 [SMILES: Cc1c(CN2CCc3nc(-n4ccc5cc(C#N)ccc54)ncc3C2)ccc2c1COC2=O] | 1-(6-((4-methyl-1-oxo-1,3-dihydro-isobenzofuran-5-yl)methyl)-5,6,7,8-tetrahydropyrido[4,3-d]pyrimidin-2-yl)-1H-indole-5-carbonitrile |
| 22-I | 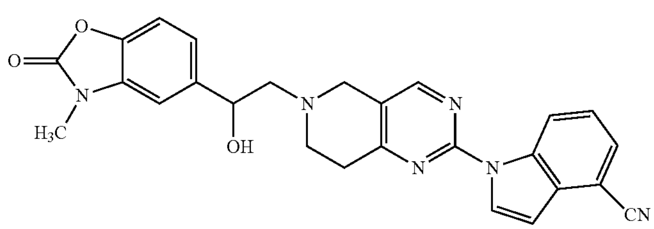 [SMILES: Cn1c(=O)oc2ccc(C(O)CN3CCc4nc(-n5ccc6c(C#N)cccc65)ncc4C3)cc21] | 1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indole-4-carbonitrile (Enantiomer-I) |
| 22-II | 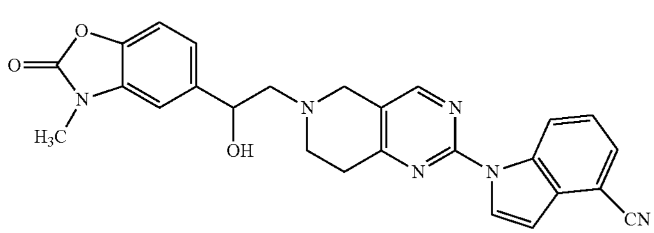 [SMILES: Cn1c(=O)oc2ccc(C(O)CN3CCc4nc(-n5ccc6c(C#N)cccc65)ncc4C3)cc21] | 1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indole-4-carbonitrile (Enantiomer-II) |

TABLE 1-continued

| Ex. No. | Structure | Name |
|---|---|---|
| 23 | 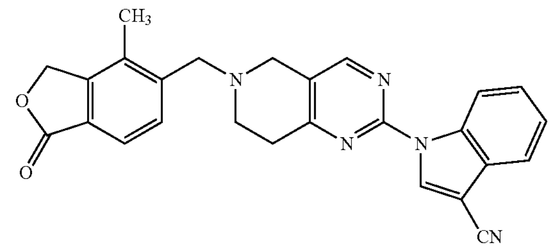 [SMILES: Cc1c(CN2CCc3nc(-n4cc(C#N)c5ccccc54)ncc3C2)ccc2c1COC2=O] | 1-(6-((4-methyl-1-oxo-1,3-dihydro-isobenzofuran-5-yl)methyl)-5,6,7,8-tetrahydropyrido[4,3-d]pyrimidin-2-yl)-1H-indole-3-carbonitrile |
| 24 | 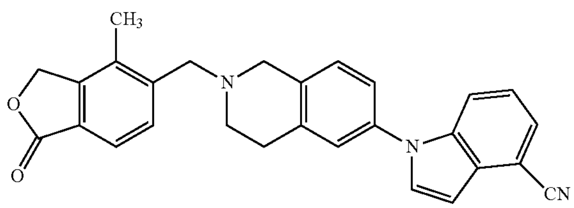 [SMILES: Cc1c(CN2CCc3cc(-n4ccc5c(C#N)cccc54)ccc3C2)ccc2c1COC2=O] | 1-(2-((4-methyl-1-oxo-1,3-dihydro-isobenzofuran-5-yl)methyl)-1,2,3,4-tetrahydroisoquinolin-6-yl)-1H-indole-4-carbonitrile |
| 25-I | 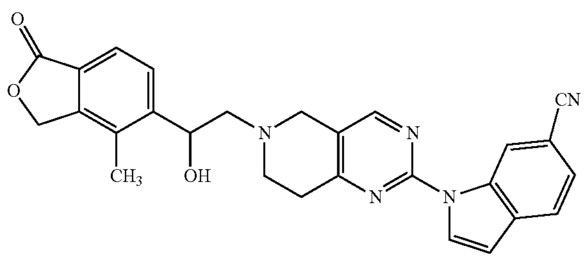 [SMILES: Cc1c(C(O)CN2CCc3nc(-n4ccc5ccc(C#N)cc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-6-carbonitrile (Enantiomer-I) |
| 26 | 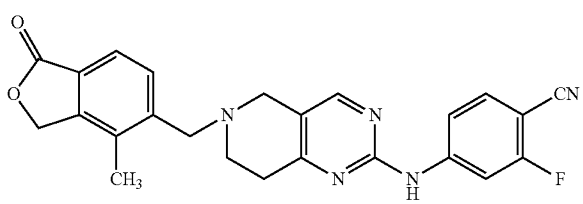 [SMILES: Cc1c(CN2CCc3nc(Nc4ccc(C#N)c(F)c4)ncc3C2)ccc2c1COC2=O] | 2-fluoro-4-((6-((4-methyl-1-oxo-1,3-dihydroisobenzofuran-5-yl)methyl)-5,6,7,8-tetrahydropyrido[4,3-d]pyrimidin-2-yl)amino) benzonitrile |
| 27 | 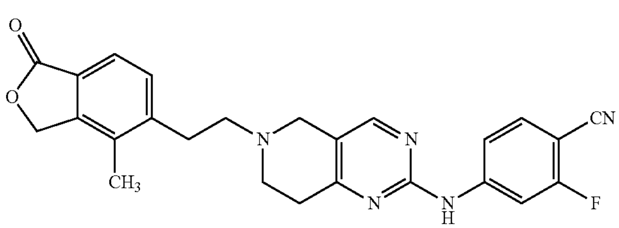 [SMILES: Cc1c(CCN2CCc3nc(Nc4ccc(C#N)c(F)c4)ncc3C2)ccc2c1COC2=O] | 2-fluoro-4-((6-(2-(4-methyl-1-oxo-1,3-dihydroisobenzofuran-5-yl)ethyl)-5,6,7,8-tetrahydropyrido[4,3-d]pyrimidin-2-yl)amino) benzonitrile |
| 28-I | 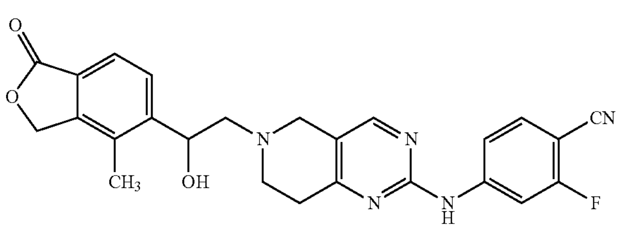 [SMILES: Cc1c(C(O)CN2CCc3nc(Nc4ccc(C#N)c(F)c4)ncc3C2)ccc2c1COC2=O] | 2-fluoro-4-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)benzonitrile (Enantiomer-I) |

TABLE 1-continued

| Ex. No. | Structure | Name |
|---|---|---|
| 28-II | 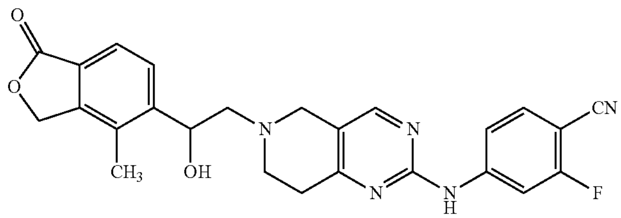 [SMILES: Cc1c(C(O)CN2CCc3nc(Nc4ccc(C#N)c(F)c4)ncc3C2)ccc2c1COC2=O] | 2-fluoro-4-((6-(2-hydroxy-1-(4-methyl-1-oxo-1,3-dihydroisobenzofuran-5-yl)ethyl)-5,6,7,8-tetrahydropyrido[4,3-d]pyrimidin-2-yl)amino)benzonitrile (Enantiomer-II) |
| 29-I | 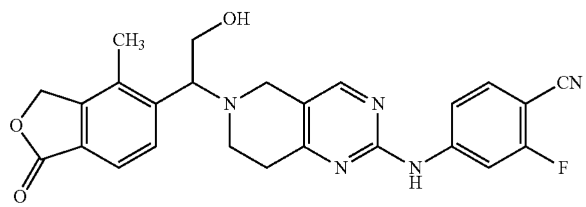 [SMILES: Cc1c(C(CO)N2CCc3nc(Nc4ccc(C#N)c(F)c4)ncc3C2)ccc2c1COC2=O] | 2-fluoro-4-((6-(2-hydroxy-1-(4-methyl-1-oxo-1,3-dihydroisobenzofuran-5-yl)ethyl)-5,6,7,8-tetrahydropyrido[4,3-d]pyrimidin-2-yl)amino)benzonitrile (Enantiomer-I) |
| 29-II | 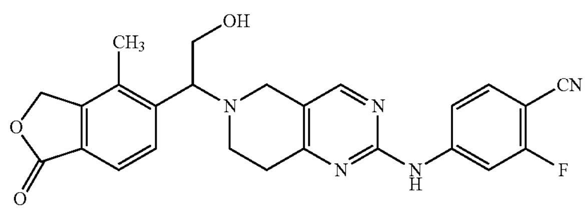 [SMILES: Cc1c(C(CO)N2CCc3nc(Nc4ccc(C#N)c(F)c4)ncc3C2)ccc2c1COC2=O] | 2-fluoro-4-((6-(2-hydroxy-1-(4-methyl-1-oxo-1,3-dihydroisobenzofuran-5-yl)ethyl)-5,6,7,8-tetrahydropyrido[4,3-d]pyrimidin-2-yl)amino)benzonitrile (Enantiomer-II) |
| 30 | 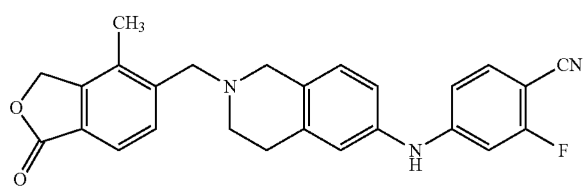 [SMILES: Cc1c(CN2CCc3cc(Nc4ccc(C#N)c(F)c4)ccc3C2)ccc2c1COC2=O] | 2-fluoro-4-((2-((4-methyl-1-oxo-1,3-dihydroisobenzofuran-5-yl)methyl)-1,2,3,4-tetrahydroisoquinolin-6-yl)amino)benzonitrile |
| 31 | 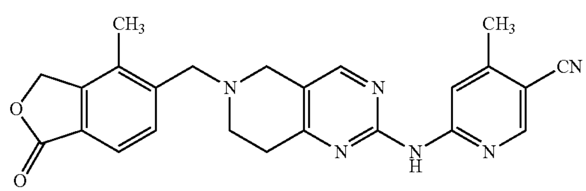 [SMILES: Cc1cc(Nc2ncc3c(n2)CCN(Cc2ccc4c(c2C)COC4=O)C3)ncc1C#N] | 4-methyl-6-((6-((4-methyl-1-oxo-1,3-dihydroisobenzofuran-5-yl)methyl)-5,6,7,8-tetrahydropyrido[4,3-d]pyrimidin-2-yl)amino) nicotinonitrile |
| 32-I | 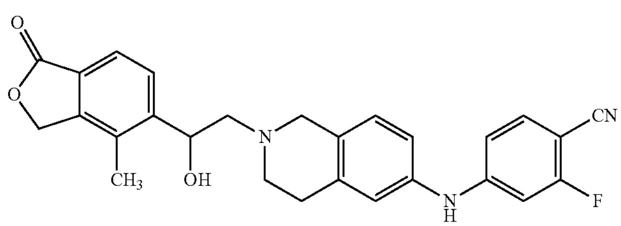 [SMILES: Cc1c(C(O)CN2CCc3cc(Nc4ccc(C#N)c(F)c4)ccc3C2)ccc2c1COC2=O] | 2-fluoro-4-((2-(2-hydroxy-2-(4-methyl-1-oxo-1,3-dihydroisobenzofuran-5-yl)ethyl)-1,2,3,4-tetrahydroisoquinolin-6-yl)amino) benzonitrile (Enantiomer-I) |
| 32-II | 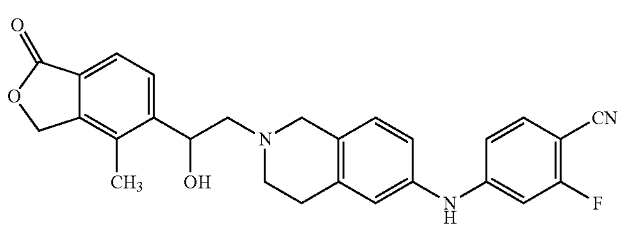 [SMILES: Cc1c(C(O)CN2CCc3cc(Nc4ccc(C#N)c(F)c4)ccc3C2)ccc2c1COC2=O] | 2-fluoro-4-((2-(2-hydroxy-2-(4-methyl-1-oxo-1,3-dihydroisobenzofuran-5-yl)ethyl)-1,2,3,4-tetrahydroisoquinolin-6-yl)amino) benzonitrile (Enantiomer-II) |

TABLE 1-continued

| Ex. No. | Structure | Name |
|---|---|---|
| 33-I | 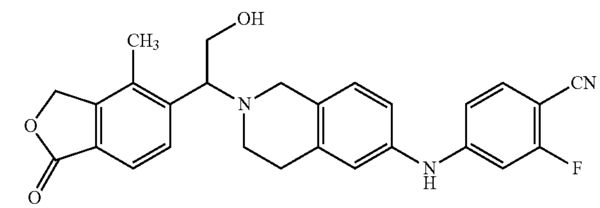 [SMILES: Cc1c(C(CO)N2CCc3cc(Nc4ccc(C#N)c(F)c4)ccc3C2)ccc2c1COC2=O] | 2-fluoro-4-((2-(2-hydroxy-1-(4-methyl-1-oxo-1,3-dihydroisobenzofuran-5-yl)ethyl)-1,2,3,4-tetrahydroisoquinolin-6-yl)amino) benzonitrile (Enantiomer-I) |
| 33-II | 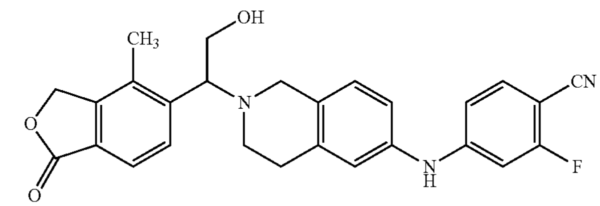 [SMILES: Cc1c(C(CO)N2CCc3cc(Nc4ccc(C#N)c(F)c4)ccc3C2)ccc2c1COC2=O] | 2-fluoro-4-((2-(2-hydroxy-1-(4-methyl-1-oxo-1,3-dihydroisobenzofuran-5-yl)ethyl)-1,2,3,4-tetrahydroisoquinolin-6-yl)amino) benzonitrile (Enantiomer-II) |
| 34 | 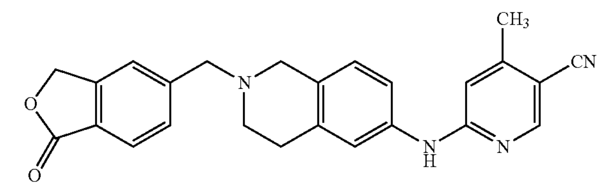 [SMILES: Cc1cc(Nc2ccc3c(c2)CCN(Cc2ccc4c(c2)COC4=O)C3)ncc1C#N] | 4-methyl-6-((2-((1-oxo-1,3-dihydro-isobenzofuran-5-yl)methyl)-1,2,3,4-tetrahydroisoquinolin-6-yl)amino) nicotinonitrile |
| 35-I | 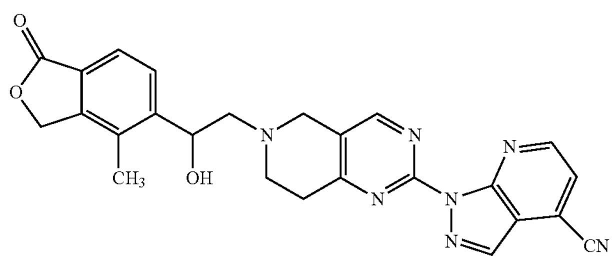 [SMILES: Cc1c(C(O)CN2CCc3nc(-n4ncc5c(C#N)ccnc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-b]pyridine-4-carbonitrile (Enantiomer-I) |
| 35-II | 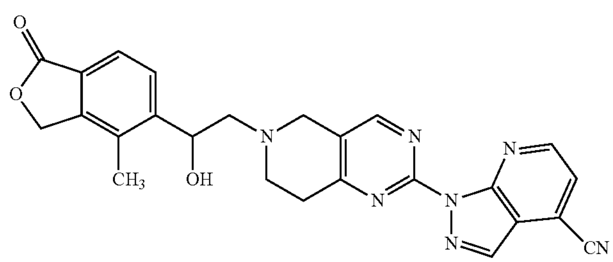 | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-b]pyridine-4-carbonitrile (Enantiomer-II) |
| 36-I | 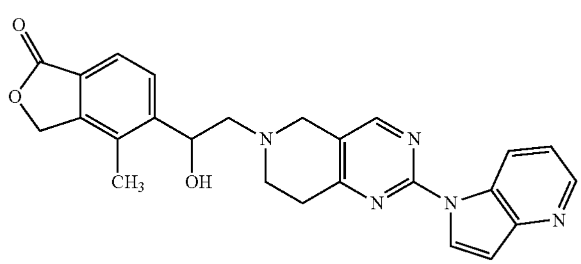 [SMILES: Cc1c(C(O)CN2CCc3nc(-n4ccc5ncccc54)ncc3C2)ccc2c1COC2=O] | 5-(2-(2-(1H-pyrrolo[3,2-b]pyridin-1-yl)-7,8-dihydropyrido[4,3-d]pyrimidin-6(5H)-yl)-1-hydroxyethyl)-4-methyl-isobenzofuran-1(3H)-one (Enantiomer-I) |
| 37 | 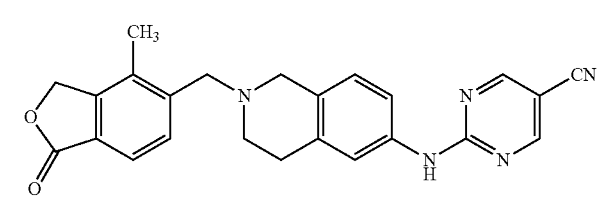 [SMILES: Cc1c(CN2CCc3cc(Nc4ncc(C#N)cn4)ccc3C2)ccc2c1COC2=O] | 2-((2-((4-methyl-1-oxo-1,3-dihydro-isobenzofuran-5-yl)methyl)-1,2,3,4-tetrahydroisoquinolin-6-yl)amino) pyrimidine-5-carbonitrile |

TABLE 1-continued

| Ex. No. | Structure | Name |
|---|---|---|
| 38 | 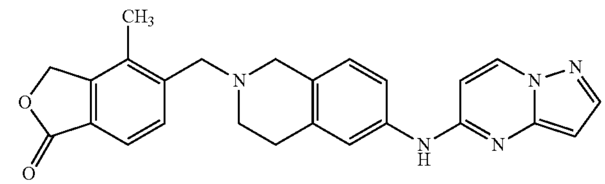 [SMILES: Cc1c(CN2CCc3cc(Nc4ccn5nccc5n4)ccc3C2)ccc2c1COC2=O] | 4-methyl-5-(((6-(pyrazolo[1,5-a]pyrimidin-5-ylamino)-3,4-dihydroisoquinolin-2(1H)-yl)methyl)isobenzofuran-1(3H)-one |
| 39 | 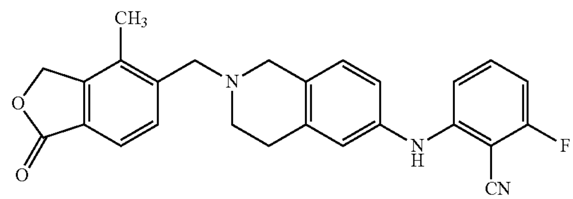 [SMILES: Cc1c(CN2CCc3cc(Nc4cccc(F)c4C#N)ccc3C2)ccc2c1COC2=O] | 2-fluoro-6-((2-((4-methyl-1-oxo-1,3-dihydroisobenzofuran-5-yl)methyl)-1,2,3,4-tetrahydroisoquinolin-6-yl)amino)benzonitrile |
| 40 | 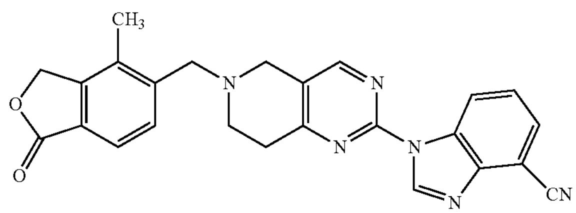 [SMILES: Cc1c(CN2CCc3nc(-n4cnc5c(C#N)cccc54)ncc3C2)ccc2c1COC2=O] | 1-(6-((4-methyl-1-oxo-1,3-dihydro-isobenzofuran-5-yl)methyl)-5,6,7,8-tetrahydropyrido[4,3-d]pyrimidin-2-yl)-1H-benzo[d]imidazole-4-carbonitrile |
| 41-I | 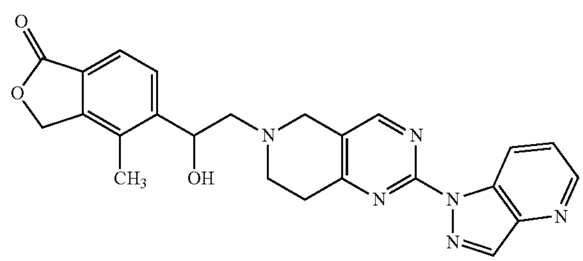 | 5-(2-(2-(1H-pyrazolo[4,3-b]pyridin-1-yl)-7,8-dihydropyrido[4,3-d]pyrimidin-6(5H)-yl)-1-hydroxyethyl)-4-methylisobenzofuran-1(3H)-one (Enantiomer-I) |
| 41-II | 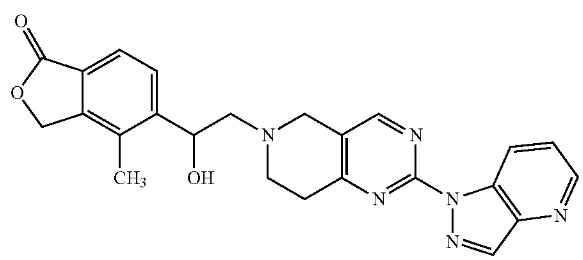 | 5-(2-(2-(1H-pyrazolo[4,3-b]pyridin-1-yl)-7,8-dihydropyrido[4,3-d]pyrimidin-6(5H)-yl)-1-hydroxyethyl)-4-methylisobenzofuran-1(3H)-one (Enantiomer-II) |
| 42-I | 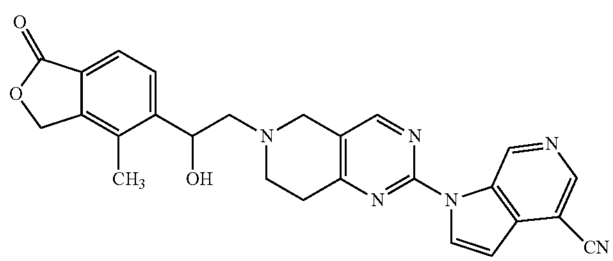 [SMILES: Cc1c(C(O)CN2CCc3nc(-n4ccc5c(C#N)cncc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-c]pyridine-4-carbonitrile (Enantiomer-I) |

TABLE 1-continued

| Ex. No. | Structure | Name |
|---|---|---|
| 42-II | 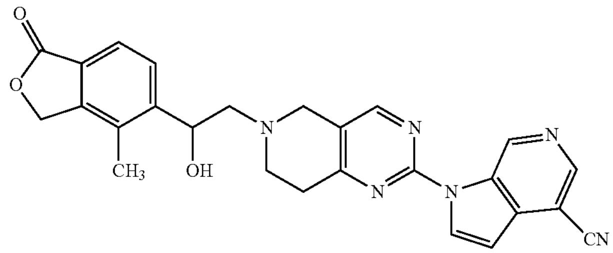 | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-c]pyridine-4-carbonitrile (Enantiomer-II) |
| 43-I | 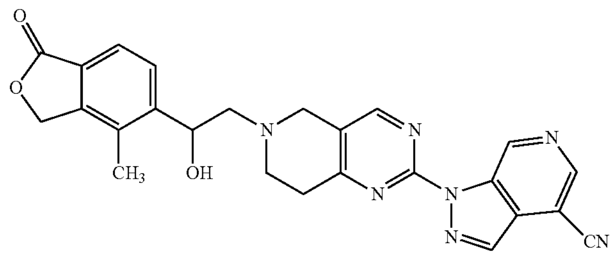 [SMILES: Cc1c(C(O)CN2CCc3nc(-n4ncc5c(C#N)cncc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-c]pyridine-4-carbonitrile (Enantiomer-I) |
| 43-II | 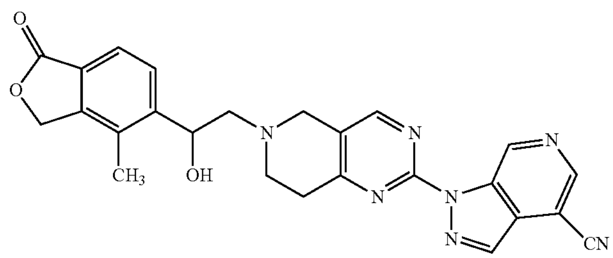 [SMILES: Cc1c(C(O)CN2CCc3nc(-n4ncc5c(C#N)cncc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-c]pyridine-4-carbonitrile (Enantiomer-II) |
| 44-I | 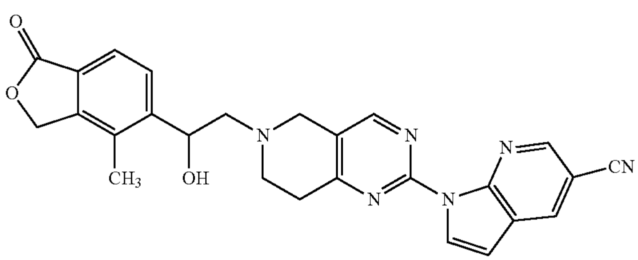 [SMILES: Cc1c(C(O)CN2CCc3nc(-n4ccc5cc(C#N)cnc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-5-carbonitrile (Enantiomer I) |
| 45-I | 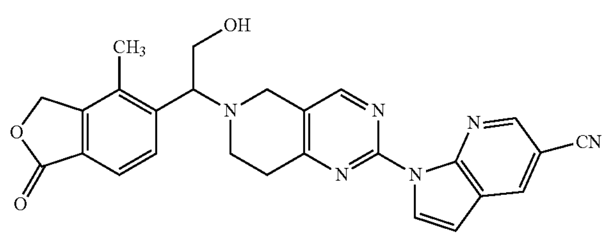 [SMILES: Cc1c(C(CO)N2CCc3nc(-n4ccc5cc(C#N)cnc54)ncc3C2)ccc2c1COC2=O] | 1-(6-(2-hydroxy-1-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-5-carbonitrile (Enantiomer I) |
| 46 | 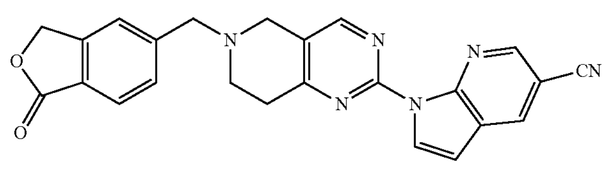 [SMILES: N#Cc1cnc2c(ccn2-c2ncc3c(n2)CCN(Cc2ccc4c(c2)COC4=O)C3)c1] | 1-(6-((1-oxo-1,3-dihydroisobenzofuran-5-yl)methyl)-5,6,7,8-tetrahydropyrido[4,3-d]pyrimidin-2-yl)-1H-pyrrolo[2,3-b]pyridine-5-carbonitrile |

TABLE 1-continued

| Ex. No. | Structure | Name |
|---|---|---|
| 47 | 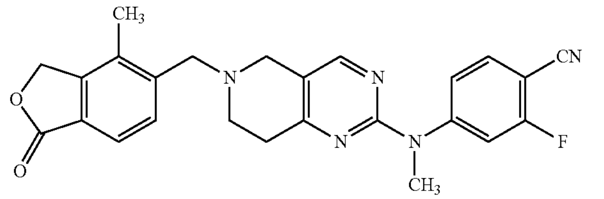 [SMILES: Cc1c(CN2CCc3nc(N(C)c4ccc(C#N)c(F)c4)ncc3C2)ccc2c1COC2=O] | 2-fluoro-4-(methyl(6-((4-methyl-1-oxo-1,3-dihydroisobenzofuran-5-yl)methyl)-5,6,7,8-tetrahydropyrido[4,3-d]pyrimidin-2-yl)amino)benzonitrile |
| 48 | 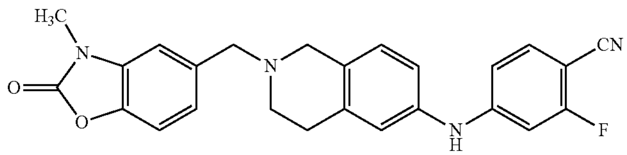 [SMILES: Cn1c(=O)oc2ccc(CN3CCc4cc(Nc5ccc(C#N)c(F)c5)ccc4C3)cc21] | 2-fluoro-4-((2-((3-methyl-2-oxo-2,3-dihydrobenzo[d]oxazol-5-yl)methyl)-1,2,3,4-tetrahydroisoquinolin-6-yl)amino)benzonitrile |
| 49 | 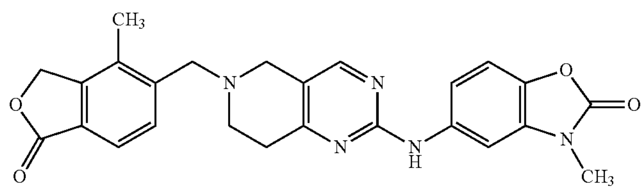 [SMILES: Cc1c(CN2CCc3nc(Nc4ccc5oc(=O)n(C)c5c4)ncc3C2)ccc2c1COC2=O] | 3-methyl-5-((6-((4-methyl-1-oxo-1,3-dihydroisobenzofuran-5-yl)methyl)-5,6,7,8-tetrahydropyrido[4,3-d]pyrimidin-2-yl)amino)benzo[d]oxazol-2(3H)-one |
| 50 | 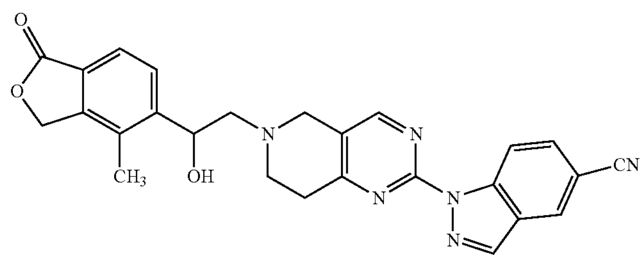 [SMILES: Cc1c(C(O)CN2CCc3nc(-n4ncc5cc(C#N)ccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-5-carbonitrile (Enantiomer I) |
| -51-I | 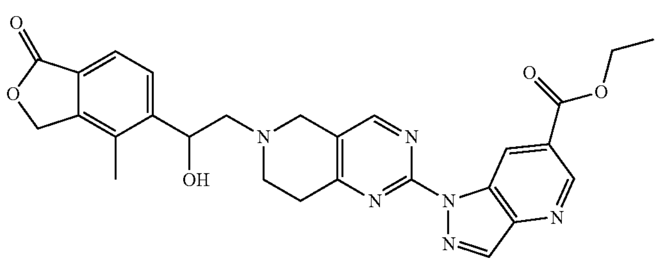 [SMILES: CCOC(=O)c1cnc2cnn(-c3ncc4c(n3)CCN(CC(O)c3ccc5c(c3C)COC5=O)C4)c2c1] | ethyl 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[4,3-b]pyridine-6-carboxylate (Enantiomer-I) |
| 52-I | 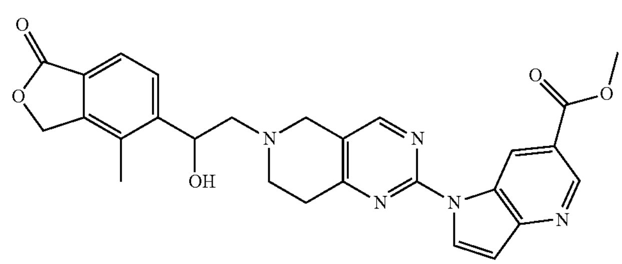 [SMILES: COC(=O)c1cnc2ccn(-c3ncc4c(n3)CCN(CC(O)c3ccc5c(c3C)COC5=O)C4)c2c1] | methyl 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[3,2-b]pyridine-6-carboxylate (Enantiomer-I) |

TABLE 1-continued

| Ex. No. | Structure | Name |
|---|---|---|
| 53-I | 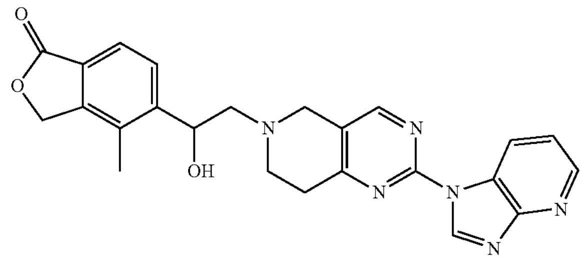 [SMILES: Cc1c(C(O)CN2CCc3nc(-n4cnc5ncccc54)ncc3C2)ccc2c1COC2=O] | 5-(2-(2-(1H-imidazo[4,5-b]pyridin-1-yl)-7,8-dihydropyrido[4,3-d]pyrimidin-6(5H)-yl)-1-hydroxyethyl)-4-methylisobenzofuran-1(3H)-one (Enantiomer-I) |
| 54-I | 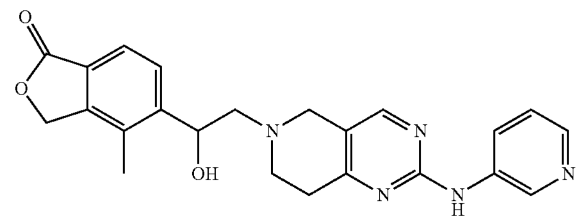 [SMILES: Cc1c(C(O)CN2CCc3nc(Nc4cccnc4)ncc3C2)ccc2c1COC2=O] | 5-(1-hydroxy-2-(2-(pyridin-3-ylamino)-7,8-dihydropyrido[4,3-d]pyrimidin-6(5H)-yl)ethyl)-4-methylisobenzofuran-1(3H)-one (Enantiomer-I) |
| 55-I | 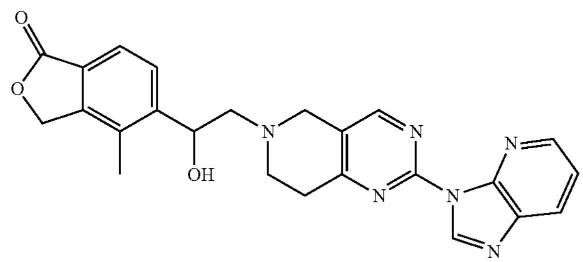 [SMILES: Cc1c(C(O)CN2CCc3nc(-n4cnc5cccnc54)ncc3C2)ccc2c1COC2=O] | 5-(2-(2-(3H-imidazo[4,5-b]pyridin-3-yl)-7,8-dihydropyrido[4,3-d]pyrimidin-6(5H)-yl)-1-hydroxyethyl)-4-methylisobenzofuran-1(3H)-one (Enantiomer-I) |
| 56-I | 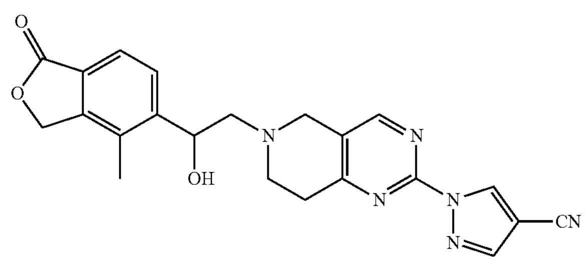 [SMILES: Cc1c(C(O)CN2CCc3nc(-n4cc(C#N)cn4)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazole-4-carbonitrile (Enantiomer-I) |
| 57-I | 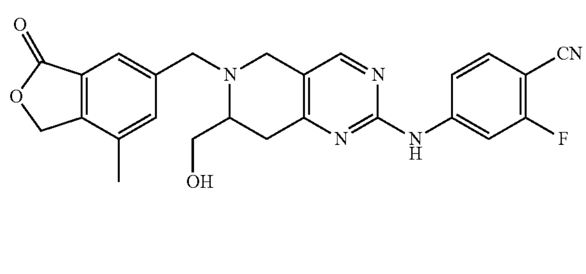 [SMILES: Cc1cc(CN2Cc3cnc(Nc4ccc(C#N)c(F)c4)nc3CC2CO)cc2c1COC2=O] | 2-fluoro-4-((7-(hydroxymethyl)-6-((4-methyl-1-oxo-1,3-dihydroisobenzofuran-5-yl)methyl)-5,6,7,8-tetrahydropyrido[4,3-d]pyrimidin-2-yl)amino)benzonitrile (Enantiomer-I) |
| 57-II | 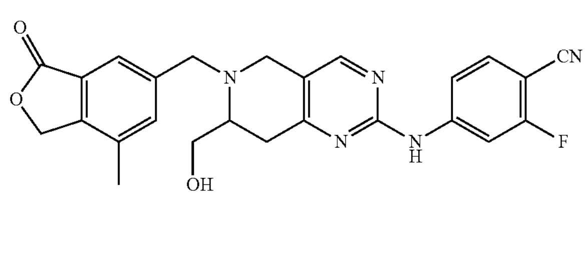 [SMILES: Cc1cc(CN2Cc3cnc(Nc4ccc(C#N)c(F)c4)nc3CC2CO)cc2c1COC2=O] | 2-fluoro-4-((7-(hydroxymethyl)-6-((4-methyl-1-oxo-1,3-dihydroisobenzofuran-5-yl)methyl)-5,6,7,8-tetrahydropyrido[4,3-d]pyrimidin-2-yl)amino)benzonitrile (Enantiomer-II) |

TABLE 1-continued

| Ex. No. | Structure | Name |
|---|---|---|
| 58-I | 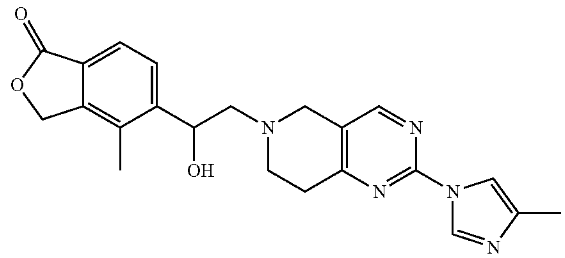 [SMILES: Cc1cn(-c2ncc3c(n2)CCN(CC(O)c2ccc4c(c2C)COC4=O)C3)cn1] | 5-(1-hydroxy-2-(2-(4-methyl-1H-imidazol-1-yl)-7,8-dihydropyrido[4,3-d]pyrimidin-6(5H)-yl)ethyl)-4-methyl isobenzofuran-1(3H)-one (Enantiomer-I) |
| 59-I | 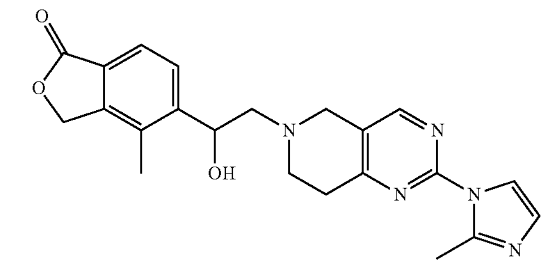 [SMILES: Cc1c(C(O)CN2CCc3nc(-n4ccnc4C)ncc3C2)ccc2c1COC2=O] | 5-(1-hydroxy-2-(2-(2-methyl-1H-imidazol-1-yl)-7,8-dihydropyrido[4,3-d]pyrimidin-6(5H)-yl)ethyl)-4-methyl isobenzofuran-1(3H)-one (Enantiomer-I) |
| 60-I | 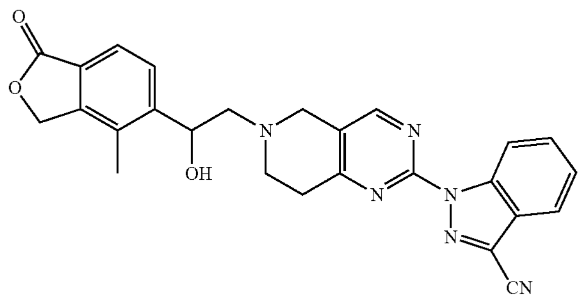 [SMILES: Cc1c(C(O)CN2CCc3nc(-n4nc(C#N)c5ccccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-3-carbonitrile (Enantiomer-I) |
| 61-I | 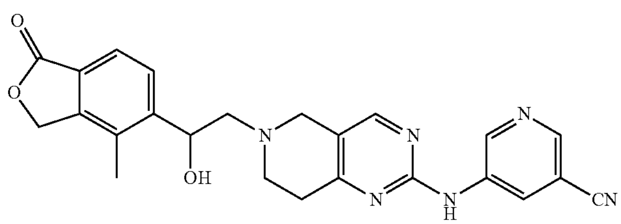 [SMILES: Cc1c(C(O)CN2CCc3nc(Nc4cncc(C#N)c4)ncc3C2)ccc2c1COC2=O] | 5-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)nicotinonitrile (Enantiomer-I) |
| 62-I | 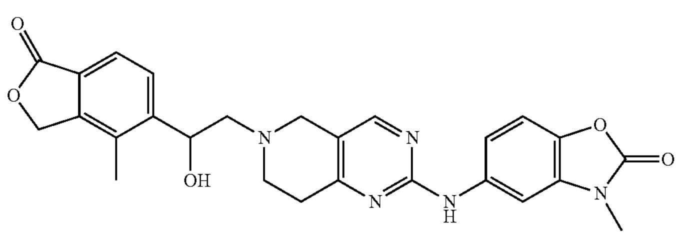 [SMILES: Cc1c(C(O)CN2CCc3nc(Nc4ccc5oc(=O)n(C)c5c4)ncc3C2)ccc2c1COC2=O] | 5-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)-3-methylbenzo[d]oxazol-2(3H)-one (Enantiomer-I) |
| 63-I | 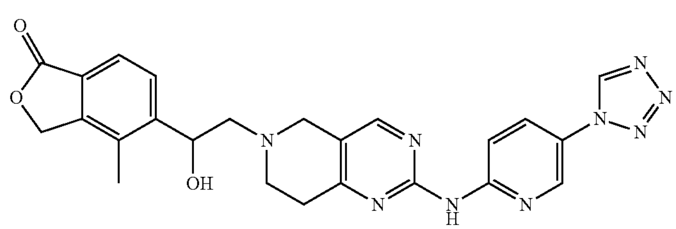 [SMILES: Cc1c(C(O)CN2CCc3nc(Nc4ccc(-n5cnnn5)cn4)ncc3C2)ccc2c1COC2=O] | 5-(2-(2-((5-(1H-tetrazol-1-yl)pyridine-2-yl)amino)-7,8-dihydropyrido[4,3-d]pyrimidin-6(5H)-yl)-1-hydroxyethyl)-4-methylisobenzofuran-1(3H)-one (Enantiomer-I) |

TABLE 1-continued

| Ex. No. | Structure | Name |
|---|---|---|
| 64-I | 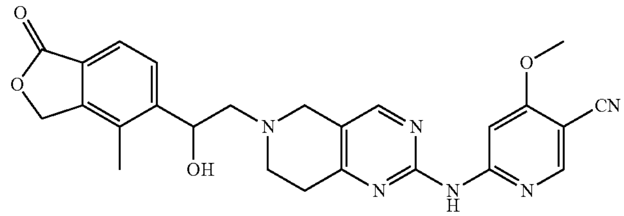 [SMILES: COc1cc(Nc2ncc3c(n2)CCN(CC(O)c2ccc4c(c2C)COC4=O)C3)ncc1C#N] | 6-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)-4-methoxynicotinonitrile (Enantiomer-I) |
| 65-I | 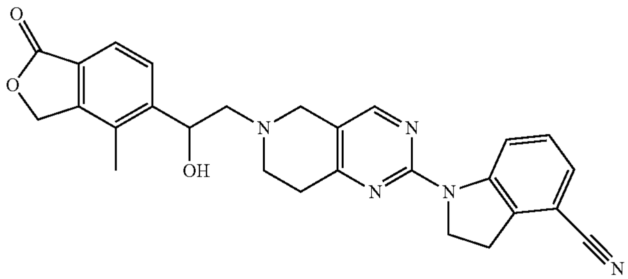 [SMILES: Cc1c(C(O)CN2CCc3nc(N4CCc5c(C#N)cccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)indoline-4-carbonitrile (Enantiomer-I) |
| 65-II | 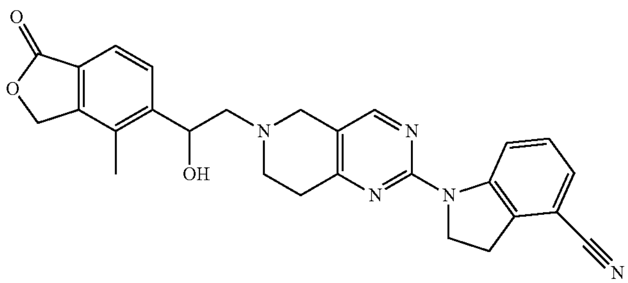 [SMILES: Cc1c(C(O)CN2CCc3nc(N4CCc5c(C#N)cccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)indoline-4-carbonitrile (Enantiomer-II) |
| 66-I | 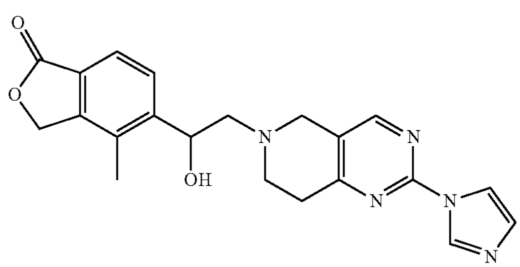 [SMILES: Cc1c(C(O)CN2CCc3nc(-n4ccnc4)ncc3C2)ccc2c1COC2=O] | 5-(2-(2-(1H-imidazol-1-yl)-7,8-dihydropyrido[4,3-d]pyrimidin-6(5H)-yl)-1-hydroxyethyl)-4-methylisobenzofuran-1(3H)-one (Enantiomer-I) |
| 67-I | 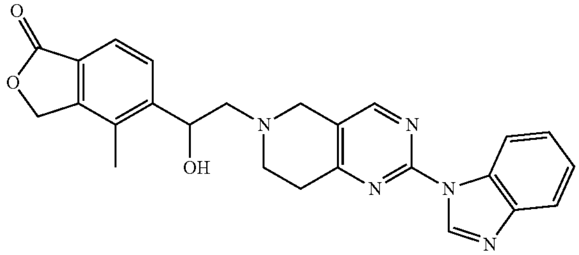 [SMILES: Cc1c(C(O)CN2CCc3nc(-n4cnc5ccccc54)ncc3C2)ccc2c1COC2=O] | 5-(2-(2-(1H-benzo[d]imidazol-1-yl)-7,8-dihydropyrido[4,3-d]pyrimidin-6(5H)-yl)-1-hydroxyethyl)-4-methylisobenzofuran-1(3H)-one (Enantiomer-I) |

TABLE 1-continued

| Ex. No. | Structure | Name |
|---|---|---|
| 68-I | 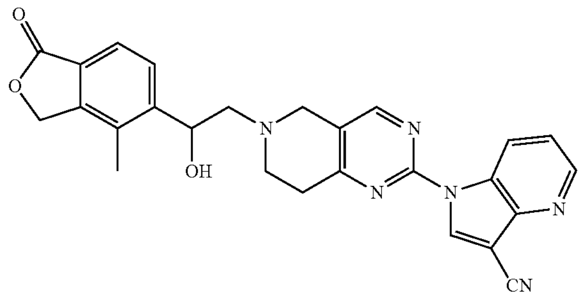 [SMILES: Cc1c(C(O)CN2CCc3nc(-n4cc(C#N)c5ncccc54)ncc3C2)ccc2c1COC2=O] | 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[3,2-b]pyridine-3-carbonitrile (Enantiomer-I) |

TABLE 2

| Ex. No. | LCMS (M + H)+ | HPLC/LCMS Method: RT (min.), Purity | NMR |
|---|---|---|---|
| 8-II | 466.1 | A: 2.07, 94.62%<br>B: 1.33, 95.26%<br>XX: 12.09<br>100% ee | $^1$H NMR (400 MHz, DMSO-d$_6$) δ ppm 2.31 (s, 3 H), 2.66-2.77 (m, 2 H), 2.99-3.03 (m, 4 H), 3.80-3.90 (m, 2 H), 5.20-5.23 (m, 1 H), 5.40 (d, J = 3.2 Hz, 2 H), 5.45 (d, J = 4.0 Hz, 1 H), 7.43 (t, J = 7.6 Hz, 1 H), 7.51 (t, J = 7.6 Hz, 1 H), 7.70 (d, J = 8.0 Hz, 1 H), 7.73-7.76 (m, 2 H), 8.68 (s, 1 H), 8.81 (d, J = 8.4 Hz, 1 H), 9.07 (s, 1 H). |
| 9-II | 466.2 | A: 2.23, 97.28%<br>B: 1.36, 96.86%<br>XVIII: 11.63<br>96% ee | $^1$H NMR (400 MHz, DMSO-d$_6$) δ ppm 2.32 (s, 3 H), 2.88-3.00 (m, 4 H), 3.71-3.77 (m, 2 H), 3.93-4.02 (m, 3 H), 4.91 (t, J = 1.6 Hz, 1 H), 5.42 (s, 2 H), 7.42 (t, J = 7.6 Hz, 1 H), 7.50 (t, J = 7.6 Hz, 1 H), 7.66-7.74 (m, 3 H), 8.63 (s, 1 H), 8.79 (d, J = 8.8 Hz, 1 H), 9.05 (s, 1 H). |
| 11 | 423.1 | A: 1.13, 97.1%<br>B: 1.84 100% | $^1$H NMR (400 MHz, DMSO-d$_6$) δ ppm 2.89-2.96 (m, 2 H), 3.04-3.11 (m, 2 H), 3.70 (s, 2 H), 3.92 (s, 2 H), 5.42 (s, 2 H), 7.63 (d, J = 8.3 Hz, 1 H), 7.72 (s, 1 H), 7.85 (d, J = 8.1 Hz, 1 H), 7.92-7.98 (m, 1 H), 8.54 (s, 1 H), 8.61 (s, 1 H), 8.67 (s, 1 H), 8.78 (d, J = 9.0 Hz, 1 H) |
| 12-I | 467.2, | E: 2.08, 99.72%<br>D: 6.42, 99.37%<br>XXIV: 20.55<br>99.08 ee | $^1$H NMR (400 MHz, DMSO-d$_6$) δ ppm 2.30 (s, 3 H), 2.65-2.81 (m, 2 H), 2.96-3.09 (m, 4 H), 3.75-3.98 (m, 2H), 5.15-5.27 (m, 1 H), 5.40 (d, J = 3.2 Hz, 2 H), 5.46 (d, J = 4.2 Hz, 1 H), 7.70 (d, J = 8.4 Hz 1 H), 7.73-7.81 (m, 2 H), 7.95 (d, J = 6.4 Hz, 1 H), 8.68 (s, 1 H), 8.71 (s, 1 H), 9.00 (d, J = 8.6 Hz, 1 H) |
| 12-II | 467.1 | A: 1.26, 100%<br>B: 1.77, 100%<br>XXIV: 17.89<br>97.04% | $^1$H NMR (400 MHz, DMSO-d$_6$) δ ppm 2.30 (s, 3 H), 2.65-2.81 (m, 2 H), 2.96-3.09 (m, 4 H), 3.75-3.98 (m, 2 H), 5.15-5.27 (m, 1 H), 5.40 (d, J = 3.2 Hz, 2 H), 5.46 (d, J = 4.2 Hz, 1 H), 7.70 (d, J = 8.4 Hz 1 H), 7.73-7.81 (m, 2 H), 7.95 (d, J = 6.4 Hz, 1 H), 8.68 (s, 1 H), 8.71 (s, 1 H), 9.00 (d, J = 8.6 Hz, 1 H) |
| 13 | 437.2 | A: 1.15, 99.23%<br>B: 1.811, 97.92% | $^1$H NMR (400 MHz, DMSO-d$_6$) δ ppm 2.34 (s, 3 H), 2.93 (t, J = 5.4 Hz, 2 H), 3.05 (t, J = 5.6 Hz, 2 H), 3.71 (s, 2 H), 3.87 (s, 2 H), 5.42 (s, 2 H), 7.59-7.64 (m, 1 H), 7.69 (d, J = 7.8 Hz, 1 H), 7.94 (d, J = 8.8 Hz, 1 H), 8.53 (s, 1 H), 8.60 (s, 1 H), 8.67 (s, 1 H), 8.78 (d, J = 8.8 Hz, 1 H) |
| 14 | 456.2 | A: 1.29, 98.27%<br>B: 2.14, 99.43% | $^1$H NMR (400 MHz, DMSO-d$_6$) δ ppm 2.30 (s, 3 H), 2.64-2.72 (m, 2 H), 2.73-2.79 (m, 2 H), 3.25 (s, 3 H), 3.50 (s, 2 H), 3.74 (s, 2 H), 5.41 (s, 2 H), 6.69-6.74 (m, 1 H), 6.78-6.83 (m, 2 H), 6.84-6.90 (m, 2 H), 7.16 (d, J = 8.8 Hz, 1 H), 7.58 (d, J = 8.1 Hz, 1 H), 7.67 (d, J = 8.1 Hz, 1 H), 8.00 (s, 1 H) |
| 15 | 427.1 | A: 1.15, 100%<br>B: 1.80, 100% | $^1$H NMR (400 MHz, DMSO-d$_6$) δ ppm 2.12 (s, 3 H), 4.91 (d, J = 4.4 Hz, 2 H), 6.81 (d, J = 2.8 Hz, 1 H), 7.27-7.30 (m, 2 H), 7.32-7.55 (m, 6 H), 7.58-7.81 (m, 1 H), 7.90 (d, J = 2.4 Hz, 1 H), 8.38-8.39 (m, 1 H), 8.81 (t, J = 6.8 Hz, 1 H), 8.86 (d, J = 2.4 Hz, 2 H), 9.08 (d, J = 2.0 Hz, 1 H), 10.29 (m, 1 H). |

TABLE 2-continued

| Ex. No. | LCMS (M + H)+ | HPLC/LCMS Method: RT (min.), Purity | NMR |
|---|---|---|---|
| 16-I | E: 2.77, 466.2 | C: 6.47, 97.33%<br>D: 8.34, 98.37%<br>V: 16.32<br>99.38% ee | ¹H NMR (400 MHz, DMSO-d₆) δ ppm 2.32 (s, 3 H), 2.66-2.74 (m, 2 H), 2.99 (t, J = 4.8 Hz, 4 H), 3.83 (d, J = 8.8 Hz, 2 H), 5.23 (t, J = 4.0 Hz, 1 H), 5.40 (d, J = 2.8 Hz, 2 H), 5.44 (d, J = 4.0 Hz, 1 H), 6.90 (dd, J = 3.6, 0.8 Hz, 1 H), 7.68-7.76 (m, 3 H), 8.20 (d, J = 1.2 Hz, 1 H), 8.42 (d, J = 3.6 Hz, 1 H), 8.63 (s, 1 H), 8.88 (d, J = 8.8 Hz, 1 H). |
| 16-II | E: 2.78, 466.2 | C: 6.14, 96.13%<br>Q: 6.82, 97.92%<br>V: 18.57<br>98% ee | ¹H NMR (400 MHz, DMSO-d₆) δ ppm 2.32 (s, 3 H), 2.66-2.74 (m, 2 H), 2.99 (t, J = 4.8 Hz, 4 H), 3.83 (d, J = 8.8 Hz, 2 H), 5.23 (t, J = 4.0 Hz, 1 H), 5.40 (d, J = 2.8 Hz, 2 H), 5.44 (d, J = 4.0 Hz, 1 H), 6.90 (dd, J = 3.6, 0.8 Hz, 1 H), 7.68-7.76 (m, 3 H), 8.20 (d, J = 1.2 Hz, 1 H), 8.42 (d, J = 3.6 Hz, 1 H), 8.63 (s, 1 H), 8.88 (d, J = 8.8 Hz, 1 H). |
| 17-I | E: 2.63, 452.2 | C: 5.94, 93.70%<br>Q: 6.58, 92.80%<br>XVI: 21.16<br>100% ee | ¹H NMR (400 MHz, DMSO-d₆) δ ppm 2.74-2.79 (m, 2 H), 2.93-3.00 (m, 4 H), 3.80 (s, 1 H), 5.01 (t, J = 4.0 Hz, 1 H), 5.40 (s, 2 H), 5.54 (d, J = 4.0 Hz, 1 H), 6.90 (dd, J = 4.0, 0.8 Hz, 1 H), 7.63 (d, J = 8.0 Hz, 1 H), 7.68 (d, J = 1.6 Hz, 2 H), 7.70 (t, J = 1.6 Hz, 1 H), 7.81 (d, J = 8.0 Hz, 1 H), 8.20 (d, J = 1.2 Hz, 1 H), 8.41 (d, J = 3.6 Hz, 1 H), 8.61 (s, 1 H), 8.87 (d, J = 8.0 Hz, 1 H). |
| 17-II | E: 2.64, 452.2 | C: 6.75, 96.04%<br>D: 7.39, 99.07%<br>XVI: 14.96<br>100% ee | ¹H NMR (400 MHz, DMSO-d₆) δ ppm 2.74-2.79 (m, 2 H), 2.93-3.00 (m, 4 H), 3.80 (s, 1 H), 5.01 (t, J = 4.0 Hz, 1 H), 5.40 (s, 2 H), 5.54 (d, J = 4.0 Hz, 1 H), 6.90 (dd, J = 4.0, 0.8 Hz, 1 H), 7.63 (d, J = 8.0 Hz, 1 H), 7.68 (d, J = 1.6 Hz, 2 H), 7.70 (t, J = 1.6 Hz, 1 H), 7.81 (d, J = 8.0 Hz, 1 H), 8.20 (d, J = 1.2 Hz, 1 H), 8.41 (d, J = 3.6 Hz, 1 H), 8.61 (s, 1 H), 8.87 (d, J = 8.0 Hz, 1 H) |
| 18-II | E: 2.74, 452.2 | C: 6.03, 94.58%<br>D: 7.79, 96.34%<br>XVI: 12.7,<br>100% ee | ¹H NMR (400 MHz, DMSO-d₆) δ ppm 2.74-2.82 (m, 2 H), 2.94-3.00 (m, 4 H), 3.80 (s, 2 H), 5.02 (s, 1 H), 5.40 (s, 2 H), 5.61 (s, 1 H), 6.91 (dd, J = 3.6, 0.8 Hz, 1 H), 7.47-7.51 (m, 1 H), 7.63 (d, J = 8.0 Hz, 1 H), 7.70 (s, 1 H), 7.75 (dd, J = 8.0, 0.8 Hz, 1 H), 7.81 (d, J = 8.0 Hz, 1 H), 8.50 (d, J = 3.6 Hz, 1 H), 8.62 (s, 1 H), 9.06 (d, J = 8.0 Hz, 1 H) |
| 19-I | 467.2 | A: 1.22, 100%<br>B: 1.72, 100%<br>X: 17.71<br>99.50% ee | ¹H NMR (400 MHz, DMSO-d₆) δ ppm 2.32 (s, 3 H), 2.66-2.78 (m, 2 H), 3.00 (s, 4 H), 3.87 (d, J = 9.6 Hz, 2 H), 5.23 (t, J = 3.6 Hz, 1 H), 5.41 (d, J = 2.8 Hz, 2 H), 5.46 (d, J = 4.0 Hz, 1 H), 7.71 (d, J = 8.0 Hz, 1 H), 7.75 (s, 1 H), 7.78 (d, J = 4.8 Hz, 2 H), 8.46 (d, J = 8.0 Hz, 1 H), 8.61 (d, J = 4.8 Hz, 1 H), 8.70 (s, 1 H). |
| 19-II | 467.2 | A: 1.23, 100%<br>B: 1.70, 99.33%<br>X: 15.12<br>97.42% ee | ¹H NMR (400 MHz, DMSO-d₆) δ ppm 2.32 (s, 3 H), 2.66-2.78 (m, 2 H), 3.00 (s, 4 H), 3.87 (d, J = 9.6 Hz, 2 H), 5.23 (t, J = 3.6 Hz, 1 H), 5.41(d, J = 2.8 Hz, 2 H), 5.46 (d, J = 4.0 Hz, 1 H), 7.71 (d, J = 8.0 Hz, 1 H), 7.75 (s, 1 H), 7.78 (d, J = 4.8 Hz, 2 H), 8.46 (d, J = 8.0 Hz, 1 H), 8.61 (d, J = 4.8 Hz, 1 H), 8.70 (s, 1 H). |
| 20 | 436.1 | A: 1.28, 98.93%<br>B: 2.27, 97.62% | ¹H NMR (400 MHz, DMSO-d₆) δ ppm 2.34 (s, 3 H), 2.67 (t, J = 1.6 Hz, 2 H), 2.92 (t, J = 5.6 Hz, 2 H), 3.68 (s, 2 H), 3.87 (s, 2 H), 5.42 (s, 2 H), 6.91 (dd, J = 3.2, 0.8 Hz, 1 H), 7.49 (t, J = 7.2 Hz, 2 H), 7.62 (d, J = 8.0 Hz, 1 H), 7.70 (d, J = 8.0 Hz, 1 H), 7.75 (dd, J = 8.0, 0.8 Hz, 1 H), 8.50 (d, J = 3.6 Hz, 1 H), 8.62 (s, 1 H). |
| 21 | 436.1 | A: 1.48, 99.01%<br>B: 2.33, 98.99% | ¹H NMR (400 MHz, DMSO-d₆) δ ppm 2.34 (s, 3 H), 2.67 (t, J = 1.6 Hz, 2 H), 2.92 (t, J = 5.6 Hz, 2 H), 3.68 (s, 2 H), 3.87 (s, 2 H), 5.42 (s, 2 H), 6.90 (d, J = 3.6 Hz, 1 H), 7.49 (t, J = 7.2 Hz, 2 H), 7.62 (d, J = 8.0 Hz, 1 H), 8.20 (s, 1 H), 8.41 (d, J = 3.6 Hz, 1 H), 8.61 (s, 1 H), 8.87 (d, J = 8.8 Hz, 1 H). |
| 22-I | E: 2.75, 467.2 | C: 5.42, 98.68%<br>D: 7.63, 98.54%<br>XXI: 3.08<br>100% ee | ¹H NMR (400 MHz, DMSO-d₆) δ ppm 2.66-2.80 (m, 2 H), 2.92-3.00 (m, 4 H), 3.41 (s, 3 H), 3.80 (s, 2 H), 4.88-4.92 (m, 1 H), 5.32 (d, J = 4.0 Hz, 1 H), 6.90 (dd, J = 3.6, 0.8 Hz, 1 H), 7.16 (dd, J = 8.0, 1.6 Hz, 1 H), 7.25 (s, 1 H), 7.28 (d, J = 4.4 Hz, 1 H), 7.49 (t, J = 8.0 Hz, 1 H), 7.73 (dd, J = 8.0, 0.8 Hz, 1 H), 8.50 (d, J = 4.0 Hz, 1 H), 8.62 (s, 1 H), 8.05 (d, J = 8.8 Hz, 1 H). |
| 22-II | E: 2.75, 467.2 | C: 5.36, 98.52%<br>D: 7.57, 97.80%<br>XXI: 5.03<br>94.54% ee | ¹H NMR (400 MHz, DMSO-d₆) δ ppm 2.66-2.80 (m, 2 H), 2.92-3.00 (m, 4 H), 3.41 (s, 3 H), 3.80 (s, 2 H), 4.88-4.92 (m, 1 H), 5.32 (d, J = 4.0 Hz, 1 H), 6.90 (dd, J = 3.6, 0.8 Hz, 1 H), 7.16 (dd, J = |

TABLE 2-continued

| Ex. No. | LCMS (M + H)+ | HPLC/LCMS Method: RT (min.), Purity | NMR |
|---|---|---|---|
| | | | 8.0, 1.6 Hz, 1 H), 7.25 (s, 1 H), 7.28 (d, J = 4.4 Hz, 1 H), 7.49 (t, J = 8.0 Hz, 1 H), 7.73 (dd, J = 8.0, 0.8 Hz, 1 H), 8.50 (d, J = 4.0 Hz, 1 H), 8.62 (s, 1 H), 8.05 (d, J = 8.8 Hz, 1 H). |
| 23 | 436.1, | A: 1.38, 100%<br>B: 2.83, 100% | $^1$H NMR (400 MHz, DMSO-$d_6$) δ ppm 2.32 (s, 3 H), 2.94-3.33 (m, 4 H), 3.37-3.70 (m, 4 H), 5.42 (s, 2 H), 7.43 (t, J = 6.8 Hz, 1 H), 7.48-7.53 (m, 1 H), 7.63-7.75 (m, 3 H), 8.67 (s, 1 H), 8.80 (d, J = 8.4 Hz, 1 H), 9.06 (s, 1 H). |
| 24 | 434.1 | A: 1.55, 99.16%<br>B: 2.558, 97.87% | $^1$H NMR (400 MHz, DMSO-$d_6$) δ ppm 2.32 (s, 3 H), 2.78 (t, J = 5.6 Hz, 2 H), 2.93 (t, J = 52 Hz, 2 H), 3.68 (s, 2 H), 3.81 (s, 2 H), 5.42 (s, 2 H), 6.83 (d, J = 3.2 Hz, 1 H), 7.26 (d, J = 7.6 Hz, 1 H), 7.32-7.36 (m, 3 H), 7.62 (d, J = 8.0 Hz, 1 H), 7.65-7.69 (m, 2 H), 7.86 (d, J = 8.0 Hz, 1 H), 7.90 (d, J = 3.2 Hz, 1 H). |
| 25-I | 466.2 | A: 1.47, 100%<br>B: 2.22, 100% | $^1$H NMR (400 MHz, DMSO-$d_6$) δ ppm 2.32 (s, 3 H), 2.66-2.68 (m, 2 H), 2.95-3.17 (m, 4 H), 3.77-3.84 (m, 2 H), 5.22 (t, J = 4.4 Hz, 1 H), 5.40 (d, J = 2.8 Hz, 2 H), 5.44 (d, J = 4.0 Hz, 1 H), 6.93 (d, J = 3.2 Hz, 1 H), 7.60 (d, J = 8.0 Hz, 1 H), 7.71-7.77 (m, 2 H), 7.87 (d, J = 8.0 Hz, 1 H), 8.52 (d, J = 3.2 Hz, 1 H), 8.66 (s, 1 H), 9.13 (s, 1 H). |
| 26 | 430.1 | A: 1.40, 97.5%<br>B: 2.14, 100% | $^1$H NMR (400 MHz, DMSO-$d_6$) δ ppm 2.32 (s, 3 H), 2.85 (dd, J = 6.4, 4.2 Hz, 4 H), 3.55 (s, 2 H), 3.82 (s, 2 H), 5.42 (s, 2 H), 7.62-7.56 (m, 2 H), 7.70-7.65 (m, 1 H), 7.78-7.71 (m, 1 H), 8.09 (dd, J = 13.2, 2.0 Hz, 1 H), 8.33 (s, 1 H), 10.38 (s, 1 H), $^{19}$F NMR (400 MHz, DMSO-$d_6$) δ ppm 107.41. |
| 27 | 444.1 | A: 1.42, 99.7%<br>B: 2.04, 99.7% | $^1$H NMR (400 MHz, DMSO-$d_6$) δ ppm 2.30 (s, 3 H), 2.69-2.78 (m, 2 H), 2.87 (s, 4 H), 2.96-3.04 (m, 2 H), 3.64 (s, 2 H), 5.38 (s, 2 H), 7.47 (d, J = 8.0 Hz, 1 H), 7.61 (d, J = 7.6 Hz, 2 H), 7.69-7.81 (m, 1 H), 8.11 (dd, J = 13.4, 1.71 Hz, 1 H), 8.36 (s, 1 H), 10.36 (s, 1 H). $^{19}$F NMR (400 MHz, DMSO-$d_6$) δ ppm −107.42. |
| 28-I | 460.2 | A: 1.26, 97.6%<br>B: 1.79, 96.5%<br>XXII: 8.46, 100% ee | $^1$H NMR (400 MHz, DMSO-$d_6$) δ ppm 2.30 (s, 3 H), 2.73-2.62 (m, 2 H), 2.95-2.81 (m, 4 H), 3.75-3.63 (m, 2 H), 5.23-5.16 (m, 1 H), 5.42 (br. s., 3 H), 7.61 (dd, J = 8.8, 2.0 Hz, 1 H), 7.71-7.66 (m, 1 H), 7.80-7.71 (m, 2 H), 8.10 (dd, J = 13.3, 1.8 Hz, 1 H), 8.36 (s, 1 H), 10.37 (s, 1 H). $^{19}$F NMR (400 MHz, DMSO-$d_6$) δ ppm −107.40. |
| 28-II | 460 | A: 1.26, 97.3%<br>B: 1.71, 95.7%<br>XXII: 6.15<br>96.6% ee | $^1$H NMR (400 MHz, DMSO-$d_6$) δ ppm 2.30 (s, 3 H), 2.73-2.62 (m, 2 H), 2.95-2.81 (m, 4 H), 3.75-3.63 (m, 2 H), 5.23-5.16 (m, 1 H), 5.42 (br. s., 3 H), 7.61 (dd, J = 8.8, 2.0 Hz, 1 H), 7.71-7.66 (m, 1 H), 7.80-7.71 (m, 2 H), 8.10 (dd, J = 13.3, 1.8 Hz, 1 H), 8.36 (s, 1 H), 10.37 (s, 1 H). $^{19}$F NMR (400 MHz, DMSO-$d_6$) δ ppm −107.40 |
| 29-I | 460.2 | A: 1.24, 98.4%<br>B: 1.71, 97.4%<br>XXII: 5.63, 100% ee | $^1$H NMR (400 MHz, DMSO-$d_6$) δ ppm 2.37 (s, 3 H), 2.92-2.71 (m, 4 H), 3.60-3.49 (m, 1 H), 3.85-3.67 (m, 2 H), 4.01-3.87 (m, 2 H), 4.87-4.81 (m, 1 H), 5.46-5.37 (m, 2 H), 7.79-7.56 (m, 4 H), 8.13-8.05 (m, 1 H), 8.33-8.27 (m, 1 H), 10.38-10.32 (m, 1 H). $^{19}$F NMR (400 MHz, DMSO-$d_6$) δ ppm 107.42. |
| 29-II | 460.2 | A: 1.24, 98.5%<br>B: 1.71, 95.7%<br>XXII: 8.45<br>100% ee | $^1$H NMR (400 MHz, DMSO-$d_6$) δ ppm 2.37 (s, 3 H), 2.71-2.92 (m, 4 H), 3.49-3.60 (m, 1 H), 3.67-3.85 (m, 2 H), 3.87-4.01 (m, 2 H), 4.81-4.87 (m, 1 H), 5.37-5.46 (m, 2 H), 7.56-7.79 (m, 4 H), 8.05-8.13 (m, 1 H), 8.27-8.33 (m, 1 H), 10.3-10.4 (m, 1 H). $^{19}$F NMR (400 MHz, DMSO-$d_6$) δ ppm 107.42. |
| 30 | 428.2 | A: 1.44, 100%<br>B: 2.43, 100% | $^1$H NMR (400 MHz, DMSO-$d_6$) δ ppm 2.30 (s, 3 H), 2.70-2.76 (m, 2 H), 2.82 (d, J = 6.02 Hz, 2 H), 3.57 (s, 2 H), 3.77 (s, 2 H), 5.42 (s, 2 H), 6.76-6.84 (m, 2 H), 6.93-6.98 (m, 2 H), 7.00-7.06 (m, 1 H), 7.55-7.62 (m, 2 H), 7.68 (d, J = 8.03 Hz, 1 H), 9.09 (s, 1 H). $^{19}$F NMR (400 MHz, DMSO-$d_6$) δ ppm −107.85. |
| 31 | 427.2 | A: 1.064, 100%<br>B: 2.068, 100% | $^1$H NMR (400 MHz, DMSO-$d_6$) δ ppm 2.32 (s, 3 H), 2.45 (s, 3 H), 2.86 (dd, J = 8.7, 3.8 Hz, 4 H), 3.56 (s, 2 H), 3.82 (s, 2 H), 5.41 (s, 2 H), 7.59 (d, J = 8.1 Hz, 1 H), 7.68 (d, J = 7.6 Hz, 1 H), 8.33 (d, J = 5.1 Hz, 2 H), 8.58 (s, 1 H), 10.32 (s, 1H). |

TABLE 2-continued

| Ex. No. | LCMS (M + H)+ | HPLC/LCMS Method: RT (min.), Purity | NMR |
|---|---|---|---|
| 32-I | 458.2 | A: 1.43, 97.9% B: 2.01, 99% IX: 9.83, 98.90% ee | $^1$H NMR (400 MHz, DMSO-d$_6$) δ ppm 2.32 (s, 3 H), 2.62-2.69 (m, 2 H), 2.80 (br. s., 4 H), 3.59-3.74 (m, 2H), 5.14-5.21 (m, 1 H), 5.30-5.44 (m, 3 H), 6.74-6.83 (m, 2 H), 6.90-7.00 (m, 2 H), 7.07 (d, J = 8.5 Hz, 1 H), 7.59 (dd, J = 8.8, 7.8 Hz, 1 H), 7.66-7.79 (m, 2 H), 9.08 (s, 1 H). $^{19}$F NMR (400 MHz, DMSO-d$_6$) δ ppm 107.84. |
| 32-II | 458.2 | A: 1.33, 97.4% B: 2.02, 97.7% IX: 11.95, 100% ee | $^1$H NMR (400 MHz, DMSO-d$_6$) δ ppm 2.32 (s, 3 H), 2.62-2.69 (m, 2 H), 2.80 (br. s., 4 H), 3.59-3.74 (m, 2 H), 5.14-5.21 (m, 1 H), 5.30-5.44 (m, 3 H), 6.74-6.83 (m, 2 H), 6.90-7.00 (m, 2 H), 7.07 (d, J = 8.5 Hz, 1 H), 7.59 (dd, J = 8.8, 7.8 Hz, 1 H), 7.66-7.79 (m, 2 H), 9.08 (s, 1 H). $^{19}$F NMR (400 MHz, DMSO-d$_6$) δ ppm 107.84. |
| 33-I | 458.1 | A: 1.41, 97.5% B: 1.94, 97.1% XXIII: 8.41 100% ee | $^1$H NMR (400 MHz, DMSO-d$_6$) δ ppm 2.33 (s, 3 H), 2.67 (dt, J = 3.8, 1.6 Hz, 2 H), 3.55 (d, J = 15.1 Hz, 2 H), 3.81 (d, J = 15.1 Hz, 1 H), 3.87-3.91 (m, 4 H), 4.79 (br s, 1 H), 5.41 (s, 2 H), 6.76 (d, J = 2.0 Hz, 1 H), 6.78-6.82 (m, 1 H), 6.95 (d, J = 2.0 Hz, 2 H), 6.98-7.02 (m, 1 H), 7.54-7.60 (m, 1 H), 7.64-7.73 (m, 2 H), 9.07 (s, 1 H). $^{19}$F NMR (400 MHz, DMSO-d$_6$) δ ppm 107.85. |
| 33-II | 458.1 | A: 1.39, 95.4% B: 1.95, 93.3% XXIII: 9.73 92.12% ee | $^1$H NMR (400 MHz, DMSO-d$_6$) δ ppm 2.33 (s, 3 H), 2.67 (dt, J = 3.8, 1.6 Hz, 2 H), 3.55 (d, J = 15.1 Hz, 2 H), 3.81 (d, J = 15.1 Hz, 1 H), 3.87-3.91 (m, 4 H), 4.79 (br. s., 1 H), 5.41 (s, 2 H), 6.76 (d, J = 2.0 Hz, 1 H), 6.78-6.82 (m, 1 H), 6.95 (d, J = 2.0 Hz, 2 H), 6.98-7.02 (m, 1 H), 7.54-7.60 (m, 1 H), 7.64-7.73 (m, 2 H), 9.07 (s, 1 H). $^{19}$F NMR (400 MHz, DMSO-d$_6$) δ ppm 107.86. |
| 34 | 411.2 | A: 1.27, 98.2% B: 1.95, 97.6% | $^1$H NMR (400 MHz, DMSO-d$_6$) δ ppm 2.33 (s, 3 H), 2.69-2.74 (m, 2 H), 2.79-2.86 (m, 2 H), 3.54 (s, 2 H), 3.80 (s, 2 H), 5.41 (s, 2 H), 6.71 (s, 1 H), 6.95 (d, J = 8.3 Hz, 1 H), 7.29-7.41 (m, 2 H), 7.59 (d, J = 8.31 Hz, 1 H), 7.68-7.71 (m, 1 H), 7.82 (d, J = 7.8 Hz, 1 H), 8.46 (s, 1 H), 9.50 (s, 1 H). |
| 35-I | 468.2 | A: 0.912, 99.38% B: 1.158, 99.35% XXV: 24.94 100% ee | $^1$H NMR (400 MHz, DMSO-d$_6$) δ ppm 2.32 (s, 3 H), 2.54-2.57 (m, 1 H), 2.78-2.66 (m, 2 H), 2.98-3.03 (m, 3 H), 3.83-3.96 (m, 2 H), 5.19-5.27 (m, 1 H), 5.39-5.41 (m, 2 H), 5.44-5.46 (m, 1 H), 7.67-7.71 (m, 1 H), 7.74-7.80 (m, 1 H), 7.95-8.02 (m, 1 H), 8.75 (s, 2 H), 8.89-8.95 (m, 1 H). |
| 35-II | 468.2 | A: 0.914, 98.293% B: 1.159, 100% XXV: 18.93 100% ee | $^1$H NMR (400 MHz, DMSO-d$_6$) δ ppm 2.33 (s, 3 H), 2.54-2.60 (m, 1 H), 2.64-2.82 (m, 2 H), 2.98-3.06 (m, 3 H), 3.84-3.98 (m, 2 H), 5.21-5.29 (m, 1 H), 5.39-5.43 (m, 2 H), 5.45-5.51 (m, 1 H), 7.68-7.80 (m, 2 H), 7.95-8.02 (m, 1 H), 8.76 (s, 2 H), 8.87-9.01 (m, 1 H). |
| 36-I | 442.1 | A: 0.679, 98.45% B: 1.60, 98.65% X: 23.056 100% ee | $^1$H NMR (400 MHz, DMSO-d$_6$) δ ppm 2.31 (s, 3 H), 2.60-2.81 (m, 2 H), 2.93-3.07 (m, 4 H), 3.73-3.88 (m, 2 H), 5.17-5.26 (m, 1 H), 5.36-5.41 (m, 2 H), 5.43-5.48 (m, 1 H), 6.84-6.91 (m, 1 H), 7.29-7.35 (m, 1 H), 7.63-7.80 (m, 2 H), 8.44-8.49 (m, 1 H), 8.51-8.57 (m, 1 H), 8.62 (s, 1 H), 8.93-9.01 (m, 1 H). |
| 37 | 412.1 | A: 1.107, 96.27% B: 2.00, 98.29% | $^1$H NMR (400 MHz, DMSO-d$_6$) δ ppm 2.32 (s, 3 H), 2.64-2.76 (m, 2 H), 2.77-2.85 (m, 2 H), 3.51-3.58 (m, 2 H), 3.73-3.80 (m, 2 H), 5.38-5.44 (m, 2 H), 6.92-7.03 (m, 2 H), 7.44-7.50 (m, 2 H), 7.52-7.54 (m, 1 H), 7.56-7.60 (m, 1 H), 7.63-7.69 (m, 1 H), 8.33-8.36 (m, 1 H), 8.39-8.44 (m, 1 H), 9.45-9.51 (m, 1 H). |
| 38 | 426.1 | A: 1.08, 93.981% B: 1.91, 93.8% | $^1$H NMR (400 MHz, DMSO-d$_6$) δ ppm 2.34 (s, 3 H), 2.65-2.76 (m, 2 H), 2.82-2.87 (m, 2 H), 3.54-3.59 (m, 2 H), 3.75-3.79 (m, 2 H), 5.39-5.45 (m, 2 H), 6.13-6.16 (m, 1 H), 6.44-6.49 (m, 1 H), 6.96-7.01 (m, 1 H), 7.52-7.54 (m, 1 H), 7.55-7.63 (m, 2 H), 7.65-7.72 (m, 1 H), 7.85-7.93 (m, 1 H), 8.67-8.58 (m, 1 H), 9.46-9.55 (m, 1 H). |
| 39 | 428.1 | A: 1.6, 99.5% B: 1.469, 100% | $^1$H NMR (400 MHz, DMSO-d$_6$) δ ppm 2.32 (s, 3 H), 2.66-2.74 (m, 2 H), 2.77-2.84 (m, 2 H), 3.56 (s, 2 H), 3.76 (s, 2 H), 5.41 (s, 2 H), 6.72-6.82 (m, 1 H), 6.95 (s, 4 H), 7.39-7.50 (m, 1 H), 7.56-7.62 (m, 1 H), 7.64-7.71 (m, 1 H), 8.55-8.63 (m, 1 H). $^{19}$F NMR (400 MHz, DMSO-d$_6$) δ ppm 107.831. |

TABLE 2-continued

| Ex. No. | LCMS (M + H)+ | HPLC/LCMS Method: RT (min.), Purity | NMR |
|---|---|---|---|
| 40 | 426.1 | A: 1.23, 93.98%<br>B: 2.11, 100% | $^1$H NMR (400 MHz, DMSO-$d_6$) δ ppm 2.34 (s, 3 H), 2.89-2.96 (m, 2 H), 3.01-3.12 (m, 2 H), 3.66-3.75 (m, 2 H), 3.85-3.91 (m, 2 H), 5.37-5.45 (m, 2 H), 7.57-7.64 (m, 2 H), 7.66-7.74 (m, 1 H), 7.86-7.91 (m, 1 H), 8.65-8.73 (m, 1 H), 8.81-8.90 (m, 1 H), 9.24-9.31 (m, 1 H). |
| 41-I | 443.2 | A: 0.950, 95.0%<br>B: 1.35, 94.98%<br>XXV: 16.00<br>100% ee | $^1$H NMR (400 MHz, DMSO-$d_6$) δ ppm 2.30 (s, 3 H), 2.61-2.77 (m, 3 H), 2.95-3.06 (m, 3 H), 3.74-3.89 (m, 2 H), 5.13-5.29 (m, 1 H), 5.34-5.48 (m, 3 H), 7.54-7.62 (m, 1 H), 7.64-7.81 (m, 2 H), 8.63-8.71 (m, 3 H), 8.91-8.99 (m, 1 H). |
| 41-II | 443.1 | A: 0.789, 100%<br>B: 1.387, 94.74%<br>XXVII: 19.93<br>97.89% ee | $^1$H NMR (400 MHz, DMSO-$d_6$) δ ppm 2.30 (s, 3 H), 2.61-2.77 (m, 3 H), 2.95-3.06 (m, 3 H), 3.74-3.89 (m, 2 H), 5.13-5.29 (m, 1 H), 5.34-5.48 (m, 3 H), 7.54-7.62 (m, 1 H), 7.64-7.81 (m, 2 H), 8.63-8.71 (m, 3 H), 8.91-8.99 (m, 1 H). |
| 42-I | 467.2 | A: 1.08, 100%<br>B: 1.85, 98.53%<br>XVII: 16.20<br>100% ee | $^1$H NMR (400 MHz, DMSO-d6) δ ppm 2.35 (s, 3 H), 2.62-2.77 (m, 2 H), 2.90-3.13 (m, 4 H), 3.82-3.90 (m, 2 H), 5.18-5.28 (m, 1 H), 5.38-5.47 (m, 3 H), 6.98-7.04 (m, 1 H), 7.67-7.79 (m, 2 H), 8.67-8.74 (m, 1 H), 8.80-8.86 (m, 2 H), 10.12-10.21 (m, 1 H). |
| 42-II | 467.2 | A: 1.086, 100%<br>B: 1.85, 100%<br>XVII: 20.49<br>95.4% ee | $^1$H NMR (400 MHz, DMSO-$d_6$) δ ppm 2.35 (s, 3 H), 2.62-2.77 (m, 2 H), 2.90-3.13 (m, 4 H), 3.82-3.90 (m, 2 H), 5.18-5.28 (m, 1 H), 5.38-5.47 (m, 3 H), 6.98-7.04 (m, 1 H), 7.67-7.79 (m, 2 H), 8.67-8.74 (m, 1 H), 8.80-8.86 (m, 2 H), 10.12-10.21 (m, 1 H). |
| 43-I | 468.1 | A: 1.087, 92.131%<br>B: 1.56, 92.237%<br>XXVI: 31.94<br>100% ee | $^1$H NMR (400 MHz, DMSO-$d_6$) δ ppm 2.36 (s, 3 H), 2.62-2.80 (m, 2 H), 2.95-3.11 (m, 4 H), 3.78-3.96 (m, 2 H), 5.18-5.27 (m, 1 H), 5.36-5.49 (m, 3 H), 7.66-7.80 (m, 2 H), 8.71-8.78 (m, 1 H), 8.83-8.90 (m, 1 H), 8.97-9.06 (m, 1 H), 10.20-10.31 (m, 1 H). |
| 43-II | 468.1 | A: 1.086, 90.6%<br>B: 1.568, 95.1%<br>XXVI: 47.68<br>91.96% ee | $^1$H NMR (400 MHz, DMSO-$d_6$) δ ppm 2.36 (s, 3 H), 2.62-2.80 (m, 2 H), 2.95-3.11 (m, 4 H), 3.78-3.96 (m, 2 H), 5.18-5.27 (m, 1 H), 5.36-5.49 (m, 3 H), 7.66-7.80 (m, 2 H), 8.71-8.78 (m, 1 H), 8.83-8.90 (m, 1 H), 8.97-9.06 (m, 1 H), 10.20-10.31 (m, 1 H). |
| 44-I | E:1.98<br>467.2 | N: 10.08, 96.40%<br>O: 11.38, 96.27%<br>V: 5.33<br>100% ee | $^1$H NMR (400 MHz, DMSO-$d_6$) δ ppm 2.33 (s, 3 H), 2.65-2.80 (m, 2 H), 3.00 (s, 4 H), 3.81-3.93 (m, 2 H), 5.20-5.27 (m, 1 H), 5.40-5.45 (m, 3 H), 6.90 (d, J = 4.0 Hz, 1 H), 7.68-7.72 (m, 1 H), 7.74-7.79 (m, 1 H), 8.34 (d, J = 3.5 Hz, 1 H), 8.66 (d, J = 2.0 Hz, 1 H), 8.70 (s, 1 H), 8.80 (d, J = 2.0 Hz, 1 H). |
| 45-I | E:1.91<br>467.2 | N: 10.18, 97.33%<br>O: 11.19, 97.35%<br>IV: 4.49<br>100% ee | $^1$H NMR (400 MHz, DMSO-$d_6$) δ ppm 2.32 (s, 3 H), 2.80-3.02 (m, 4 H), 3.65-3.80 (m, 2 H), 3.89-4.05 (m, 3 H), 4.90 (t, J = 5.2 Hz, 1 H), 5.42 (s, 2 H), 6.88 (d, J = 4.0 Hz, 1 H), 7.59-7.76 (m, 2 H), 8.32 (d, J = 3.5 Hz, 1 H), 8.59-8.67 (m, 2 H), 8.78 (d, J = 2.0 Hz, 1 H). |
| 46 | 423.1 | A: 1.08, 98.24%<br>B: 1.67, 94.87% | $^1$H NMR (400 MHz, DMSO-$d_6$) δ ppm 2.86-2.94 (m, 2 H), 2.98-3.06 (m, 2 H), 3.70 (s, 2 H), 3.92 (s, 2 H), 5.42 (s, 2 H), 6.89 (d, J = 3.7 Hz, 1 H), 7.62 (d, J = 7.6 Hz, 1 H), 7.71 (s, 1 H), 7.85 (d, J = 7.8 Hz, 1 H), 8.33 (d, J = 3.7 Hz, 1 H), 8.62-8.68 (m, 2 H), 8.78 (d, J = 1.9 Hz, 1 H). |
| 47 | 444.1 | A: 1.263, 99.02%<br>B: 2.156, 99.42% | $^1$H NMR (400 MHz, DMSO-$d_6$) δ ppm 2.32 (s, 3 H), 2.75-2.85 (m, 4 H), 3.53 (s, 2 H), 3.55 (s, 3 H), 3.81 (s, 2 H), 5.41 (s, 2 H), 7.44 (dd, J = 8.4, 2.0 Hz, 1 H), 7.55-7.69 (m, 3 H), 7.80 (t, J = 8.0 Hz, 1 H), 8.25 (s, 1 H). $^{19}$F NMR (400 MHz, DMSO-$d_6$) δ ppm 108.60. |
| 48 | 429.2 | A: 1.20, 93.74%<br>B: 2.07, 94.46% | $^1$H NMR (400 MHz, DMSO-$d_6$) δ ppm 2.65-2.70 (m, 2 H), 2.80-2.85 (m, 2 H), 3.33 (s, 3 H), 3.53 (s, 2 H), 3.68 (s, 2 H), 6.77 (d, J = 2.5 Hz, 1 H), 6.93-6.96 (m, 2 H), 7.00-7.04 (m, 1 H), 7.12 (dd, J = 8.5, 1.5 Hz, 1H), 7.24-7.30 (m, 2 H), 7.55-7.61 (m, 1 H), 9.08 (s, 1 H). $^{19}$F NMR (400 MHz, DMSO-$d_6$) δ ppm −107.85. |
| 49 | 458.2 | A: 1.08, 97.83%<br>B: 1.76, 98.82% | $^1$H NMR (400 MHz, DMSO-$d_6$) δ ppm 2.32 (s, 3 H), 2.81 (s, 4 H), 3.30 (s, 3 H), 3.51 (s, 2 H), 3.80 (s, 2 H), 5.42 (s, 2 H), 7.21 (d, J = 8.56 Hz, 1 H), 7.32-7.38 (m, 1 H), 7.59 (s, 1 H), 7.66 (s, 1 H), 7.76 (d, J = 2.20 Hz, 1 H), 8.19 (s, 1 H), 9.56 (s, 1 H). |

TABLE 2-continued

| Ex. No. | LCMS (M + H)+ | HPLC/LCMS Method: RT (min.), Purity | NMR |
|---|---|---|---|
| 50 | 467.2 | A: 1.179, 97.15%<br>B: 1.77, 98.86%<br>XXVIII: 16.81<br>100% ee | $^1$H NMR (400 MHz, DMSO-$d_6$) δ ppm 2.32 (s, 3 H), 2.78-2.70 (m, 2 H), 3.09-2.99 (m, 4 H), 3.92-3.81 (m, 2 H), 5.18-5.23 (m, 1 H), 5.46 (s, 2 H), 5.47 (s, 1 H), 7.70 (d, J = 8.00 Hz, 1 H), 7.76 (d, J = 8.00 Hz, 1 H), 7.97 (d, J = 1.20 Hz, 1 H), 8.54 (s, 1 H), 8.61 (s, 1 H), 8.70 (s, 1 H), 8.79 (d, J = 8.80 Hz, 1 H). |
| 51-I | 515.1 | A: 1.22 97.12%<br>B: 1.69 97.77% | $^1$H NMR (400 MHz, DMSO-$d_6$) δ ppm 1.41 (t, J = 7.09 Hz, 3 H), 2.33 (s, 3 H), 2.64-2.83 (m, 2 H), 2.96-3.10 (m, 4 H), 3.79-3.94 (m, 2 H), 4.45 (q, J = 7.09 Hz, 2 H), 5.25 (d, J = 3.67 Hz, 1 H), 5.41 (d, J = 3.18 Hz, 2 H), 5.46 (d, J = 3.67 Hz, 1 H), 7.66-7.72 (m, 1 H), 7.74-7.83 (m, 1 H), 8.74 (s, 1 H), 8.81 (d, J = 0.73 Hz, 1 H), 9.18 (d, J = 1.96 Hz, 1 H), 9.47 (dd, J = 1.83, 0.86 Hz, 1 H). |
| 52-I | 500.2 | A: 1.09 100%<br>B: 1.86 97.03% | $^1$H NMR (400 MHz, DMSO-$d_6$) δ ppm 2.35 (br. s., 3 H), 2.64-2.83 (m, 2 H), 3.01 (s, 4 H), 3.77-3.89 (m, 2 H), 3.90-4.01 (m, 3 H), 5.19-5.28 (m, 1 H), 5.36-5.43 (m, 2 H), 5.46 (d, J = 3.91 Hz, 1 H), 7.00 (d, J = 3.67 Hz, 1 H), 7.65-7.74 (m, 1 H), 7.75-7.80 (m, 1 H), 8.67 (s, 1 H), 8.74 (d, J = 3.67 Hz, 1 H), 9.03 (d, J = 1.96 Hz, 1 H), 9.48 (d, J = 1.22 Hz, 1 H). |
| 53-I | 443.0 | A: 0.82 93.80%<br>B: 1.44 93.83% | $^1$H NMR (400 MHz, DMSO-$d_6$) δ ppm 2.27-2.37 (m, 3 H), 2.62-2.82 (m, 2 H), 2.97-3.12 (m, 4 H), 3.87 (d, J = 9.05 Hz, 2 H), 5.24 (d, J = 3.42 Hz, 1 H), 5.41 (d, J = 3.42 Hz, 2 H), 5.48 (d, J = 4.16 Hz, 1 H), 7.48 (dd, J = 8.19, 4.77 Hz, 1 H), 7.67-7.83 (m, 2 H), 8.55 (dd, J = 4.65, 1.71 Hz, 1 H), 8.71 (s, 1 H), 8.82-8.90 (m, 1 H), 9.33 (s, 1 H). |
| 54-I | 418.0 | A: 1.29 94.76%<br>B: 1.37 99.40% | $^1$H NMR (400 MHz, DMSO-$d_6$) δ ppm 2.31 (s, 3 H), 2.58-2.73 (m, 2 H), 2.82 (d, J = 4.89 Hz, 2 H), 2.91 (br. s., 2 H), 3.56-3.76 (m, 2 H), 5.20 (d, J = 8.31 Hz, 1 H), 5.34-5.46 (m, 3 H), 7.29 (dd, J = 8.44, 4.52 Hz, 1 H), 7.66-7.71 (m, 1 H), 7.73-7.78 (m, 1 H), 8.13 (dd, J = 4.77, 1.35 Hz, 1 H), 8.21 (dd, J = 5.14, 3.42 Hz, 1 H), 8.26 (s, 1 H), 8.89 (d, J = 2.45 Hz, 1 H), 9.66 (s, 1 H). |
| 55-I | 443.3 | A: 0.59 94.28%<br>B: 1.26 95.98% | $^1$H NMR (400 MHz, DMSO-$d_6$) δ ppm 2.22-2.42 (m, 3 H), 2.78 (s, 2 H), 3.01 (br. s., 3 H), 3.17 (d, J = 5.14 Hz, 1 H), 3.71-3.95 (m, 2 H), 5.18-5.29 (m, 1 H), 5.38-5.59 (m, 3 H), 7.42 (dd, J = 7.95, 4.77 Hz, 1 H), 7.63-7.83 (m, 2 H), 8.21 (d, J = 8.07 Hz, 1 H), 8.50 (d, J = 4.65 Hz, 1 H), 8.73 (s, 1 H), 9.05 (s, 1 H). |
| 56-I | 417.2 | F: 15.25 97.40%<br>G: 13.94 97.85% | $^1$H NMR (400 MHz, DMSO-$d_6$) δ ppm 2.30 (s, 3 H), 2.64-2.78 (m, 2 H), 2.98 (s, 4 H), 3.76-3.91 (m, 2 H), 5.18-5.25 (m, 1 H), 5.39 (d, J = 3.01 Hz, 2 H), 5.40-5.45 (m, 1 H), 7.65-7.71 (m, 1 H), 7.73-7.77 (m, 1 H), 8.38 (s, 1 H), 8.66 (s, 1 H), 9.40 (s, 1 H). |
| 57-I | 460.2 | A: 1.26 100%<br>B: 1.81 100%<br>IV: 11.04<br>100% ee | $^1$H NMR (400 MHz, DMSO-$d_6$) δ ppm 2.27 (s, 3 H), 2.72-2.82 (m, 1 H), 2.92-3.00 (m, 1 H), 3.14 (t, J = 6.8 Hz, 1 H), 3.46-3.73 (m, 4 H), 3.88-4.02 (m, 2 H), 4.74 (t, J = 5.2 Hz, 1 H), 5.38 (s, 2 H), 7.55-7.65 (m, 3 H), 7.72 (t, J = 10.8 Hz, 1 H), 8.07 (dd, J = 10.8 Hz, J = 2.4 Hz, 1 H), 8.25 (s, 1 H), 10.36 (s, 1 H). |
| 57-II | 458.2<br>(M − H) | C: 10.27 99.75%<br>F: 11.90 98.35% | $^1$H NMR (400 MHz, DMSO-$d_6$) δ ppm 2.27 (s, 3 H), 2.72-2.82 (m, 1 H), 2.92-3.00 (m, 1 H), 3.14 (t, J = 6.8 Hz, 1 H), 3.46-3.73 (m, 4 H), 3.88-4.02 (m, 2 H), 4.74 (t, J = 5.2 Hz, 1 H), 5.38 (s, 2 H), 7.55-7.65 (m, 3 H), 7.72 (t, J = 10.8 Hz, 1 H), 8.07 (dd, J = 10.8 Hz, J = 2.4 Hz, 1 H), 8.25 (s, 1 H), 10.36 (s, 1 H). |
| 58-I | 406.2 | A: 0.26 98.80%<br>B: 1.44 98.66%<br>I: 3.34<br>100% ee | $^1$H NMR (400 MHz, DMSO-$d_6$) δ ppm 2.18 (d, J = 0.73 Hz, 3 H), 2.31 (s, 3 H), 2.63-2.78 (m, 2 H), 2.96 (d, J = 4.40 Hz, 4 H), 3.73-3.88 (m, 2 H), 5.21 (dt, J = 7.95, 3.85 Hz, 1 H), 5.40 (d, J = 3.18 Hz, 2 H), 5.44 (d, J = 3.91 Hz, 1 H), 7.62 (s, 1 H), 7.66-7.72 (m, 1 H), 7.73-7.79 (m, 1 H), 8.41 (s, 1 H), 8.56 (s, 1 H). |
| 59-I | 406.1 | A: 0.23 100%<br>B: 1.37 99.59%<br>I: 3.35<br>100% ee | $^1$H NMR (400 MHz, DMSO-$d_6$) δ ppm 2.31 (s, 3 H), 2.62-2.80 (m, 5 H), 2.90-3.00 (m, 4 H), 3.76-3.90 (m, 2 H), 5.17-5.26 (m, 1 H), 5.40 (d, J = 2.93 Hz, 2 H), 5.44 (d, J = 3.91 Hz, 1 H), 6.90 (d, J = 1.71 Hz, 1 H), 7.69 (s, 1 H), 7.73-7.77 (m, 1 H), 7.79 (d, J = 1.47 Hz, 1 H), 8.61 (s, 1 H). |
| 60-I | 467.1 | A: 1.25 100%<br>B: 1.96 100% | $^1$H NMR (400 MHz, DMSO-$d_6$) δ ppm 2.33 (s, 3 H), 2.66-2.82 (m, 2 H), 3.03 (d, J = 4.65 Hz, 2 H), 3.07 (d, J = 4.89 Hz, 2 H), 3.83-3.96 (m, 2 H), 5.24 (dt, J = 7.89, 4.25 Hz, 1 H), 5.41 (d, J = 3.18 Hz, 2 H), 5.46 (d, |

TABLE 2-continued

| Ex. No. | LCMS (M + H)+ | HPLC/LCMS Method: RT (min.), Purity | NMR |
|---|---|---|---|
| | | | J = 3.91 Hz, 1 H), 7.59 (t, J = 7.58 Hz, 1 H), 7.67-7.73 (m, 1 H), 7.74-7.81 (m, 2 H), 8.03 (d, J = 8.31 Hz, 1 H), 8.74-8.80 (m, 2 H). |
| 61-I | 443.1 | A: 0.987, 99.69%<br>B: 1.531, 98.34% | $^1$H NMR (400 MHz, DMSO-$d_6$) δ ppm 2.25-2.35 (m, 3 H), 2.67 (d, J = 1.71 Hz, 2 H), 2.80-3.01 (m, 4 H), 3.69 (d, J = 9.78 Hz, 2 H), 5.20 (br. s., 1 H), 5.32-5.52 (m, 3 H), 7.62-7.79 (m, 2 H), 8.34 (s, 1 H), 8.53 (d, J = 1.96 Hz, 1 H), 8.64-8.80 (m, 1 H), 9.09 (d, J = 2.69 Hz, 1 H), 10.12 (s, 1 H). |
| 62-I | 488.2 | A: 1.04 98.46%<br>B: 1.52 100%<br>I: 3.42<br>100% ee | $^1$H NMR (400 MHz, DMSO-$d_6$) δ ppm 2.30 (s, 3 H), 2.58-2.73 (m, 3 H), 2.79 (br. s., 2 H), 2.89 (br. s., 2 H), 3.38-3.44 (m, 2 H), 3.64 (d, J = 11.25 Hz, 2 H), 5.19 (br. s., 1 H), 5.40 (s, 3 H), 7.21 (d, J = 8.80 Hz, 1 H), 7.37 (dd, J = 8.80, 2.20 Hz, 1 H), 7.66-7.71 (m, 1 H), 7.72-7.75 (m, 1 H), 7.76 (d, J = 1.96 Hz, 1 H), 8.22 (s, 1 H), 9.53 (s, 1 H). |
| 63-I | 486.2 | A: 0.85 96.37%<br>B: 1.43 98.62%<br>I: 3.36<br>100% ee | $^1$H NMR (400 MHz, DMSO-$d_6$) δ ppm 2.28-2.34 (m, 3 H), 2.61-2.80 (m, 2 H), 2.90 (br. S., 4 H), 3.75 (br. S., 2 H), 5.24 (br. S., 1 H), 5.34-5.51 (m, 3 H), 7.66-7.79 (m, 2 H), 8.24 (dd, J = 9.05, 2.69 Hz, 1 H), 8.38 (s, 1 H), 8.53 (d, J = 9.05 Hz, 1 H), 8.77 (d, J = 2.69 Hz, 1 H), 10.03 (s, 1 H), 10.22 (br. S., 1 H). |
| 64-I | 472.1 | A: 1.00 100%<br>B: 1.66 100% | $^1$H NMR (400 MHz, DMSO-$d_6$) δ ppm 2.04-2.09 (m, 1 H), 2.27-2.31 (m, 3 H), 2.52-2.62 (m, 2 H), 2.80-2.30 (m, 5 H), 3.96-4.01 (s, 3 H), 5.20-5.03 (m, 1 H), 5.39 (m, 3 H), 7.64-7.77 (m, 2 H), 8.26-8.31 (m, 1 H), 8.37-8.42 (m, 1 H), 8.46-8.48 (m, 1 H), 10.38 (br. s., 1 H). |
| 65-I | 468.3 | A: 1.25 97.80%<br>B: 1.91 97.62%<br>XX: 15.63<br>100% ee | $^1$H NMR (400 MHz, DMSO-$d_6$) δ ppm 2.31 (s, 3 H), 2.60-2.76 (m, 2 H), 2.82-2.95 (m, 4 H), 3.35 (t, J = 8.56 Hz, 2 H), 3.59-3.80 (m, 2 H), 4.25 (t, J = 8.56 Hz, 2 H), 5.13-5.26 (m, 1 H), 5.35-5.46 (m, 3 H), 7.28 (d, J = 7.34 Hz, 1 H), 7.37 (t, J = 8.07 Hz, 1 H), 7.66-7.72 (m, 1 H), 7.72-7.80 (m, 1 H), 8.37 (s, 1 H), 8.57 (d, J = 8.31 Hz, 1 H) |
| 65-II | 468.3 | A: 1.35 98.87%<br>B: 2.07 100%<br>XX: 14.50<br>95% ee | $^1$H NMR (400 MHz, DMSO-$d_6$) δ ppm 2.31 (s, 3 H), 2.60-2.76 (m, 2 H), 2.82-2.95 (m, 4 H), 3.35 (t, J = 8.56 Hz, 2 H), 3.59-3.80 (m, 2 H), 4.25 (t, J = 8.56 Hz, 2 H), 5.13-5.26 (m, 1 H), 5.35-5.46 (m, 3 H), 7.28 (d, J = 7.34 Hz, 1 H), 7.37 (t, J = 8.07 Hz, 1 H), 7.66-7.72 (m, 1 H), 7.72-7.80 (m, 1 H), 8.37 (s, 1 H), 8.57 (d, J = 8.31 Hz, 1 H) |
| 66-I | 392.1 | A: 0.28 93.80%<br>B: 1.32 93.86%<br>XX: 12.57<br>98.50% ee | $^1$H NMR (400 MHz, DMSO-$d_6$) δ ppm 2.30 (m, 4 H), 2.63-2.77 (m, 2 H), 2.95 (s, 3 H), 3.73-3.85 (m, 2 H), 5.15-5.24 (m, 1 H), 5.39 (d, J = 2.93 Hz, 3 H), 7.12 (s, 1 H), 7.63-7.78 (m, 2 H), 7.90 (s, 1 H), 8.53 (s, 1 H), 8.59 (s, 1 H). |
| 67-I | 442.1.1 | A: 1.04 100%<br>B: 1.75 98.14%<br>XX: 17.07<br>99.65% ee | $^1$H NMR (400 MHz, DMSO-$d_6$) δ ppm 2.32 (s, 3 H), 2.63-2.81 (m, 2 H), 2.92-3.08 (m, 4 H), 3.78-3.92 (m, 2 H), 5.15-5.29 (m, 1 H), 5.33-5.47 (m, 3 H), 7.33-7.48 (m, 2 H), 7.64-7.71 (m, 1 H), 7.73-7.82 (m, 2 H), 8.52-8.59 (m, 1 H), 8.65-8.70 (m, 1 H), 9.01-9.10 (m, 1 H). |
| 68-I | 467.2 | A: 1.06 97.49%<br>B: 1.71 98.30% | $^1$H NMR (400 MHz, DMSO-$d_6$) δ ppm 2.32 (s, 3 H), 2.65-2.80 (m, 3 H), 2.95-3.09 (m, 4 H), 3.82-3.90 (m, 1 H), 5.19-5.26 (m, 1 H), 5.35-5.48 (m, 3 H), 7.51-7.61 (m, 1 H), 7.70-7.80 (m, 2 H), 8.59-8.76 (m, 2 H), 9.01-9.11 (m, 1 H), 9.33 (s, 1 H). |

BIOLOGICAL ASSAYS

The pharmacological properties of the compounds of this invention may be confirmed by a number of biological assays. The exemplified biological assays, which follow, have been carried out with compounds of the invention.

Thallium Flux Assay

Solutions and reagents: Thallium flux assay was performed using FluxOR kit (F10017, Life Technologies). Loading buffer, assay buffer and stimulus buffer were prepared using kit components. HBSS (Hank's balanced salt solution, Cat #14025-092) was purchased separately from Life Technologies.

To prepare 10 ml of loading buffer: 10 µl of FluxOR dye (reconstituted in DMSO) was first added to 100 µl of powerload concentrate and this mix along with 100 µl of Probenicid (100×) was then added to 9.79 ml of HBSS. Assay buffer (10 ml) was prepared by addition of 2 ml of FluxOR chloride free buffer (5×), 100 µl of Probenicid (100×), and 0.2 ml of Ouabain (13.77 mM) to 7.7 ml of deionized water. Stimulus buffer was composed of 15 mM $Tl_2SO_4$, 0.75 mM $K_2SO_4$ in FluxOR chloride free buffer (diluted to 1× using deionized water). The final concentration of $Tl_2SO_4$ and $K_2SO_4$ in the assay plate was 3 mM and 0.15 mM, respectively.

Plating and induction of cells: The CHO T-Rex hROMK (human $K_{ir}1.1$) stable cell line was maintained in Ham's F12 media supplemented with 10% FBS, 1% Penicillin-Streptomycin, 500 µg/ml Zeocin and 10 µg/ml Blasticidin at 37° C. in a 5% $CO_2$ incubator. One day before the experiment, the cells were dissociated by incubation with Versene solution (15040-066, Life Technologies) for 10 minutes at 37° C. followed by addition of growth media. The cell suspension was centrifuged at 1200 rpm for 5 min. After discarding the supernatant, the cells were resuspended in fresh growth media and cell concentration was determined using a hemocytometer. Next, 0.5 µg/ml of Doxycycline was added to the cell suspension to induce hROMK channel expression and 50 µl (10,000 cells/well) of cell suspension was added to each well of a poly-D lysine coated 384 well black, optically clear bottom plate (6007718, Perkin Elmer). The assay plate was kept at 37° C. in a 5% $CO_2$ incubator.

Assay protocol: On the day of experiment, media was removed and loading buffer was added (30 µl/well) to the assay plate. The cells were incubated in the loading buffer for 30 minutes at 37° C. The loading buffer was then replaced by assay buffer (30 µl/well) followed by addition of test compounds or controls. The cells were incubated with compounds for 30 minutes and the plate was then mounted on FlexStation (Molecular Devices) for fluorescence read out with excitation and emission wavelengths at 488 and 525 nm, respectively. Each well was read for 90 sec at 2 sec interval and the stimulus buffer was added after 20 seconds of baseline recording. The final DMSO concentration was either 0.5 or 1% in the assay plate. Positive and negative controls were defined by addition of DMSO or 3 µM of a standard ROMK inhibitor, respectively, to the wells instead of a test compound.

Data analysis: The slope (over a period of 15 seconds) of fluorescence increase after stimulus buffer addition was exported from SoftMax Pro into a custom made software where it was converted to % inhibition. A 10-point concentration response curve was used to estimate the $IC_{50}$ value of test compounds.

The data in Table 3 is reported with two significant figures.

TABLE 3

| Ex. No. | hROMK Th+ Flux $IC_{50}$ (nM) |
|---|---|
| 1-I | 54 |
| 1-II | 460 |
| 2 | 960 |
| 3-I | 740 |
| 3-II | 1600 |
| 4 | 29 |
| 5 | 790 |
| 6 | 120 |
| 7 | 200 |
| 8-I | 28 |
| 8-II | 83 |
| 9-I | 3000 |
| 9-II | 1800 |
| 10 | 4600 |
| 11 | 1200 |
| 12-I | 38 |
| 12-II | 410 |
| 13 | 750 |
| 14 | 320 |
| 15 | 21 |
| 16-I | 380 |
| 16-II | 380 |
| 17-I | 340 |
| 17-II | 850 |

TABLE 3-continued

| Ex. No. | hROMK Th+ Flux $IC_{50}$ (nM) |
|---|---|
| 18-II | 580 |
| 19-I | 460 |
| 19-II | 1900 |
| 20 | 1500 |
| 21 | 3200 |
| 22-I | 1000 |
| 22-II | 700 |
| 23 | 1100 |
| 24 | 820 |
| 26 | 270 |
| 27 | 200 |
| 28-I | 120 |
| 28-II | 310 |
| 29-I | 3000 |
| 29-II | 2100 |
| 30 | 810 |
| 31 | 1500 |
| 32-I | 50 |
| 32-II | 83 |
| 33-I | 490 |
| 33-II | 1800 |
| 34 | 300 |
| 35-I | 800 |
| 35-II | 4900 |
| 36-I | 180 |
| 37 | 4900 |
| 38 | 1900 |
| 39 | 550 |
| 40 | 3400 |
| 41-I | 60 |
| 41-II | 1200 |
| 42-I | 70 |
| 42-II | 210 |
| 43-I | 180 |
| 43-II | 640 |
| 44-I | 2100 |
| 45-I | 4700 |
| 46 | 1500 |
| 47 | 1900 |
| 48 | 600 |
| 49 | 1800 |
| 50 | 700 |
| 51-I | 495 |
| 52-I | 1242 |
| 53-I | 135 |
| 54-I | 217 |
| 55-I | 1495 |
| 56-I | 44 |
| 57-I | 830 |
| 57-II | 679 |
| 58-I | 62 |
| 59-I | 224 |
| 60-I | 30 |
| 61-I | 568 |
| 62-I | 1030 |
| 63-I | 1241 |
| 64-I | 381 |
| 65-I | 31 |
| 65-II | 376 |
| 66-I | 362 |
| 67-I | 157 |
| 68-I | 29 |

ROMK Manual Patch Clamp Assay

Cell culture conditions: Cells were maintained in conditions similar to those for Thallium flux assay. hROMK channel expression was induced by adding 0.6 µg/ml of Doxycycline 16-24 hrs prior to the experiments. On the day of experiment, the cells were dissociated using Versene, resuspended in growth media and plated onto coverslips 15 minutes prior to use.

Electrophysiology: The coverslip plated with cells was placed in the experiment chamber perfused with bath solution composed of (in mM): 135 NaCl, 5 KCl, 2 $CaCl_2$, 1 $MgCl_2$, 10 HEPES, 5 Glucose (pH 7.4). Patch pipettes with resistance between 2-5 Megaohms, when filled with a solution containing (in mM): 135 KCl, 1 EGTA, 1 $MgCl_2$, 10 HEPES, 2 $Na_2ATP$ (pH 7.3), were used to form gigaseals. The cells were voltage clamped at −75 mV in whole-cell configuration using an Axopatch 200b or Multiclamp 700b (Molecular Devices) amplifier controlled by pClamp Software (Molecular Devices). The current was recorded by applying a voltage step to −120 mV every 10 seconds. For each compound, 4-6 concentrations were applied for 3-8 minutes in a successive manner starting with the lowest concentration. At the end of the experiment, the cells were perfused with bath solution containing 2 mM $Ba^{2+}$ to isolate the contribution of hROMK current.

Data analysis: Raw current values (5 traces each for control, different compound concentration and $Ba^{2+}$ treatment groups) were exported from Clampfit into Microsoft Excel where the current remaining after application of $Ba^{2+}$ was subtracted from raw current to obtain hROMK specific current. These hROMK current values (average of 5 traces for each group) were then imported into a custom made template to generate a concentration response curve, which was subsequently fitted with a four parameter equation to calculate the $IC_{50}$ value of the test compound.

The data in Table 4 is reported with two significant figures.

TABLE 4

| Patent Example Number | hROMK EP $IC_{50}$ (nM) |
| --- | --- |
| 4 | 31 |
| 41-I | 23 |
| 42-I | 34 |
| 53-I | 87 |
| 56-I | 12 |
| 58-I | 13 |
| 68-I | 23 | hERG Manual Patch Clamp Assay hERG electrophysiology assay: The experimental compounds were assessed for hERG activity on HEK 293 cells stably expressing hERG channels using patch clamp technique. Coverslips plated with hERG expressing cells were placed in the experimental chamber and were perfused with a solution composed of (in mM): 140 NaCl, 4 KCl, 1.8 $CaCl_2$, 1 $MgCl_2$, 10 Glucose, 10 HEPES (pH 7.4, NaOH) at room temperature. Borosilicate patch pipettes had tip resistances of 2-4 Mohms when filled with an internal solution containing: 130 KCl, 1 $MgCl_2$, 1 $CaCl_2$, 10 EGTA, 10 HEPES, 5 ATP-$K_2$ (pH 7.2, KOH). The cells were clamped at −80 mV in whole cell configuration using an Axopatch 200B (Axon instruments, Union City, Calif.) patch clamp amplifier controlled by pClamp (Axon instruments) software. Upon formation of a gigaseal, the following voltage protocol was repeatedly (0.05 Hz) applied to record tail currents: depolarization step from −80 mV to +20 mV for 2 seconds followed by a hyperpolarization step to −65 mV (3 seconds) to elicit tail currents. Compounds were applied after stabilization of tail current. First, tail currents were recorded in presence of extracellular solution alone (control) and subsequently, in extracellular solution containing increasing compound concentrations. Each compound concentration was applied for 2-5 minutes. The percentage inhibition at each concentration was calculated as reduction in peak tail current with respect to the peak tail current recorded in the presence of control solution. Data analysis was performed in a custom made template. The percent inhibitions at different concentrations were plotted to obtain a concentration response curve, which was subsequently fitted with a four parameter equation to calculate hERG $IC_{50}$ value.

A lower hERG % Inhibition value indicates less inhibition of the hERG current

TABLE 5

| Ex. No. | hERG EP $IC_{50}$ (% Inhibition at 1 μM) |
| --- | --- |
| 1-I | 78% @1 μM |
| 4 | 94% @1 μM |
| 8-I | 98% @1 μM |
| 16-I | 25% @1 μM |
| 28-I | 91% @1 μM |
| 32-I | 100% @1 μM |
| 32-II | 97% @1 μM |
| 36-I | 12% @1 μM, |
| 41-I | 11% @1 μM |
| 42-I | 41% @1 μM, |
| 43-I | 16% @1 μM, |
| 53-I | 13% @1 uM, |
|  | 34% @3 uM |
| 54-I | 32% @1 uM |
| 56-I | 35% @1 uM, |
|  | 65% @3 uM, |
|  | 82% @10 uM |
| 58-I | 9% @1 uM, |
|  | 20% @3 uM, |
|  | 42% @10 uM |
| 59-I | 13% @1 uM, |
|  | 27% @3 uM, |
|  | 51% @10 uM |
| 60-I | 92% @1 uM |
| 65-I | 56% @1 uM |
| 66-I | 6% @1 uM, |
|  | 14% @3 uM, |
|  | 30% @10 uM |
| 68-I | 22% @1 uM, |
|  | 54% @3 uM, |
|  | 86% @10 uM |

What is claimed is:

1. A compound having the structure of Formula (I)

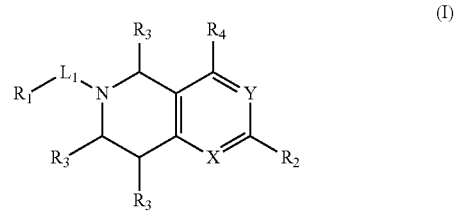

or a salt thereof, wherein:

X is $CR_4$ or N;

Y is $CR_4$ or N, provided that Y is N only if X is N;

$R_1$ is:

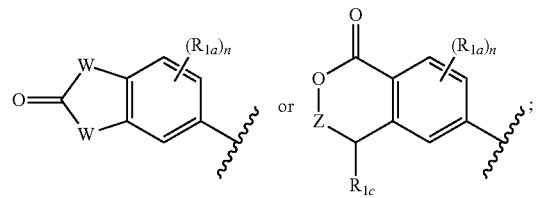

each W is independently NR$_{1b}$ or O;
Z is a bond or CHR$_{1d}$;
each R$_{1a}$ is independently H, F, Cl, —OH, C$_{1-3}$ alkyl, C$_{1-3}$ fluoroalkyl, C$_{3-6}$ cycloalkyl, C$_{1-3}$ alkoxy, or C$_{1-3}$ fluoroalkoxy;
each R$_{1b}$ is independently H, C$_{1-3}$ alkyl, C$_{1-3}$ fluoroalkyl, aryl, or heteroaryl;
R$_{1c}$ is H, C$_{1-4}$ alkyl, or C$_{3-6}$ cycloalkyl;
R$_{1d}$ is H, C$_{1-3}$ alkyl, C$_{3-6}$ cycloalkyl, or C$_{1-3}$ alkoxy;
n is zero, 1, 2, or 3;
L$_1$ is a bond, —CHR$_b$—, or —CHR$_a$CHR$_b$—;
R$_a$ is H, halo, —OH, C$_{1-4}$ alkyl, C$_{1-3}$ fluoroalkyl, C$_{1-3}$ hydroxyalkyl, C$_{3-6}$ cycloalkyl, C$_{1-3}$ alkoxy, or C$_{1-3}$ fluoroalkoxy;
R$_b$ is H, C$_{1-4}$ alkyl, C$_{1-3}$ fluoroalkyl, C$_{1-3}$ hydroxyalkyl, C$_{3-6}$ cycloalkyl, C$_{1-3}$ alkoxy, or C$_{1-3}$ fluoroalkoxy;
R$_2$ is R$_{2a}$ or -L$_2$-R$_{2b}$;
L$_2$ is —NR$_a$— or —NR$_c$CH$_2$—;
R$_c$ is H, C$_{1-3}$ alkyl, C$_{1-3}$ fluoroalkyl, C$_{3-6}$ cycloalkyl, or (C$_{1-3}$ alkoxy)-(C$_{1-3}$ alkylenyl);
R$_{2a}$ is a nitrogen-linked heterocyclyl selected from imidazolyl, indolinyl, morpholinyl, piperidinyl, pyrazolyl, pyrrolidinyl, pyrrolyl, triazolyl, 1,2,3,4-tetrahydro-1,5-naphthyridinyl, 1,2,3,4-tetrahydro-1,7-naphthyridinyl, 1,2,3,4-tetrahydroquinolinyl, 1,2,3-triazolo[4,5-b]pyridinyl, benzo[d][1,2,3]triazolyl, benzo[d]imidazolyl, imidazo[4,5-b]pyridinyl, imidazo[4,5-c]pyridinyl, indazolyl, indolyl, pyrazolo[3,4-b] pyrazinyl, pyrazolo[3,4-b]pyridinyl, pyrazolo[3,4-c]pyridinyl, pyrazolo[4,3-b] pyridinyl, pyrazolo[4,3-c]pyridinyl, pyrazolo[4,3-d]pyrimidinyl, pyrrolo[2,3-b] pyridinyl, pyrrolo[2,3-c]pyridinyl, pyrrolo[3,2-b]pyridinyl, pyrrolo[3,2-c]pyridinyl, 2,3-dihydro-pyrrolo[2,3-b]pyridinyl, 2,3-dihydro-pyrrolo[2,3-c]pyridinyl, 2,3-dihydro-pyrrolo[3,2-b]pyridinyl, 2,3-dihydro-pyrrolo[3,2-c] pyridinyl, 3,4-dihydro-benzo[b][1,4]oxazinyl, imidazo[4,5-b]pyridinyl, imidazo[4,5-c]pyridinyl, 5,6,7,8-tetrahydropyrido[3,2-d]pyrimidinyl, pyrrolo[2,3-b] pyrazinyl, pyrrolo[3,2-c] pyridazinyl, pyrrolo[3,2-d] pyrimidinyl, 6,7-dihydro-pyrrolo[3,2-d]pyrimidinyl, and purinyl, wherein each of said heterocyclyl is substituted with zero to 4 R$_d$;
R$_{2b}$ is phenyl or a carbon-linked heterocyclyl selected from pyrrolyl, furan, thiophenyl, imidazolyl, oxazolyl, thiazolyl, pyrazolyl, isoxazolyl, isothiazolyl, 1,2,3-triazolyl, 1,2,3-thiadiazolyl, 1,3,4-thiadiazolyl, 1,2,3-oxadiazolyl, 1,3,4-oxadiazolyl, 1,2,4-triazolyl, tetrazolyl, pyridinyl, pyridazinyl, pyrimidinyl, pyrazinyl, 1,2,4-triazinyl, benzo[c][1,2,5]oxadiazolyl, benzo[c]isothiazolyl, benzo[c]isoxazolyl, benzo[d]imidazolyl, benzo[d] isothiazolyl, benzo[d]isoxazolyl, benzo[d]oxazol-2 (3H)-onyl, benzo[d]oxazolyl, benzo[d]thiazolyl, indazolyl, indolyl, isobenzofuran-1(3H)-onyl, isochroman-1-only, pyrazolo[1,5-a]pyrimidinyl, pyrrolo[2,3-b] pyridinyl, pyrrolo[2,3-c]pyridinyl, pyrrolo[3,2-b] pyridinyl, and pyrrolo[3,2-c]pyridinyl; wherein each of said phenyl and said heterocyclyl is substituted with zero to 4 R$_d$;
each R$_3$ is independently H, C$_{1-3}$ alkyl, C$_{1-3}$ haloalkyl, C$_{1-3}$ hydroxyalkyl, C$_{3-6}$ cycloalkyl, (C$_{1-3}$ alkoxy)-(C$_{1-3}$ alkylenyl), —C(O)OR$_e$, or —C(O)NR$_e$R$_e$;
each R$_4$ is independently H, C$_{1-3}$ alkyl, C$_{1-3}$ haloalkyl, C$_{1-3}$ hydroxyalkyl, C$_{3-6}$ cycloalkyl, (C$_{1-3}$ alkoxy)-(C$_{1-3}$ alkylenyl), aryl, heteroaryl, —CO$_2$H, —CO$_2$R$_e$, —CONHR$_e$, —CONR$_e$R$_e$, or —NR$_{4a}$R$_{4a}$, wherein each of said cycloalkyl, aryl, and said heteroaryl is substituted with zero to 3 R$_d$;

each R$_{4a}$ is independently H, C$_{1-3}$ alkyl, C$_{1-3}$ fluoroalkyl, C$_{3-6}$ cycloalkyl, aryl, or heteroaryl, wherein each of said cycloalkyl, aryl, and said heteroaryl is substituted with zero to 3 R$_d$; or two R$_{4a}$ along with the nitrogen atom to which they are attached form a 3-7 membered heterocyclyl;
each R$_d$ is independently F, Cl, —OH, —CN, C$_{1-3}$ alkyl, C$_{1-3}$ fluoroalkyl, C$_{3-6}$ cycloalkyl, C$_{1-3}$ alkoxy, C$_{1-3}$ fluoroalkoxy, —C(O)OR$_e$, —C(O)NR$_e$R$_e$, —OC(O) NR$_e$R$_e$, —NHC(O)OR$_e$, —NR$_e$C(O)OR$_e$, —S(O)$_2$R$_e$, or tetrazolyl; and
each R$_e$ is independently H, C$_{1-3}$ alkyl, C$_{1-3}$ fluoroalkyl, C$_{3-6}$ cycloalkyl, aryl, or heteroaryl; or two R$_e$ along with the nitrogen atom to which they are attached form a 3-7 membered heterocyclyl.

2. A compound having the structure of Formula (I)

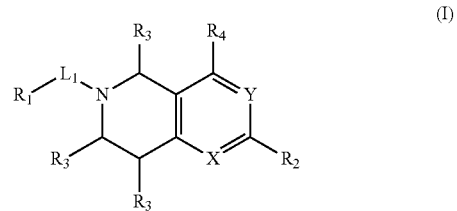

(I)

or a salt thereof, wherein:
X is CR$_4$ or N;
Y is CR$_4$ or N, provided that Y is N only if X is N;
R$_1$ is:

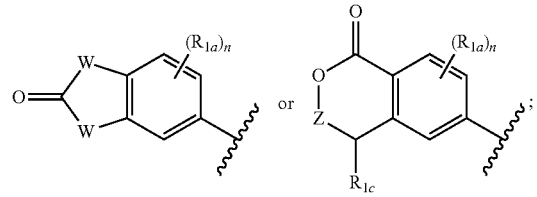

each W is independently NR$_{1b}$ or O;
Z is a bond or CHR$_{1d}$;
each R$_{1a}$ is independently H, F, Cl, —OH, C$_{1-3}$ alkyl, C$_{1-3}$ fluoroalkyl, C$_{3-6}$ cycloalkyl, C$_{1-3}$ alkoxy, or C$_{1-3}$ fluoroalkoxy;
each R$_{1b}$ is independently H, C$_{1-3}$ alkyl, C$_{1-3}$ fluoroalkyl, aryl, or heteroaryl;
R$_{1c}$ is H, C$_{1-4}$ alkyl, or C$_{3-6}$ cycloalkyl;
R$_{1d}$ is H, C$_{1-3}$ alkyl, C$_{3-6}$ cycloalkyl, or C$_{1-3}$ alkoxy;
n is zero, 1, 2, or 3;
L$_1$ is a bond, —CHR$_b$—, or —CHR$_a$CHR$_b$—;
R$_a$ is H, halo, —OH, C$_{1-4}$ alkyl, C$_{1-3}$ fluoroalkyl, C$_{1-3}$ hydroxyalkyl, C$_{3-6}$ cycloalkyl, C$_{1-3}$ alkoxy, or C$_{1-3}$ fluoroalkoxy;
R$_b$ is H, C$_{1-4}$ alkyl, C$_{1-3}$ fluoroalkyl, C$_{1-3}$ hydroxyalkyl, C$_{3-6}$ cycloalkyl, C$_{1-3}$ alkoxy, or C$_{1-3}$ fluoroalkoxy;
R$_2$ is R$_{2a}$ or -L$_2$-R$_{2b}$;
L$_2$ is —NR$_a$— or —NR$_c$CH$_2$—;
R$_c$ is H, C$_{1-3}$ alkyl, C$_{1-3}$ fluoroalkyl, C$_{3-6}$ cycloalkyl, or (C$_{1-3}$ alkoxy)-(C$_{1-3}$ alkylenyl);
R$_{2a}$ is a nitrogen-linked heterocyclyl selected from imidazolyl, indolinyl, morpholinyl, piperidinyl, pyrazolyl, pyrrolidinyl, pyrrolyl, triazolyl, 1,2,3,4-tetrahydro-1,5-naphthyridinyl, 1,2,3,4-tetrahydro-1,7-naphthyridinyl, 1,2,3,4-tetrahydroquinolinyl, 1,2,3-triazolo[4,5-b]pyridinyl, benzo[d][1,2,3]triazolyl, benzo[d]imidazolyl, imidazo[4,5-b]pyridinyl, imidazo[4,5-c]pyridinyl, indazolyl, indolyl, pyrazolo[3,4-b] pyrazinyl, pyrazolo[3,4-b]pyridinyl, pyrazolo[3,4-c]pyridinyl, pyrazolo[4,3-b] pyridinyl, pyrazolo[4,3-c]pyridinyl, pyrazolo[4,3-d]pyrimidinyl, pyrrolo[2,3-b] pyridinyl, pyrrolo[2,3-c]pyridinyl, pyrrolo[3,2-b]pyridinyl, pyrrolo[3,2-c]pyridinyl, 2,3-dihydro-pyrrolo[2,3-b]pyridinyl, 2,3-dihydro-pyrrolo[2,3-c]pyridinyl, 2,3-dihydro-pyrrolo[3,2-b]pyridinyl, 2,3-dihydro-pyrrolo[3,2-c]pyridinyl, 3,4-dihydro-benzo[b][1,4]oxazinyl, imidazo[4,5-b]pyridinyl, imidazo[4,5-c]pyridinyl, 5,6,7,8-tetrahydropyrido[3,2-d]pyrimidinyl, pyrrolo[2,3-b]pyrazinyl, pyrrolo[3,2-c] pyridazinyl, pyrrolo[3,2-d]pyrimidinyl, 6,7-dihydro-pyrrolo[3,2-d]pyrimidinyl, and purinyl, wherein each of said heterocyclyl is substituted with zero to 4 $R_d$;

$R_{2b}$ is phenyl or a carbon-linked heterocyclyl selected from pyrrolyl, furan, thiophenyl, imidazolyl, oxazolyl, thiazolyl, pyrazolyl, isoxazolyl, isothiazolyl, 1,2,3-triazolyl, 1,2,3-thiadiazolyl, 1,3,4-thiadiazolyl, 1,2,3-oxadiazolyl, 1,3,4-oxadiazolyl, 1,2,4-triazolyl, tetrazolyl, pyridinyl, pyridazinyl, pyrimidinyl, pyrazinyl, 1,2,4-triazinyl, benzo[c][1,2,5]oxadiazolyl, benzo[c]isothiazolyl, benzo[c]isoxazolyl, benzo[d]imidazolyl, benzo[d]isothiazolyl, benzo[d]isoxazolyl, benzo[d]oxazol-2(3H)-onyl, benzo[d]oxazolyl, benzo[d]thiazolyl, indazolyl, indolyl, isobenzofuran-1(3H)-onyl, isochroman-1-only, pyrazolo[1,5-a]pyrimidinyl, pyrrolo[2,3-b] pyridinyl, pyrrolo[2,3-c]pyridinyl, pyrrolo[3,2-b] pyridinyl, and pyrrolo[3,2-c]pyridinyl; wherein each of said phenyl and said heterocyclyl is substituted with zero to 4 $R_d$;

each $R_3$ is independently H, $C_{1-3}$ alkyl, $C_{1-3}$ haloalkyl, $C_{1-3}$ hydroxyalkyl, $C_{3-6}$ cycloalkyl, ($C_{1-3}$ alkoxy)-($C_{1-3}$ alkylenyl), —C(O)O$R_e$, or —C(O)N$R_eR_e$;

each $R_4$ is independently H, $C_{1-3}$ alkyl, $C_{1-3}$ haloalkyl, $C_{1-3}$ hydroxyalkyl, $C_{3-6}$ cycloalkyl, ($C_{1-3}$ alkoxy)-($C_{1-3}$ alkylenyl), aryl, heteroaryl, —CO$_2$H, —CO$_2R_e$, —CONH$R_e$, —CON$R_eR_e$, or —N$R_{4a}R_{4a}$, wherein each of said cycloalkyl, aryl, and said heteroaryl is substituted with zero to 3 $R_d$;

each $R_{4a}$ is independently H, $C_{1-3}$ alkyl, $C_{1-3}$ fluoroalkyl, $C_{3-6}$ cycloalkyl, aryl, or heteroaryl, wherein each of said cycloalkyl, aryl, and said heteroaryl is substituted with zero to 3 $R_d$; or two $R_{4a}$ along with the nitrogen atom to which they are attached form a 3-7 membered heterocyclyl;

each $R_d$ is independently F, Cl, —OH, —CN, $C_{1-3}$ alkyl, $C_{1-3}$ fluoroalkyl, $C_{3-6}$ cycloalkyl, $C_{1-3}$ alkoxy, $C_{1-3}$ fluoroalkoxy, —C(O)O$R_e$, —C(O)N$R_eR_e$, —OC(O)N$R_eR_e$, —NHC(O)O$R_e$, —N$R_e$C(O)O$R_e$, or —S(O)$_2R_e$; and each $R_e$ is independently H, $C_{1-3}$ alkyl, $C_{1-3}$ fluoroalkyl, $C_{3-6}$ cycloalkyl, aryl, or heteroaryl; or two $R_e$ along with the nitrogen atom to which they are attached form a 3-7 membered heterocyclyl.

3. The compound of claim 1 or a salt thereof, wherein:
$R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 4 $R_d$; and
$R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 4 $R_d$.

4. The compound of claim 1 or a salt thereof, wherein:
$R_1$ is:

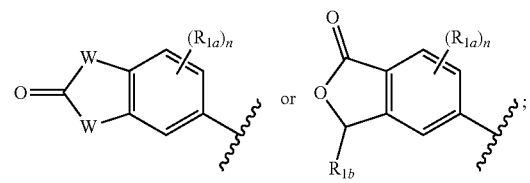

one W is N$R_{1b}$ and the other W is O;

each $R_{1a}$ is independently selected from F, Cl, $C_{1-3}$ alkyl, $C_{1-3}$ fluoroalkyl, and $C_{3-6}$ cycloalkyl;

$R_{1b}$ is H, $C_{1-3}$ alkyl, or $C_{1-3}$ fluoroalkyl;

$R_{1c}$ is H, $C_{1-2}$ alkyl, or $C_{3-6}$ cycloalkyl;

n is zero, 1, or 2;

$R_a$ is H, F, —OH, $C_{1-2}$ alkyl, —CF$_3$, —CH$_2$OH, cyclopropyl, —OCH$_3$, or —OCF$_3$;

$R_b$ is H, $C_{1-2}$ alkyl, or cyclopropyl;

$R_c$ is H or —CH$_3$;

$R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 3 $R_d$;

$R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 3 $R_d$;

each $R_3$ is independently H, $C_{1-2}$ alkyl, $C_{1-2}$ fluoroalkyl, $C_{1-2}$ hydroxyalkyl, or $C_{3-6}$ cycloalkyl;

each $R_4$ is independently H, —CH$_3$, —CF$_3$, cyclopropyl, phenyl, or —N$R_{4a}R_{4a}$;

each $R_{4a}$ is independently H or —CH$_3$;

each $R_d$ is independently F, Cl, —OH, —CN, $C_{1-2}$ alkyl, $C_{1-2}$ fluoroalkyl, $C_{3-6}$ cycloalkyl, $C_{1-2}$ alkoxy, —OCF$_3$, —C(O)O$R_e$, —C(O)N$R_eR_e$, —OC(O)N$R_eR_e$, —NHC(O)O$R_e$, —N$R_e$C(O)O$R_e$, or —S(O)$_2R_e$; and each $R_e$ is independently H, —CH$_3$, —CF$_3$, or $C_{3-6}$ cycloalkyl.

5. The compound of claim 1 or a salt thereof, having the structure of Formula (Ib) or (Ic):

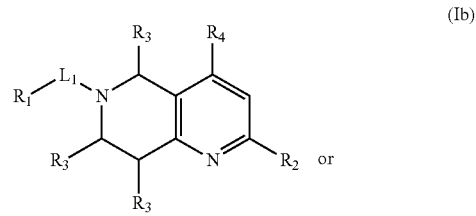

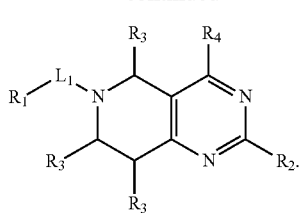

6. The compound of claim 1 or a salt thereof, having the structure of Formula (Ia):

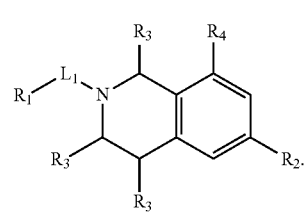

7. The compound of claim 1 or a salt thereof, wherein $R_2$ is $R_{2a}$.

8. The compound of claim 1 or a salt thereof, wherein $R_2$ is $-L_2-R_{2b}$.

9. The compound of claim 1 or a salt thereof, wherein:
$R_1$ is

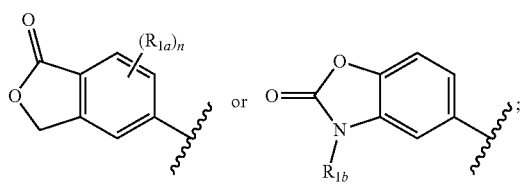

$R_{1b}$ is H or —CH$_3$;
$L_1$ is a bond, —CH$_2$—, —CH$_2$CH$_2$—, —CH(CH$_2$OH)—, or —CH(OH)CH$_2$—;
$L_2$ is —NH—, —N(CH$_3$)—, or —NHCH$_2$—;
$R_{2a}$ is a nitrogen-linked heteroaryl selected from benzo[d]imidazolyl, indazolyl, indolyl, pyrazolo[3,4-b]pyridinyl, pyrazolo[3,4-c]pyridinyl, pyrazolo[4,3-b]pyridinyl, pyrrolo[2,3-b]pyridinyl, pyrrolo[2,3-c]pyridinyl, and pyrrolo[3,2-b]pyridinyl, wherein each of said heteroaryl is substituted with zero to 1 substituent selected from —CN;
$R_{2b}$ is phenyl or a carbon-linked heteroaryl selected from pyridinyl, pyrimidinyl, isobenzofuranonyl, benzo[d]oxazolonyl, and pyrazolo[1,5-a]pyrimidinyl, wherein each of said phenyl and said heteroaryl is substituted with zero to 2 substituents independently selected from F, —CN, and —CH$_3$;
each $R_3$ is H; and
each $R_4$ is H.

10. The compound according to claim 1 or a salt thereof, wherein said compound is:
1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-4-carbonitrile;
2-fluoro-5-((6-((1-oxo-1,3-dihydroisobenzofuran-5-yl)methyl)-5,6,7,8-tetrahydropyrido[4,3-d]pyrimidin-2-yl)amino)benzonitrile;
1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indazole-4-carbonitrile;
2-fluoro-4-((2-((1-oxo-1,3-dihydroisobenzofuran-5-yl)methyl)-1,2,3,4-tetrahydroisoquinolin-6-yl) amino) benzonitrile;
4-methyl-5-((2-((4-methyl-1-oxo-1,3-dihydroisobenzofuran-5-yl)amino)-7,8-dihydropyrido[4,3-d]pyrimidin-6(5H)-yl)methyl)isobenzofuran-1(3H)-one;
2-fluoro-4-((2-(2-(1-oxo-1,3-dihydroisobenzofuran-5-yl)ethyl)-1,2,3,4-tetrahydroisoquinolin-6-yl)amino)benzonitrile;
2-fluoro-4-((6-(2-(1-oxo-1,3-dihydroisobenzofuran-5-yl)ethyl)-5,6,7,8-tetrahydro-1,6-naphthyridin-2-yl)amino)benzonitrile;
1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile;
1-(6-(2-hydroxy-1-(4-methyl-1-oxo-1,3-dihydroisobenzofuran-5-yl)ethyl)-5,6,7,8-tetrahydropyrido[4,3-d]pyrimidin-2-yl)-1H-indole-3-carbonitrile;
2-fluoro-4-(((2-(4-methyl-1-oxo-1,3-dihydroisobenzofuran-5-yl)-1,2,3,4-tetrahydroisoquinolin-6-yl)amino)methyl)benzonitrile;
1-(6-((1-oxo-1,3-dihydroisobenzofuran-5-yl)methyl)-5,6,7,8-tetrahydropyrido[4,3-d] pyrimidin-2-yl)-1H-indazole-5-carbonitrile;
1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-4-carbonitrile;
1-(6-((4-methyl-1-oxo-1,3-dihydroisobenzofuran-5-yl)methyl)-5,6,7,8-tetrahydropyrido[4,3-d]pyrimidin-2-yl)-1H-indazole-5-carbonitrile;
3-methyl-5-((2-((4-methyl-1-oxo-1,3-dihydroisobenzofuran-5-yl)methyl)-1,2,3,4-tetrahydroisoquinolin-6-yl)amino)benzo[d]oxazol-2(3H)-one;
5-((6-((1-oxo-1,3-dihydroisobenzofuran-5-yl)amino)-3,4-dihydroisoquinolin-2(1H)-yl)methyl)isobenzofuran-1(3H)-one;
1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-5-carbonitrile-;
1-(6-(2-hydroxy-2-(1-oxo-1,3-dihydroisobenzofuran-5-yl)ethyl)-5,6,7,8-tetrahydropyrido[4,3-d] pyrimidin-2-yl)-1H-indole-5-carbonitrile;
1-(6-(2-hydroxy-2-(1-oxo-1,3-dihydroisobenzofuran-5-yl)ethyl)-5,6,7,8-tetrahydropyrido[4,3-d] pyrimidin-2-yl)-1H-indole-4-carbonitrile;
1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-4-carbonitrile;
1-(6-((4-methyl-1-oxo-1,3-dihydroisobenzofuran-5-yl)methyl)-5,6,7,8-tetrahydropyrido[4,3-d]pyrimidin-2-yl)-1H-indole-4-carbonitrile;
1-(6-((4-methyl-1-oxo-1,3-dihydroisobenzofuran-5-yl)methyl)-5,6,7,8-tetrahydropyrido[4,3-d]pyrimidin-2-yl)-1H-indole-5-carbonitrile;
1-(6-(2-hydroxy-2-(3-methyl-2-oxo-2,3-dihydrobenzo[d]oxazol-5-yl)ethyl)-5,6,7,8-tetrahydropyrido[4,3-d]pyrimidin-2-yl)-1H-indole-4-carbonitrile;
1-(6-((4-methyl-1-oxo-1,3-dihydroisobenzofuran-5-yl)methyl)-5,6,7,8-tetrahydropyrido[4,3-d]pyrimidin-2-yl)-1H-indole-3-carbonitrile;
1-(2-((4-methyl-1-oxo-1,3-dihydroisobenzofuran-5-yl)methyl)-1,2,3,4-tetrahydroisoquinolin-6-yl)-1H-indole-4-carbonitrile;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indole-6-carbonitrile;

2-fluoro-4-((6-((4-methyl-1-oxo-1,3-dihydroisobenzofuran-5-yl)methyl)-5,6,7,8-tetrahydropyrido[4,3-d]pyrimidin-2-yl)amino)benzonitrile;

2-fluoro-4-((6-(2-(4-methyl-1-oxo-1,3-dihydroisobenzofuran-5-yl)ethyl)-5,6,7,8-tetrahydropyrido[4,3-d]pyrimidin-2-yl)amino)benzonitrile;

2-fluoro-4-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)benzonitrile;

2-fluoro-4-((6-(2-hydroxy-1-(4-methyl-1-oxo-1,3-dihydroisobenzofuran-5-yl)ethyl)-5,6,7,8-tetrahydropyrido[4,3-d]pyrimidin-2-yl)amino)benzonitrile;

2-fluoro-4-((6-(2-hydroxy-1-(4-methyl-1-oxo-1,3-dihydroisobenzofuran-5-yl)ethyl)-5,6,7,8-tetrahydropyrido[4,3-d]pyrimidin-2-yl)amino)benzonitrile;

2-fluoro-4-((2-((4-methyl-1-oxo-1,3-dihydroisobenzofuran-5-yl)methyl)-1,2,3,4-tetrahydroisoquinolin-6-yl)amino)benzonitrile;

4-methyl-6-((6-((4-methyl-1-oxo-1,3-dihydroisobenzofuran-5-yl)methyl)-5,6,7,8-tetrahydropyrido[4,3-d]pyrimidin-2-yl)amino)nicotinonitrile;

2-fluoro-4-((2-(2-hydroxy-2-(4-methyl-1-oxo-1,3-dihydroisobenzofuran-5-yl)ethyl)-1,2,3,4-tetrahydroisoquinolin-6-yl)amino)benzonitrile;

2-fluoro-4-((2-(2-hydroxy-1-(4-methyl-1-oxo-1,3-dihydroisobenzofuran-5-yl)ethyl)-1,2,3,4-tetrahydroisoquinolin-6-yl)amino)benzonitrile;

4-methyl-6-((2-((1-oxo-1,3-dihydroisobenzofuran-5-yl)methyl)-1,2,3,4-tetrahydroisoquinolin-6-yl)amino)nicotinonitrile;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-b]pyridine-4-carbonitrile;

5-(2-(2-(1H-pyrrolo[3,2-b]pyridin-1-yl)-7,8-dihydropyrido[4,3-d]pyrimidin-6(5H)-yl)-1-hydroxy ethyl)-4-methylisobenzofuran-1(3H)-one;

2-((2-((4-methyl-1-oxo-1,3-dihydroisobenzofuran-5-yl)methyl)-1,2,3,4-tetrahydroisoquinolin-6-yl)amino)pyrimidine-5-carbonitrile;

4-methyl-5-((6-(pyrazolo[1,5-a]pyrimidin-5-ylamino)-3,4-dihydroisoquinolin-2(1H)-yl)methyl)isobenzofuran-1(3H)-one;

2-fluoro-6-((2-((4-methyl-1-oxo-1,3-dihydroisobenzofuran-5-yl)methyl)-1,2,3,4-tetrahydroisoquinolin-6-yl)amino)benzonitrile;

1-(6-((4-methyl-1-oxo-1,3-dihydroisobenzofuran-5-yl)methyl)-5,6,7,8-tetrahydropyrido[4,3-d] pyrimidin-2-yl)-1H-benzo[d]imidazole-4-carbonitrile;

5-(2-(2-(1H-pyrazolo[4,3-b]pyridin-1-yl)-7,8-dihydropyrido[4,3-d]pyrimidin-6(5H)-yl)-1-hydroxyethyl)-4-methylisobenzofuran-1(3H)-one;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-c]pyridine-4-carbonitrile;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[3,4-c]pyridine-4-carbonitrile;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-5-carbonitrile;

1-(6-(2-hydroxy-1-(4-methyl-1-oxo-1,3-dihydroisobenzofuran-5-yl)ethyl)-5,6,7,8-tetrahydropyrido[4,3-d]pyrimidin-2-yl)-1H-pyrrolo[2,3-b]pyridine-5-carbonitrile;

1-(6-((1-oxo-1,3-dihydroisobenzofuran-5-yl)methyl)-5,6,7,8-tetrahydropyrido[4,3-d]pyrimidin-2-yl)-1H-pyrrolo[2,3-b]pyridine-5-carbonitrile;

2-fluoro-4-(methyl(6-((4-methyl-1-oxo-1,3-dihydroisobenzofuran-5-yl)methyl)-5,6,7,8-tetrahydropyrido[4,3-d]pyrimidin-2-yl)amino)benzonitrile;

2-fluoro-4-((2-((3-methyl-2-oxo-2,3-dihydrobenzo[d]oxazol-5-yl)methyl)-1,2,3,4-tetrahydroisoquinolin-6-yl)amino)benzonitrile;

3-methyl-5-((6-((4-methyl-1-oxo-1,3-dihydroisobenzofuran-5-yl)methyl)-5,6,7,8-tetrahydropyrido[4,3-d]pyrimidin-2-yl)amino)benzo[d]oxazol-2(3H)-one;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-5-carbonitrile;

ethyl 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazolo[4,3-b]pyridine-6-carboxylate;

methyl 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[3,2-b]pyridine-6-carboxylate;

5-(2-(2-(1H-imidazo[4,5-b]pyridin-1-yl)-7,8-dihydropyrido[4,3-d]pyrimidin-6(5H)-yl)-1-hydroxyethyl)-4-methylisobenzofuran-1(3H)-one;

5-(1-hydroxy-2-(2-(pyridin-3-ylamino)-7,8-dihydropyrido[4,3-d] pyrimidin-6(5H)-yl)ethyl)-4-methylisobenzofuran-1(3H)-one;

5-(2-(2-(3H-imidazo[4,5-b]pyridin-3-yl)-7,8-dihydropyrido[4,3-d]pyrimidin-6(5H)-yl)-1-hydroxyethyl)-4-methylisobenzofuran-1(3H)-one;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrazole-4-carbonitrile;

2-fluoro-4-((7-(hydroxymethyl)-6-((4-methyl-1-oxo-1,3-dihydroisobenzofuran-5-yl)methyl)-5,6,7,8-tetrahydropyrido[4,3-d]pyrimidin-2-yl)amino)benzonitrile;

2-fluoro-4-((7-(hydroxymethyl)-6-((4-methyl-1-oxo-1,3-dihydroisobenzofuran-5-yl)methyl)-5,6,7,8-tetrahydropyrido[4,3-d]pyrimidin-2-yl)amino)benzonitrile;

5-(1-hydroxy-2-(2-(4-methyl-1H-imidazol-1-yl)-7,8-dihydropyrido[4,3-d]pyrimidin-6(5H)-yl) ethyl)-4-methylisobenzofuran-1(3H)-one;

5-(1-hydroxy-2-(2-(2-methyl-1H-imidazol-1-yl)-7,8-dihydropyrido[4,3-d]pyrimidin-6(5H)-yl) ethyl)-4-methylisobenzofuran-1(3H)-one;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-indazole-3-carbonitrile;

5-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)nicotinonitrile;

5-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)-3-methylbenzo[d]oxazol-2(3H)-one;

5-(2-(2-((5-(1H-tetrazol-1-yl)pyridin-2-yl)amino)-7,8-dihydropyrido[4,3-d]pyrimidin-6(5H)-yl)-1-hydroxy ethyl)-4-methylisobenzofuran-1(3H)-one;

6-((6-(2-hydroxy-2-(4-methyl-1-oxo-1,3-dihydroisobenzofuran-5-yl)ethyl)-5,6,7,8-tetrahydropyrido[4,3-d]pyrimidin-2-yl)amino)-4-methoxynicotinonitrile;

1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)indoline-4-carbonitrile;

1-(6-(2-hydroxy-2-(4-methyl-1-oxo-1,3-dihydroisobenzofuran-5-yl)ethyl)-5,6,7,8-tetrahydro pyrido[4,3-d]pyrimidin-2-yl)indoline-4-carbonitrile;

5-(2-(2-(1H-imidazol-1-yl)-7,8-dihydropyrido[4,3-d]pyrimidin-6(5H)-yl)-1-hydroxyethyl)-4-methylisobenzofuran-1(3H)-one;

5-(2-(2-(1H-benzo[d]imidazol-1-yl)-'7,8-dihydropyrido[4,3-d]pyrimidin-6(5H)-yl)-1-hydroxy ethyl)-4-methylisobenzofuran-1(3H)-one; or 1-(6-(2-hydroxy-2-(4-methyl-1-oxo-1,3-dihydroisobenzofuran-5-yl)ethyl)-5,6,7,8-tetrahydropyrido[4,3-d]pyrimidin-2-yl)-1H-pyrrolo[3,2-b]pyridine-3-carbonitrile.

11. A pharmaceutical composition comprising one or more compounds of claim 1 or a salt thereof and a pharmaceutically acceptable carrier or diluent.

12. A method for the treatment of a cardiovascular disease, which comprises administering to a patient in need thereof a therapeutically effective amount of a compound of claim 1, or pharmaceutically acceptable salt thereof.

13. The method of claim 12, wherein said disease is selected from hypertension, coronary heart disease, stroke, heart failure, systolic heart failure, diastolic heart failure, diabetic heart failure, acute-decompensated heart failure, post-operative volume overload, idiopathic edema, pulmonary hypertension, pulmonary arterial hypertension, cardiac insufficiency, nephrotic syndrome, and acute kidney insufficiency.

14. A method for the promotion of diuresis or natriuresis, which comprises administering to a patient in need thereof a therapeutically effective amount of a compound of claim 1, or pharmaceutically acceptable salt thereof.

* * * * *

UNITED STATES PATENT AND TRADEMARK OFFICE
CERTIFICATE OF CORRECTION

PATENT NO. : 10,851,108 B2
APPLICATION NO. : 16/094288
DATED : December 1, 2020
INVENTOR(S) : Prashantha Gunaga et al.

It is certified that error appears in the above-identified patent and that said Letters Patent is hereby corrected as shown below:

In the Claims

In Column 107, Line 18, Claim 1, delete "-$NR_a$-" and insert -- -$NR_c$- --, therefor.

In Column 108, Line 61, Claim 2, delete "-$NR_a$-" and insert -- -$NR_c$- --, therefor.

In Column 113, Line 44, Claim 10, delete "ylamino)" and insert -- yl)amino) --, therefor.

In Column 114, Line 31, Claim 10, delete "ylamino)" and insert -- yl)amino) --, therefor.

In Column 115, Line 17, Claim 11, after "thereof" insert -- ; --.

Signed and Sealed this
Ninth Day of November, 2021

Drew Hirshfeld
*Performing the Functions and Duties of the*
*Under Secretary of Commerce for Intellectual Property and*
*Director of the United States Patent and Trademark Office*